US006800747B1

(12) United States Patent
Pestka

(10) Patent No.: US 6,800,747 B1
(45) Date of Patent: *Oct. 5, 2004

(54) NUCLEIC ACIDS ENCODING PHOSPHORYLATED FUSION PROTEINS

(75) Inventor: Sidney Pestka, North Caldwell, NJ (US)

(73) Assignee: Pestka Biomedical Laboratories, Inc.

( * ) Notice: Subject to any disclaimer, the term of this patent is extended or adjusted under 35 U.S.C. 154(b) by 429 days.

This patent is subject to a terminal disclaimer.

(21) Appl. No.: 09/723,775

(22) Filed: Nov. 28, 2000

Related U.S. Application Data

(63) Continuation of application No. 09/246,830, filed on Feb. 8, 1999, now Pat. No. 6,514,753, which is a continuation of application No. 08/487,057, filed on Jun. 7, 1995, now Pat. No. 6,150,503.

(51) Int. Cl.$^7$ .......................... C12N 5/10; C12N 15/20; C12N 15/62

(52) U.S. Cl. .................. 536/23.4; 435/69.7; 435/252.3; 435/254.11; 435/320.1; 435/471; 435/325; 530/351; 530/399

(58) Field of Search ............................... 536/23.4, 23.1, 536/23.5; 435/69.7, 252.3, 254.11, 320.1, 471, 325; 530/351, 399

(56) References Cited

U.S. PATENT DOCUMENTS

| 4,478,817 A | 10/1984 | Campbell et al. ............ 424/7.1 |
| 4,569,908 A | 2/1986 | Mark et al. .................... 435/70 |
| 4,591,552 A | 5/1986 | Neurath ......................... 435/7 |
| 4,695,623 A | 9/1987 | Stabinsky .................... 530/351 |
| 4,758,428 A | 7/1988 | Mark et al. .................... 424/85 |
| 4,877,777 A | 10/1989 | DiLuzio ....................... 514/54 |
| 5,001,064 A | 3/1991 | Deuel .......................... 435/194 |
| 5,459,240 A | 10/1995 | Foxwell et al. ............. 530/328 |
| 5,986,061 A | 11/1999 | Pestka |
| 6,150,503 A | 11/2000 | Pestka |
| 6,225,455 B1 * | 5/2001 | Pestka ........................ 536/23.4 |
| 6,514,753 B1 * | 2/2003 | Pestka ..................... 435/320.1 |

OTHER PUBLICATIONS

U.S. patent application Ser. No. 09/723,942, Pestia, filed Apr. 13, 2001.
Adolf et al., "Natural Human Interferon–α2 is O–glycosylated", Biochem. J., 276:511–518 (1991).
Aguet, M. "High–affinity Binding of$^{125}$–I–Labelled Mouse Interferon to a Specific Cell Surface Receptor", Nature, 284: 459–461 (1980).
Arakawa, et al., "Sites of Phosphorylation In Recombinant Human Interferon–γ", Biochem. Biophys. Res. Comm. 136: 679–684 (1986).
Aruffo, A., Seed, B., "Molecular Cloning of Two CD7 (T–Cell Leukemia Antigen) cDNAs by a COS Cell Expression System", EMBO J, 6: 3313–3316 (1987).

Bernard, H.–U., et al., "Use of the λ Phage Promoter $P_L$ to Promote Gene Expression in Hybrid Plasmid Cloning Vehicles", Methods in Enzymology, 68, 482–492.
Bradford, M.M. (1976), "A Rapid and Sensitive Method for the Quantitation of Microgram Quantities of Protein Utilizing the Principle of Proein–Dye Binding", Anal. Biochem., 72:248–254.
Branca, A.A., et al., "Evidence That Types I and II Interferons Have Different Receptors", Nature, 294: 768–770 (1981).
Bray, G.A., "A Simple Efficient Liquid Scintillator for Counting Aqueous Solutions in a Liquid Scintillation Counter", Anal. Biochem., 1:279–285 (1960).
Canaai, D., et al., "Regulated Expression of Human Interferon $β_1$ Gene After Transduction Into Cultured Mouse and Rabbit Cells", Proc. Natl. Acad. Sci. USA, 79: 5166–5170 (1982).
Carter, P.J., et al., "The Use of Double Mutants to Detect Structural Changes in the Active Site of the Tyrosyl–tRNA Synthetase (Bacillus stearothermophilus)", Cell, 38: 835–840 (1984).
Chang, N.T., et al., "Synthesis of a Human Leukocyte Interferon with a Modified Carboxy Terminus in Escherichia coli", Arch. Biochem. Biophys., 221: 585–589 (1983).
Cohen, et al., "Protein Phosphorylation and the Neural and Hormonal Control of Enzyme Activity", Posttranslational Covalent Modification of Proteins: 19–38 (1983).
Cola, et al., "Synthetic Peptides Reproducing the EGF–receptor Segment Homologous to the pp60(^–src) Phosphoacceptor Site: Phosphohorylation by Tyrosine Protein Kinases", Biochemica et Biophysica Acta, 1012: 191–195 (1989).
Cone, R.D., et al., "Regulated Expression of a Complete Human β–Globin Gene Encoded by a Transmissible Retrovirus Vector", Molecular & Cellular Biology, 7:887–897 (1987).
Cooper et al., "Phosphorylation Sites in Enolase and Lactate Dehydrogynase Utilized by Tyrosine Protein Kinases in Vivo and in Vitro", The Journal of Biological Chemistry, 259(12): 7835–7841 (1984).
Corbin, J.D., et al., Methods in Enzymology, 159, Section IV: General Methods Related to Protein Phosphatases, pp. 335–453 (1988).

(List continued on next page.)

Primary Examiner—Prema Mertz
(74) Attorney, Agent, or Firm—Ropes & Gray LLP

(57) ABSTRACT

Modified proteins, modified interferons α's and β's, phosphorylated modified proteins and DNA sequences encoding the above, applications and uses thereof. Modified phosphorylated Hu-IFN-α-like proteins are provided which carry an identifiable label such as a radio-label. Corresponding phosphorylatable, Hu-IFN-α-like proteins which contain a putative phosphorylation site. DNA sequences which encode a Hu-IFN-α-like protein and contain a sequence encoding a putative phosphorylatable site. Appropriate expression vectors are used to transform compatible host cells of various microorganisms, such as E. coli. Numerous uses for the phosphorylated proteins are disclosed.

10 Claims, 14 Drawing Sheets-

OTHER PUBLICATIONS

Crowl, R., "Expression of Human Interferon Genes in *E coli* with the Lambda $P_L$ Promoter", *Methods in Enzymology*, 119: 376–383 (1986).

Crowl, R., et al., "Versatile Expression Vectors for High–Level Synthesis of Cloned Gene Products in *Escherichia coli*", *Gene*, 38: 31–38 (1985).

Czarniecki, C.N., et al., "Synergistic Antiviral and Antiproliferative Activities of *Escherichia coli*–Derived Human Alpha, Beta, and Gamma Interferons†", *J. Virol.*, 49: 490–496 (1984).

Downs, D., et al., "Isolation and Characterization of Ion Mutants in *Salmonella typhimurium*", *J. Bacteriol.*, 165: 193–197 (1986).

Edelman, MA et al., "Protein Serine/Threonine Kinases", *Ann. Rev. Biochem.*, 56: 567–613 (1987).

Familetti, P.C., et al., "A Convenient and Rapid Cytopathic Effect Inhibition Assay for Interferon", *Methods in Enzymology*, 78: 387–394 (1981).

Fantes, K.H., "Chemical Modification of Human and Murine Interferons", *Methods in Enzymology*, 119: 233–241 (1986).

Feng et al., "Antiproliferative Activity of a Hybrid Protein Between Interferon–y and Tumor Necrosis Factor–β", *Science* 241: 1501–1503 (1988).

Feramisco, et al., "Phosphorylation of Hydroxyproline in a Synthetic Peptide Catalyzed by Cyclic AMP–Dependent Protein Kinase*", *J. Biol. Chem.* 254: 6987–6990 (1979).

Fields, R. et al., "Recombinant Rat and Murine Immune Interferons Are Phosphorylated at a Single Site, Ser(^132)", *J. Interferon Res.*, 549–557 (1988).

Franklin et al., "Effect of Murine Gamma–Interferon on the Mouse Liver and Its Drug–Metabolizing Enzymes: Comparison with Human Hybrid Alpha–Interferon", J. Interferon Res. 5:265–272 (1985).

Glass, D.B., et al., "Comparison of the Substrate Specificity of Adenosine 3':5'–Monophosphate– and Guanosine 3':5'–Monophospate–Dependent Protein Kinases", *J. Biol. Chem.*, 254: 9728–9738 (1979).

Glass, D.B., et al., "Protein Phosphorylation Catalyzed by Cyclic AMP–Dependent and Cyclic GMP–Dependent Protein Kinases", *Ann. Rev. Pharmacol. Toxicol.*, 20, 363–388 (1980).

Glenney, J.R., Jr., et al., "Monoclonal Antibodies to Phosphotyrosine", *J. Immunol. Methods*, 109(2): 277–85 (1988).

Goeddel, D.V., et al., "The Structure of Eight Distinct Cloned Human Leukocyte Interferon cDNAs", *Nature*, 290: 19–26 (1981).

Goeddel, D.V. et al., "Synthesis of human fibroblast interferon by *E. coli*", *Nucleic Acids Res.*, 8:4057–4074 (1980).

Goeddel, D.V. et al., "Human leukocyte interferon produced by *E. coli* is biologically active", Nature 287: 411–416 (1980).

Gottesman, M.E. et al., "Integration–negative Mutants of Bacteriophage Lambda", *J. Mol. Biol.*, 31: 487–505 (1968).

Greengard, P. "Phosphorylated Proteins as Physiological Effectors", *Science*, 199: 146–152 (1978).

Hall et al., "Phosporylation of Sinapsin I at a novel site by Proline–Directed Protein Kinase", *J. Biol. Chem.*, 265(12): 6944–6948 (1990).

Hellerman, J.G., et al., "Secretion of Human Parathyroid Hormone From Rate Pituitary Cells Infected With a Recombinant Retrovirus Encoding Preproparathyroid Hormone", *Proc. Natl. Acad. Sci. U.S.A.*, 81: 534–5344 (1984).

Hermann et al, "Enrichment and Characterization of Angiotensin II Using Affinity and High Pressure Liquid Chromatography", *Biochem. And Biophys. Res. Comm.*, 136(2): 685–700 (1986).

Hitzeman, R.A., et al., "Construction of Expression Vectors for Secretion of Human Interferons by Yeast", *Methods of Enzmol.*, 119: 424–33 (1986).

Hofer, et al., "Modification and Introduction of Protein Glycosylation Sites by Site–Specific Mutagenesis: Studies on Human Interleukin 2", *Biochem. Hoppe–Seyler*, 368: 1060 (1987).

Hotta, K., et al., "Detection of a Single Base Substitution Between Human Leukocyte IFN–αA and –α2 Genes with Octadecyl", *Method. in Enzymol.*, 119: 481–485 (1986).

Hunter T. et al., "Protein–Tyrosine Kinases", *Ann. Rev. Biochem.*, 54: 897–930 (1985).

Hunter, T., "A Thousand and One Protein Kinases", *Cell, 50:* 823–829 (1987).

Hwang, B.J. et al., "*Escherichia coli* Contains a Soluble ATP–Dependent Protease (Ti) Distinct from Protease La", *Proc Natl. Acad Sci USA*, 84:5550–5554 (1987).

Innis, M.A., et al., "Procedures for Expression, Modification, and Analysis of Human Fibroblast Interferon (IFN–β) Genes in Heterologous Cells", *Methods in Enzymol.*, 119:397–403 (1986).

Joshi, A.R., et al., "Interferon Receptors—Cross–Linking of Human Leukocyte Interferon α–2 to its Receptor on Human Cells*", *J. Biol. Chem.*, 257: 13884–13887 (1982).

Jung, V., et al., "Human Chromosomes 6 and 21 Are Required For Sensitivity To Human Interferon γ", *Proc. Natl. Acad. Sci. USA*, 84: 4151–4155 (1987).

Katayama–Fujimura, Y., et al., "A Multiple–Component, ATP–Dependent Protease From *Escherichia coli*\*", *J. Biol. Chem.*, 262: 4477–4485 (1987).

Kemp, B.E., et al., "Role of Multiple Basic Residues in Determining the Substrate Specificity of Cyclic AMP–Dependent Protein Kinase*", *J. Biol. Chem.*, 252, 4888–4894 (1977).

Knight, E., et al., "Human Fibroblast Interferon: Amino Acid Analysis and Amino Terminal Amino Acid Sequence", *Science*, 207: 525–526 (1980).

Kobrin, B.J., et al., "Sequences Near the 3' Secretion–Specific Polyadenylation Site Influence Levels of Secretion–Specific and Membrane–Specific IgG2b mRNA in Myeloma Cells", *Molecular & Cellular Biology*, 6: 1687–1697 (1986).

Kole, H.K., et al., "Specific Dephosphorylation of Phosphoproteins by Protein–Serine and –Tyrosine Kinasis", *Proc. Natl. Acad. Sci. U.S.A.*, 85: 5849–5853 (1988).

Krebs, GE et al., "Phosphorylation–Dephosphorylation of Enzymes", *Ann. Rev. Biochem.*, 48: 923–959 (1979).

Krisch, H.M., et al., "Nucleotide Sequences Involved in Bacteriophage T4 Gene 32 Translation Self–Regulation", *Proc. Natl. Acad. Sci. U.S.A.*, 79: 4937–4941 (1982).

Kuenzal et al, "Substrate Specificity Determinates for Casein Kinase II as Deduced from Studies With Synthetic Pepides", *J. Bio. Chem.*, 262 (19): 9136–9140 (1987).

Kung et al., "Phosphorylation of Human Immune Interferon (IFN–γ)", *Methods Enzymol.*, 119: 296–301 (1986).

Laemmli, U.K. "Cleavage of Structural Proteins During the Assembly of the Head of Bacteriophage T4", *Nature, 227:* 680–685 (1970).

Langer et al., "Preparation of a 32P–Labeled Murine Immune Interferon and Its Binding to the Mouse Immune Interferon Receptor", *J Bio. Chem., 261(21)*: 9801–9804 (1986).

Langer, J.A., et al., "Procedures for Studying Binding of Interferon to Human Cells in Suspension Cultures", *Methods In Enzymol., 119*: 305–311 (1986).

Langer, J.S. et al., "Binding of Human Alpha–Interferons to Natural Killer Cells", *J. Interferon Res., 6*: 97–105 (1986).

Leatherbarrow, RJ et al, "Protein Engineering", *Protein Engineering, 1(1)*: 7–16 (1986).

Li, B.–L., et al., "Creation of Phosphorylation Sites in Proteins: Construction of a Phosphorylatable Human Interferon α", *Proc. Natl. Acad. Sci. USA, 86*: 558–562 (1989).

Liebhaber et al., "Homology and Concerted Evolution at the α1 and α2 Loci of Human α–globin", *Nature, 290*: 26–29 (1981).

Linder, M.E., et al., "Immunological Characterization of Proteins Detected by Phosphotyrosine Antibodies in Cells Transformed By Rous Sarcoma Virus", *J. Virol., 62(8)*: 2665–2673 (1988).

Lowry, OH et al., "Protein Measurement with the Folin Phenol Reagent", J. Biol. Chem. 193: 265–275 (1951).

Lyons R.H., et al., "Pentapeptide Nuclear Localization Signal in Adenovirus Ela", *Mol. Cell. Biol., 7*:2451–2456 (1987).

Maeda, S., et al., "Construction and Identification of Bacterial Plasmids Containing Nucleotide Sequence for Human Leukocyte Interferon" *Proc. Natl. Acad. Sci. USA, 77*: 7010–7013 (1981).

Maher, P.A., et al., "Tyrosine Phosphorylated Proteins in Different Tissues During Chick Embryo Development", *J. Cell Biol., 106*: 1747–1755 (1988).

Maher, P.A., "Nerve Growth Factor Induces Protein–Tyrosine Phosphorylation", *Proc. Natl. Acad. Sci. U.S.A., 85*: 6788–6791 (1988).

Mariano, T.M., et al., The Mouse Immune Interferon Receptor Gene is Located On Chromosome 10*, *J. Biol. Chem., 262*: 5812–5814 (1987).

Marin et al, "Site Specificity of Casein Kinase–2(TS) from Rat Liver Cytosol: A Study with Model Peptide Substrates", *Eur. J. Biochem., 160*: 239–244 (1986).

Marston, AO., "The purification of eukaryotic polypeptides synthesized in *Escherichia coli*", *Biochem J., 240*: 1–12 (1986).

Messing, J., "New M13 Vectors for Cloning", *Methods In Anzymology, 101*: 20–78 (1983).

Meyer et al., "Identification and Procaryotic Expression of the Gene Coding for the Highly Immunogenic 28–Kilodalton Structural Phosphoprotein (pp28) of Human Cytomegalovirus", *J. Virol, 62(7)*: 2243–2250 (1988).

Mitrani–Rosenbaum, S., et al., "Inducible Expression of the Human Interferon β1 Gene Linked to a Bovine Papilloma Virus DNA Vector and Maintained Extrachromosomally in Mouse Cells", *Mol. Cell. Biol., 3*: 233–240 (1983).

Mogensen, K.E., et al., "Radioiodination of Human Alpha Interferons by the Chloramine T Method", *Method in Enzymol., 119*: 267–276 (1986).

Mogensen, K.E., et al., "Binding of $^{125}$I–Labelled Human αInterferon to Human Lymphoid Cells", *Int. J. Cancer, 28*, 575–582 (1981).

Morgan, J. R., et al., "Expression of an Exogenous Growth Hormone Gene by Transplantable Human Epidermal Cells", *Science, 237*: 1476–1479 (1987).

Morrison et al., "Genetically Engineered Antibdy Molecules; New Tools for Cancer Therapy", *Cancer Investigation, 6(2)*: 185–192 (1988).

Morrison, S.L., "New Approaches to the Production of Monoclonal Antibodies", *Science* 239 (4841 Pt 2): G28, G48, (1988).

Morrison, S.L. et al., "Genetically engineered antibody molecules and their application", *Ann N Y Acad Sci, 507*: 187–198 (1987).

Morrison, S.L et al., "Production of novel immunoglobulin molecules by gene transfection", *Mt. Sinai J. Med (NY)*, 53: 175–180 (1986).

Morse, D.E., et al., "Dynamics of Synthesis, Translation, and Degradation of trp Operon Messenger RNA in *E. coli*", *Cold Spring Harbor Symp. Quant. Biol., 34*, 725–740 (1970).

Moschera, J. A., et al., "Purification of Recombinant Human Fibroblast Interferon Produced in *Escherichia coli*", *Methods in Enzymol., 119*:177–183 (1986).

Mott, J.E., et al., "Maximizing Gene Expression from Plasmid Vectors Containing the λ $P_L$ Promoter: Strategies for Overproducing Transcription Termination Factor ", *Proc. Natl. Acad. Sci. U.S.A., 82*: 88–92 (1985).

Mulcahy, L., et al., "Use of Rous Sarcoma Viral Genome to Express Human Fibroblast Interferon", *Methods in Enzymol., 119*: 383–96 (1986).

Mulligan, R.C., et al., "Expression of a Bacterial Gene in Mammalian Cells", *Science, 209*: 1422–1427 (1980).

Pelech, LS et al., "Mitogen–activated S6 Kinase is Stimulated via Protein Kinase C–Dependent and Independent Pathways in Swiss 3T3 Cells", *J. Bio. Chem., 262(24)*: 11598–11606 (1987).

Pestka et al., "Interferons and their Actions", *Ann. Rev. Biochem., 56*: 727–777 (1987).

Pestka, S, et al., "The Human Interferons—from Protein Purification and Sequence to Cloning and Expression in Bacteria: Before, Between, and Beyond", *Arch. Biochem. And Biophys., 221* (1): 1–37 (1983).

Pestka, S., "Studies on Transfer Ribonucleic Acid–Ribosome Complexes", *J. Biol. Chem., 247*: 4669–4678 (1972).

Pestka, S., "Chapter 8: Sources of Interferon for Clinical Use: Preparation and Purification of Recombinant Interferons" in *Interferson 4: In vivo and Clinical Studies*, ed. N.B. Finter and R.K. Oldham, Elseview, New York: 107–120 (1985).

Pestka, S., "Interferon from 1981 to 1986", *Methods in Enzymol., 119*: 3–14 (1986).

Pleasure et al., "Site–Specific Phosphorylation of the Middle Molecular Weight Human Neurofilament Protein in Transfected Non–neuronal Cells", *J. Neurosci. 10l* (7): 2428–2437 (1990).

Rashidbaigi et al., "Characterization of Receptors for Immune Interferon in U937 Cells with $^{32}$ P–labeled Human Recombinant Immune Interferon*", *J. Bio. Chem. 260*: 8514–8519 (1985). Rashidbaigi, A. et al., "Characterization of Receptors for Immune Interferon in U937 Cells with 32P–labeled Human Recombinant Immune Interferon", J. Bio. Chem. 260 (14): 8514–8519 (1985).

Rashidbaigi, A., et al., "The Gene For The Human Immune Interferon Receptor Is Located On Chromosome 6", *Natl. Acad. Sci. USA, 83*: 384–388 (1986).

Rashidbaigi, A. et al., "Interferons: Protein Structure" in *The Interferon System: A Current Review to 1987* ed. S. Baron et al., University of Texas Press, Austin: 149–168 (1987).

Rees–Jones et al., "Insertional Mutagenesis of the Abelson Murine Leukemia Virus Genome: Identification of Mutants with Altered Kinase Activity and Defective Transformation Ability", J. Virol, 62(3):978–986 (1988).

Rehberg, E., et al., "Specific Molecular Activites of Recombinant and Hybrid Leukocyte Interferons*", J. Biol. Chem., 257: 11497–11502 (1982).

Remaut, E., et al., "Use of the Phage Lambda $P_L$ Promoter for High–Level Expression of Human Interferons in Escherichia coli", Methods in Enzymol., 119: 366–75 (1986).

Reznikoff, W.S. et al., "The lac Promoter" in "The Operon" ed. J.H. Miller et al., Cold Spring Harbor Laboratory: 221–243 (1980).

Robert–Galliot et al., "Phosphorylation of Recombinant Interferon–Gamma by Kinases Released From Various Cells", J. Gen. Virol., 66: 1439–1448 (1985).

Rosenberg, M, et al., "The Use of pKC30 and Its Derivatives for Controlled Expression of Genes", Methods in Enzymol., 101: 123–138 (1983).

Rossie, S et al., "Phosphorylation of the αSubunit of Rat Brain Sodium Channels by c–AMP–dependent Protein Kinase at a New Site Containing Ser–686 and Ser–687", J. Bio. Chem., 264(24): 14220–14224 (1989).

Sadowski, I et al., "Catalytic and non–catalytic domains of the Fujinami sarcoma virus P130 (gag–fps) protein–tyrosine kinase distinguished by the expression of v–fps polypeptides in Escherichia coli", Oncogene, 1: 181–191 (1987).

Sanger, F., et al., "DNA Sequencing With Chain–Terminating Inhibitors", Proc. Natl. Acad. Sci. U.S.A., 74: 5463–5467 (1977).

Sarkar, F.H., et al., "Radiolabeling of Human Leukocyte and Immune Interferons with $^{123}$I and Lactoperoxidase", Methods in Enzymol., 119: 263–267 (1986).

Scahill, S.J., et al., "Expression and Characterization of the Product of a Human Immune Interferon cDNA Gene in Chinese Hamster Ovary Cells", Proc. Natl. Acad. Sci. USA, 80: 4654–4658 (1983).

Schaber, M.D., et al., "Yeast Vectors for Production of Interferon", Methods in Enzymol., 119: 416–24 (1986).

Seki, J., et al., "Direct Identification of Phosphotyrosine–Containing Protein in Some Retrovirus–Transformed by Use of Anti–Phosphotyrosine Antibody", Cancer Res., 46: 907–916 (1986).

Shatzman, A.R., et al., "Efficient Expression of Heterologous Genes in Escherichia coli: The pAS Vector System and Its Applications", Ann. N.Y. Acad. Sci., 478:233–248 (1986).

Shatzman, A.R., et al., "Expression, Identification, and Characterization of Recombinant Gene Products in Escherichia coli", Methods in Enzymol., 152: 661–673 (1987).

Shuttleworth et al., "Expression of Interferon–α Genes in Human Lymphoblastoid (Namalwa) Cells", Eur. J. Biochem., 133: 399–404 (1983).

Simmons, D., et al., "The Fcγ Receptor of Natural Killer Cells is a Phospholipid–Linked Membrane Protein", Nature, 333: 568–570 (1988).

Simons, G., et al., High–Level Expression of Human Interferon Gamma in Escherichia coli Under Control of the PL Promoter of Bacteriophage Lambda†, Gene, 28: 55–64 (1984).

Smith, M. et al., "Constructed Mutants Using Synthetic Oligodeoxyribonucleotides as Site–specific Mutagens", Genetic Engineering, ed. J. Setlow and H. Hollaender, Plenum Press, NY, 3: 1–32 (1981).

Sommercorn, J et al., "Induction of Casein Kinase II During Differentiation of 3T3–L1 Cells", J. Bio. Chem., 262(8): 3839–3843 (1987).

Spencer, R.P. et al., eds., Radionuclides in Therapy, CRC Press, Boca Raton, Florida: 201 (1987).

Staehelin, T., et al., "Purification and Characterization of Recombinant Human Leukocyte Interferon (IFLrA) with Monoclonal Antibodies*", J. Biol. Chem., 256: 9750–9754 (1981).

Stamenkovic, I., et al., "Analysis of Two cDNA Clones Encoding the B Lymphocyte Antigen CD20 (B1, Bp35), A Type III Integral Membrane Protein", J Exp Med, 167: 1975–1980 (1988).

Sun, L.K. et al., "Chimeric antibodies with 17–1A–derived variable and human constant regions", Hybridoma, 5 Suppl 1: S17–20 (1986).

Sun. L.K., et al., "Chimeric Antibody With Human Constant Regions and Mouse Variable Regions Directed Against Carcinoma–Associated Antigen 17–1A", Proc Natl Acad Sco USA, 84: 214–218 (1987).

Taylor, S., "cAMP–dependent Protein Kinase: Model for an Enzyme Family", J. Bio. Chem., 264(15): 8443–8446 (1989).

Watt, R.A., et al., "Expression and Characterization of the Human c–myc DNA–Binding Protein", Molecular & Cellular Biology, 5: 448–456 (1985).

Wray, W., et al., "Silver Staining of Proteins in Polyacrylamide Gels", Anal. Biochem., 118: 197–203 (1981).

Xiaoxia, et al., Chinese J. Virol. 4: 189–193 (1988).

Yonehara, S., "Radioactive Human Lymphoblastoid Interferon: One–Step Purification, Regulation of Heterogeneous Specied Production and Its Use for Radioimmunoassay", Eur. J. Biochem. 125: 529–533 (1982).

Zetterquist, O., et al., "The Structural Requirements of Substrates of Cyclic AMP–Dependent Protein Kinase", FEBS Letters, 139: 287–290 (1982).

Zhao et al., "Cosntruction and Phosphorylation of a Fusion Protein Hu–IFN–αA/y", Analyt. Biochem. 178: 342–347 (1989).

Zhao, X–X. et al., "Expression of human interferon αH, and interferon with two potential asparagine–linked glycosylation sites", J. Biol. Reg. Homeo. Agents 1: 103–108 (1986).

Zimmerman, U.J., and Schlaepfer, W.W., "Clustering of Phosphorylated Amino Acid Residues In Neurofilament Proteins As Revealed by $^{31}$P NMR", Biochemistry, 25: 3533–3536 (1986).

Zinn, K., et al., "Regulated Expression of an Extrachromosomal Human β–Interferon Gene in Mouse Cells", Proc. Natl. Acad. Sci. USA, 79: 4897–4901 (1982).

Zoller et al., "Oligonucleotide–directed mutagenesis using M13–derived vectors: and efficient and general procedure for the production of point mutations in and fragment of DNA", Nucleic Acids Res. 11(20): 6487 (1982).

Zoon et al., "Purification and Characterization of Multiple Components of Human Lymphoblastoid Interferon–α", J. Bio. Chem., 267(21): 15210–15216 (1992).

Zoon, K.C., et al., "Procedures for Studying the Binding of Interferon to Human and Bovine Cells in Monolayer Culture", Method in Enzymol., 119: 312–315 (1986).

Zoon, K.C. et al., "Studies of the Interferon Receptors", *Pharmcol. Ther.* 24: 259–279 (1984).

Zoon, et al., "Specific Binding of Human α Interferon to a High Affinity Cell Surface Binding Site on Bovine Kidney Cells*", *J. Biol. Chem., 257:* 4695–4697 (1982).

Zur Nedden, D.L., et al., "Radiolabeling of Human Interferon Alphas with $^{125}$I–Labeled Bolton–Hunter Reagent", *Methods in Enzymol., 119:* 276–281 (1986).

\* cited by examiner

```
5'           1
    MET CYS ASP LEU PRO GLN THR HIS SER LEU GLY SER ARG ARG THR LEU MET LEU ALA GLN MET ARG LYS ILE
    ATG TGT GAT CTG CCT CAA ACC CAC AGC CTG GGT AGC AGG AGG ACC TTG ATG CTG GCA CAG ATG AGG AAA ATC

SER LEU PHE SER CYS LEU LYS ASP ARG HIS ASP PHE GLY PHE PRO GLN GLU GLU PHE GLY ASN GLN PHE GLN LYS
    TCT CTT TTC TCC TGC TTG AAG GAC AGA CAT GAC TTT GGA TTT CCC CAG GAG GAG TTT GGC AAC CAG TTC CAA AAG 50                                                              70
    ALA GLU THR ILE PRO VAL LEU HIS GLU MET ILE GLN GLN ILE PHE ASN LEU PHE SER THR LYS ASP SER SER ALA
    GCT GAA ACC ATC CCT GTC CTC CAT GAG ATG ATC CAG CAG ATC TTC AAT CTC TTC AGC ACA AAG GAC TCA TCT GCT

ALA TRP ASP GLU THR LEU LEU ASP LYS PHE TYR THR GLU LEU TYR GLN GLN LEU ASN ASP LEU GLU ALA CYS VAL
    GCT TGG GAT GAG ACC CTC CTA GAC AAA TTC TAC ACT GAA CTC TAC CAG CAG CTG AAT GAC CTG GAA GCC TGT GTG 100                                                             120
    ILE GLN GLY VAL GLY VAL THR GLU THR PRO LEU MET LYS GLU ASP SER ILE LEU ALA VAL ARG LYS TYR PHE GLN
    ATA CAG GGG GTG GTG ACT CCC CTG ATG AAG GAG GAC TCC ATT CTG GCT GTG AGG AAA TAC TTC CAA

ARG ILE THR LEU TYR LEU LYS GLU LYS LYS TYR SER PRO CYS ALA TRP GLU VAL VAL ARG ALA GLU ILE MET ARG
    AGA ATC ACT CTC TAT CTG AAA GAG AAG AAA TAC AGC CCT TGT GCC TGG GAG GTT GTC AGA GCA GAA ATC ATG AGA 150                                            165 166                              170
    SER PHE SER LEU SER THR ASN LEU GLN GLU SER LEU ARG SER LYS GLU LYS ARG LYS ARG SER GLN MET LEU PHE
    TCT TTT TCT TTG TCA ACA AAC TTG CAA GAA AGT TTA AGA AGT AAG GAA AAG CGA AAG AGG AGT CAG ATG CTG TTT 180 181
    GLN GLY ARG ARG ALA SER GLN END
    CAA GGT CGA AGA GCA TCC CAG TAA TGGTTGTCTCCTGCCTGCAATATTTG 3'
```

Fig. 3

COMPARISON OF NUCLEOTIDE AND AMINO ACID SEQUENCES OF
Hu-IFN-αA AND ANALOGUES WITH PHOSPHORYLATION SITES

```
                155              160              165
αA      5'...ACA AAC TTG CAA GAA AGT TTA AGA AGT AAG GAA TGA
           Thr Asn Leu Gln Glu Ser Leu Arg Ser Lys Glu END 155              160              165              170
αA-P1   5'...ACA AAC TTG CAA GAA AGT TTA AGA AGT AAG AGA AGG GCA AGT GTT GCA TGA
           Thr Asn Leu Gln Glu Ser Leu Arg Ser Lys|Arg Arg Ala Ser Val|Ala END 155              160              165  167
αA-P2   5'...ACA AAC TTG CAA AGA AGT TTA AGA AGG GCA AGT TTA GCA TGA
           Thr Asn Leu Gln Arg Ser Leu Arg|Arg Arg Ala Ser Leu|Ala END 155              160              165              170              175              180  182
αA-P3   5'...ACA AAC TTG CAA GAA AGT TTA AGA AGT AGA GAA GGG CAA GTG TTG CAT GAA AGT TTA AGA AGT AAG AGA AGG GCA AGT GTT GCA TGA
           Thr Asn Leu Gln Glu Ser Leu Arg Ser Arg Glu Gly Gln Val Leu His Glu Ser Leu Arg Ser Lys|Arg Arg Ala Ser Val|Ala END
```

Fig. 8

SEQUENCE LISTING

<160> NUMBER OF SEQ ID NOS: 38

<210> SEQ ID NO 1
<211> LENGTH: 4
<212> TYPE: PRT
<213> ORGANISM: Artificial Sequence
<220> FEATURE:
<223> OTHER INFORMATION: recognition sequence

<400> SEQUENCE: 1

```
Arg Arg Ala Ser
1

<210> SEQ ID NO 2
<211> LENGTH: 5
<212> TYPE: PRT
<213> ORGANISM: Artificial Sequence
<220> FEATURE:
<223> OTHER INFORMATION: recognition sequence

<400> SEQUENCE: 2

Arg Arg Ala Ser Val
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Arg Thr Lys Arg Ser Gly Ser Val
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic peptide

<400> SEQUENCE: 4

Arg Lys Arg Ser Arg Lys Glu
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Xaa=hydroxyproline

<400> SEQUENCE: 5

Leu Arg Arg Ala Xaa Leu Gly
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic peptide

<400> SEQUENCE: 6

Ser Glu Glu Glu Glu Glu
1               5

<210> SEQ ID NO 7
<211> LENGTH: 10
<212> TYPE: PRT
<213> ORGANISM: Artificial Sequence
<220> FEATURE:
<223> OTHER INFORMATION: casein kinase II substrate
```

```
<400> SEQUENCE: 7

Arg Arg Arg Glu Glu Glu Thr Glu Glu Glu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: casein kinase II substrate

<400> SEQUENCE: 8

Arg Arg Arg Glu Glu Glu Ser Glu Glu Glu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: casein kinase II substrate

<400> SEQUENCE: 9

Arg Arg Arg Asp Asp Asp Ser Asp Asp Asp
1               5                   10

<210> SEQ ID NO 10
<211> LENGTH: 10
<212> TYPE: PRT
<213> ORGANISM: Artificial Sequence
<220> FEATURE:
<223> OTHER INFORMATION: casein kinase II substrate

<400> SEQUENCE: 10

Arg Arg Arg Glu Glu Glu Ser Glu Glu Glu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: casein kinase II substrate
<220> FEATURE:
<221> NAME/KEY: MISC_FEATURE
<222> LOCATION: (7)..(7)
<223> OTHER INFORMATION: Xaa=Ser or Thr

<400> SEQUENCE: 11

Ala Ala Ala Ala Ala Ala Xaa Glu Glu Glu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: casein kinase II substrate
<220> FEATURE:
<221> NAME/KEY: MISC_FEATURE
<222> LOCATION: (7)..(7)
<223> OTHER INFORMATION: Xaa=Ser or Thr

<400> SEQUENCE: 12

Ala Ala Ala Glu Glu Glu Xaa Glu Glu Glu
1               5                   10
```

<210> SEQ ID NO 13
<211> LENGTH: 8
<212> TYPE: PRT
<213> ORGANISM: Artificial Sequence
<220> FEATURE:
<223> OTHER INFORMATION: synthetic peptide

<400> SEQUENCE: 13

Arg Arg Leu Ser Ser Leu Arg Ala
1               5

<210> SEQ ID NO 14
<211> LENGTH: 9
<212> TYPE: PRT
<213> ORGANISM: Artificial Sequence
<220> FEATURE:
<223> OTHER INFORMATION: synthetic peptide

<400> SEQUENCE: 14

Thr Glu Thr Ser Gln Val Ala Pro Ala
1               5

<210> SEQ ID NO 15
<211> LENGTH: 43
<212> TYPE: DNA
<213> ORGANISM: Artificial Sequence
<220> FEATURE:
<223> OTHER INFORMATION: oligonucleotide used for directing deletion
<220> FEATURE:
<221> NAME/KEY: CDS
<222> LOCATION: (2)..(43)
<223> OTHER INFORMATION:

<400> SEQUENCE: 15 a gaa agt tta aga agt aag gaa aag cga aaa agg agt cag atg        43
  Glu Ser Leu Arg Ser Lys Glu Lys Arg Lys Arg Ser Gln Met
  1               5                  10

<210> SEQ ID NO 16
<211> LENGTH: 14
<212> TYPE: PRT
<213> ORGANISM: Artificial Sequence
<220> FEATURE:
<223> OTHER INFORMATION: gamma fusion protein

<400> SEQUENCE: 16

Glu Ser Leu Arg Ser Lys Glu Lys Arg Lys Arg Ser Gln Met
1               5                  10

<210> SEQ ID NO 17
<211> LENGTH: 572
<212> TYPE: DNA
<213> ORGANISM: Artificial Sequence
<220> FEATURE:
<223> OTHER INFORMATION: synthetic DNA for fusion protein
<220> FEATURE:
<221> NAME/KEY: CDS
<222> LOCATION: (4)..(546)
<223> OTHER INFORMATION:

<400> SEQUENCE: 17 atg tgt gat ctg cct caa acc cac agc ctg ggt agc agg agg acc ttg    48
    Cys Asp Leu Pro Gln Thr His Ser Leu Gly Ser Arg Arg Thr Leu
    1               5                  10                  15 atg ctc ctg gca cag atg agg aaa atc tct ctt ttc tcc tgc ttg aag    96
Met Leu Leu Ala Gln Met Arg Lys Ile Ser Leu Phe Ser Cys Leu Lys
                20                  25                  30

```
gac aga cat gac ttt gga ttt ccc cag gag gag ttt ggc aac cag ttc      144
Asp Arg His Asp Phe Gly Phe Pro Gln Glu Glu Phe Gly Asn Gln Phe
             35                  40                  45 caa aag gct gaa acc atc cct gtc ctc cat gag atg atc cag cag atc      192
Gln Lys Ala Glu Thr Ile Pro Val Leu His Glu Met Ile Gln Gln Ile
     50                  55                  60 ttc aat ctc ttc agc aca aag gac tca tct gct gct tgg gat gag acc      240
Phe Asn Leu Phe Ser Thr Lys Asp Ser Ser Ala Ala Trp Asp Glu Thr
 65                  70                  75 ctc cta gac aaa ttc tac act gaa ctc tac cag cag ctg aat gac ctg      288
Leu Leu Asp Lys Phe Tyr Thr Glu Leu Tyr Gln Gln Leu Asn Asp Leu
 80                  85                  90                  95 gaa gcc tgt gtg ata cag ggg gtg ggg gtg aca gag act ccc ctg atg      336
Glu Ala Cys Val Ile Gln Gly Val Gly Val Thr Glu Thr Pro Leu Met
                 100                 105                 110 aag gag gac tcc att ctg gct gtg agg aaa tac ttc caa aga atc act      384
Lys Glu Asp Ser Ile Leu Ala Val Arg Lys Tyr Phe Gln Arg Ile Thr
                 115                 120                 125 ctc tat ctg aaa gag aag aaa tac agc cct tgt gcc tgg gag gtt gtc      432
Leu Tyr Leu Lys Glu Lys Lys Tyr Ser Pro Cys Ala Trp Glu Val Val
             130                 135                 140 aga gca gaa atc atg aga tct ttt tct ttg tca aca aac ttg caa gaa      480
Arg Ala Glu Ile Met Arg Ser Phe Ser Leu Ser Thr Asn Leu Gln Glu
 145                 150                 155 agt tta aga agt aag gaa aag cga aaa agg agt cag atg ctg ttt caa      528
Ser Leu Arg Ser Lys Glu Lys Arg Lys Arg Ser Gln Met Leu Phe Gln
 160                 165                 170                 175 ggt cga aga gca tcc cag taatggttgt cctgcctgca atattg                 572
Gly Arg Arg Ala Ser Gln
                 180
```

<210> SEQ ID NO 18
<211> LENGTH: 181
<212> TYPE: PRT
<213> ORGANISM: Artificial Sequence
<220> FEATURE:
<223> OTHER INFORMATION: gamma fusion protein

<400> SEQUENCE: 18

```
Cys Asp Leu Pro Gln Thr His Ser Leu Gly Ser Arg Arg Thr Leu Met
 1               5                  10                  15

Leu Leu Ala Gln Met Arg Lys Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
             100                 105                 110

Glu Asp Ser Ile Leu Ala Val Arg Lys Tyr Phe Gln Arg Ile Thr Leu
         115                 120                 125

Tyr Leu Lys Glu Lys Lys Tyr Ser Pro Cys Ala Trp Glu Val Val Arg
     130                 135                 140

Ala Glu Ile Met Arg Ser Phe Ser Leu Ser Thr Asn Leu Gln Glu Ser
145                 150                 155                 160
```

Leu Arg Ser Lys Glu Lys Arg Lys Arg Ser Gln Met Leu Phe Gln Gly
                165                 170                 175

Arg Arg Ala Ser Gln
            180

<210> SEQ ID NO 19
<211> LENGTH: 36
<212> TYPE: DNA
<213> ORGANISM: Homo sapiens
<220> FEATURE:
<221> NAME/KEY: CDS
<222> LOCATION: (1)..(36)
<223> OTHER INFORMATION:

<400> SEQUENCE: 19 aca aac ttg caa gaa agt tta aga agt aag gaa tga                    36
Thr Asn Leu Gln Glu Ser Leu Arg Ser Lys Glu
1               5                   10

<210> SEQ ID NO 20
<211> LENGTH: 11
<212> TYPE: PRT
<213> ORGANISM: Homo sapiens

<400> SEQUENCE: 20

Thr Asn Leu Gln Glu Ser Leu Arg Ser Lys Glu
1               5                   10

<210> SEQ ID NO 21
<211> LENGTH: 51
<212> TYPE: DNA
<213> ORGANISM: Homo sapiens
<220> FEATURE:
<221> NAME/KEY: CDS
<222> LOCATION: (1)..(51)
<223> OTHER INFORMATION:

<400> SEQUENCE: 21 aca aac ttg caa gaa agt tta aga agt aag aga agg gca agt gtt gca    48
Thr Asn Leu Gln Glu Ser Leu Arg Ser Lys Arg Arg Ala Ser Val Ala
1               5                   10                  15 tga                                                                51

<210> SEQ ID NO 22
<211> LENGTH: 16
<212> TYPE: PRT
<213> ORGANISM: Homo sapiens

<400> SEQUENCE: 22

Thr Asn Leu Gln Glu Ser Leu Arg Ser Lys Arg Arg Ala Ser Val Ala
1               5                   10                  15

<210> SEQ ID NO 23
<211> LENGTH: 42
<212> TYPE: DNA
<213> ORGANISM: Homo sapiens
<220> FEATURE:
<221> NAME/KEY: CDS
<222> LOCATION: (1)..(42)
<223> OTHER INFORMATION:

<400> SEQUENCE: 23 aca aac ttg caa aga agt tta aga agg gca agt tta gca tga            42
Thr Asn Leu Gln Arg Ser Leu Arg Arg Ala Ser Leu Ala
1               5                   10

```
<210> SEQ ID NO 24
<211> LENGTH: 13
<212> TYPE: PRT
<213> ORGANISM: Homo sapiens

<400> SEQUENCE: 24

Thr Asn Leu Gln Arg Ser Leu Arg Arg Ala Ser Leu Ala
1               5                   10

<210> SEQ ID NO 25
<211> LENGTH: 87
<212> TYPE: DNA
<213> ORGANISM: Homo sapiens
<220> FEATURE:
<221> NAME/KEY: CDS
<222> LOCATION: (1)..(87)
<223> OTHER INFORMATION:

<400> SEQUENCE: 25 aca aac ttg caa gaa agt tta aga agt aga gaa ggg caa gtg ttg cat         48
Thr Asn Leu Gln Glu Ser Leu Arg Ser Arg Glu Gly Gln Val Leu His
1               5                   10                  15 gaa agt tta aga agt aag aga agg gca agt gtt gca tga                     87
Glu Ser Leu Arg Ser Lys Arg Arg Ala Ser Val Ala
            20                  25

<210> SEQ ID NO 26
<211> LENGTH: 28
<212> TYPE: PRT
<213> ORGANISM: Homo sapiens

<400> SEQUENCE: 26

Thr Asn Leu Gln Glu Ser Leu Arg Ser Arg Glu Gly Gln Val Leu His
1               5                   10                  15

Glu Ser Leu Arg Ser Lys Arg Arg Ala Ser Val Ala
            20                  25

<210> SEQ ID NO 27
<211> LENGTH: 5
<212> TYPE: PRT
<213> ORGANISM: Artificial Sequence
<220> FEATURE:
<223> OTHER INFORMATION: recognition sequence

<400> SEQUENCE: 27

Arg Arg Ala Ser Leu
1               5

<210> SEQ ID NO 28
<211> LENGTH: 6
<212> TYPE: PRT
<213> ORGANISM: Artificial Sequence
<220> FEATURE:
<223> OTHER INFORMATION: recognition sequence

<400> SEQUENCE: 28

Arg Arg Ala Ser Val Ala
1               5

<210> SEQ ID NO 29
<211> LENGTH: 48
<212> TYPE: DNA
<213> ORGANISM: Artificial Sequence
<220> FEATURE:
<223> OTHER INFORMATION: oligonucleotide used to prepare Hu-IFN-P1
```

```
<400> SEQUENCE: 29
agtttaagaa gtaagagaag ggcaagtgtt gcatgaaaac tgcttcaa                    48

<210> SEQ ID NO 30
<211> LENGTH: 54
<212> TYPE: DNA
<213> ORGANISM: Artificial Sequence
<220> FEATURE:
<223> OTHER INFORMATION: oligonucleotide used to prepare Hu-IFN-P2

<400> SEQUENCE: 30
acaaacttgc aaagaagttt aagaagggca agtttagcat gaaaactgct tcaa             54

<210> SEQ ID NO 31
<211> LENGTH: 11
<212> TYPE: DNA
<213> ORGANISM: Homo sapiens

<400> SEQUENCE: 31
aactggttca a                                                            11

<210> SEQ ID NO 32
<211> LENGTH: 26
<212> TYPE: DNA
<213> ORGANISM: Artificial Sequence
<220> FEATURE:
<223> OTHER INFORMATION: BglII-XmaI linker

<400> SEQUENCE: 32
gatctgcgcg cgcacgcgcg cgggcc                                            26

<210> SEQ ID NO 33
<211> LENGTH: 53
<212> TYPE: DNA
<213> ORGANISM: Artificial Sequence
<220> FEATURE:
<223> OTHER INFORMATION: oligonucleotide to construct coding sequence of
      Hu-IFN

<400> SEQUENCE: 33
cttacaggtt acctccgaag ggcaagtgtt gcatgaagat tgcgcgcgcc cgg              53

<210> SEQ ID NO 34
<211> LENGTH: 24
<212> TYPE: DNA
<213> ORGANISM: Homo sapiens
<220> FEATURE:
<221> NAME/KEY: CDS
<222> LOCATION: (1)..(24)
<223> OTHER INFORMATION:

<400> SEQUENCE: 34 ctt aca ggt tac ctc cga aac tga                                         24
Leu Thr Gly Tyr Leu Arg Asn
1               5

<210> SEQ ID NO 35
<211> LENGTH: 7
<212> TYPE: PRT
<213> ORGANISM: Homo sapiens

<400> SEQUENCE: 35

Leu Thr Gly Tyr Leu Arg Asn
1               5
```

```
<210> SEQ ID NO 36
<211> LENGTH: 36
<212> TYPE: DNA
<213> ORGANISM: Homo sapiens
<220> FEATURE:
<221> NAME/KEY: CDS
<222> LOCATION: (1)..(36)
<223> OTHER INFORMATION:

<400> SEQUENCE: 36 ctt aca ggt tac ctc cga agg gca agt gtt gca tga                          36
Leu Thr Gly Tyr Leu Arg Arg Ala Ser Val Ala
1               5                   10

<210> SEQ ID NO 37
<211> LENGTH: 11
<212> TYPE: PRT
<213> ORGANISM: Homo sapiens

<400> SEQUENCE: 37

Leu Thr Gly Tyr Leu Arg Arg Ala Ser Val Ala
1               5                   10

<210> SEQ ID NO 38
<211> LENGTH: 34
<212> TYPE: DNA
<213> ORGANISM: Artificial Sequence
<220> FEATURE:
<223> OTHER INFORMATION: sequence for oligonucleotide-directed
      mutagenesis and hybridization screening

<400> SEQUENCE: 38
ctgactcctt tttcgctttt ccttacttct taac                                    34
```

NUCLEIC ACIDS ENCODING PHOSPHORYLATED FUSION PROTEINS

RELATED APPLICATIONS

This application is a continuation of U.S. patent application Ser. No. 09/246,830 filed Feb. 8, 1999, now U.S. Pat. No. 6,514,753 which is a continuation of U.S. patent application Ser. No. 08/487,057 filed Jun. 7, 1995, now U.S. Pat. No. 6,150,503 the entire contents of which are hereby incorporated by reference.

FIELD OF THE INVENTION

The present invention relates to the field of recombinant DNA technology, to means, methods of utilizing this technology to synthesize useful functional proteins or polypeptides which include one or more phosphate (or thiophosphate) groups which are radio-labelled, to these and various other products useful in biomedical, medical, biochemical applications including diagnostics, prophylatics and therapeutics.

More specifically the invention relates to new interferons, especially to leukocyte, or alpha interferon(s) and fibroblast or beta interferon which contain one or more radioactive phosphorylated groups, to DNA sequences encoding putative phosphorylatable sites, which code for these new interferons.

BACKGROUND OF THE INVENTION

Radio-labelled proteins have numerous medical, biological, clinical, scientific and other applications. Interferons, specifically, labelled with $^{125}$I have been used for binding and crosslinking studies (1, 17, 27–32, 34–37).[1] Human IFN-α's, -β, and -gamma have all been radio-iodinated by various procedures (reviewed in Pestka et al (2)). However, proteins labelled with radioactive iodine have serious well-known disadvantages and hazards.

[1]The scientific publications, patents or other literature ("publications") to which reference is made herein are referenced by numerals and identified further towards the end of this text.

All of these publications are incorporated herein by reference.

The study of cell surface receptors for the interferons requires radio-labelled interferons, such as interferons labelled with $^{125}$I, with high biological and high radio-specific activity. Several years ago, it was found that interferon gamma[2] can be phosphorylated to very high radio-specific activity while retaining biological activity (3, 4). Thus, [$^{12}$P]Hu- and Mu-IFN-gamma were used for studying the human and murine IFN-gamma receptors, respectively (5, 6, 9). These studies were carried out by phosphorylating human and murine interferon gamma (Hu- and Mu-IFN-gamma) with cyclic AMP-dependent protein kinase from bovine heart muscle and [gamma-$^{32}$P]ATP (3). These phosphorylated and $^{12}$P-labelled interferons have provided valuable reagents (3, 4) of high radio-specificity to study cell surface receptors (5, 6) and to identify the chromosome encoding the gene for Hu-IFN-gamma (7, 8) and Mu-IFN-gamma (9) receptors. For all of these studies and applications, interferons which are phosphorylated are most useful. Several reports identified the phosphorylation sites of Hu- and Mu-IFN-gamma as serine residues near the COOH termini (4, 5, 10, 11).

[2]The abbreviations used have followed standard nomenclature as described in detail in Methods of Enzymology, Interferons, Vol. 119, Part C, Edited by Sidney Pestka, Section I, Introduction (Reference 25). In brief, interferon alpha, beta, and gamma are designated IFN-α, IFN-β, and -gamma, respectively. The species of origin is designated by a prefix Hu, Mu, Bo, etc. for human, murine, or bovine species, respectively, as Hu-IFN-α, Hu-IFN-β, or Hu-IFN-gamma, for example.

However, under conditions used for the phosphorylation of IFN-gamma, it was reported that Hu-IFN-αA and Hu-IFN-β cannot be phosphorylated by the cyclic AMP (cAMP)-dependent protein kinase (2, 3). A review of the phosphorylation of the various classes or groups of interferons and other proteins (1, 3, 4, 20, 21, 22, 38, 39, 40, 64) confirms that researchers have not successfully phosphorylated Hu-IFN-α or Hu-IFN-β under conditions under which gamma interferons have been phosphorylated. It has been reported indeed that recombinant IFN-α and IFN-β were not phosphorylated (3) and as a consequence it was uncertain whether an available site was present.

In the light of problems with iodinated compounds and limitations for use of iodinated IFN-gamma, it is understandable that there is a keen interest and need in making available phosphorylated Hu-IFN-α and -β which can be labelled for numerous practical, scientific and commercial applications.

Likewise, there is such interest and need for other phosphorylated—and labelled—polypeptides which are not available yet in such chemical configurations. For example, a phosphorylatable tumor necrosis factor (TNF) would be valuable to study the receptor for TNF. TNF is not phosphorylatable with the cAMP-dependent bovine heart kinase. Indeed, it has been reported that interest in protein phosphorylation has increased enormously over the past few years (38, 39).

The invention as will be described in detail hereinafter contributes to meeting these and other needs.

By way of further background to the invention, the term "interferon" describes a family of animal proteins which possess antiviral, antiproliferative and other potentially useful properties. There appear to be three major classes of interferons: leukocyte (or alpha interferon), fibroblast (or beta interferon) and immune (or gamma interferon) (1, 2). Detailed description of interferons is found in various publications including in references 1, 2, U.S. Pat. Nos. 4,727,138; 4,734,491; 4,737,462, and many others; various hybrid human leukocyte interferons are described in U.S. Pat. No. 4,414,150 and in reference 46. In general the standard class of human IFN-α's are polypeptides of 165–166 amino acids (see reference 1 for details of human and non-human interferon-α species); some species have been isolated that lack the 10 COCH-terminal amino acid residues; and some species of IFN-A are glycosylated. The amino acid sequences of Hu-IFN-α species and of Hu-IFN-β derived from cDNA or genomic DNA sequences are described in (1, Section I). Recombinant DNA-derived interferons including Hu-IFN-α, -β, and -gamma and corresponding interferons from other animal species are likewise well described (1, 2). Various modifications of human and murine interferons have been reported. New non-natural human and murine interferons with often markedly changed biological properties have been constructed (1, 24, 45). The terminology "non-natural" is a term of art which refers to recombinant DNA interferons obtained by altering the nucleotide sequence of coding cDNAs (45).

The term "Hu-IFN-α" as used herein is intended to include all different species of alpha interferons. A large number of DNA sequences corresponding to the interferons from various species have been isolated and identified. Likewise various IFN-βs and IFN-gamma(s) are disclosed. The invention encompasses all of these members of the family (reference 1, pages 5–14).

The term "native" as used herein refers to the proteins, e.g., interferons, which proteins are naturally produced;

"synthetic" and "non-natural" refers to proteins produced by synthetic or DNA-recombinant procedures, either type which do not contain a phosphorylatable site (or where the phosphorylatable site is inaccessible, for instance due to the configuration of the protein), which protein in accordance with the invention is to be phosphorylated.

This invention contemplates and includes all interferons native, natural, modified, or recombinant DNA interferon-like proteins which are modifiable by introduction of one or more phosphate or analog groups. All of these interferons and others known in the art or to be known are within the contemplation of the invention. The present invention is principally concerned with various modified proteins or polypeptides, and alpha and beta interferons.

When reference is made to IFN-alpha, the term is intended to cover and include the various alpha species.

The term "modified" is used in this invention broadly, and means for instance, when reference is made to proteins, a protein which has been provided with a phosphorylatable site or provided with a phosphorus label (or analog label). The nucleotide sequences which code for such amino acid sequences which contain a putative phosphorylation site are also designated as "modified", when appropriate.

The term "unphosphorylatable" protein means a protein which normally has not been phosphorylatable (or phosphorylated) for whatever reason, e.g., either because it does not contain a putative phosphorylatable site and correspondingly, the DNA sequence which codes for the protein does not contain the DNA sequence coding for the putative amino acid recognition sequence; or because such site is not accessible for phosphorylation.

The term "provided with" or "having provision(s) for" or like terminology is used in this invention broadly, and means both "fused" and "inserted". Illustrative are the hybrid-fused Hu-IFN-αA/gamma (illustrated in FIG. 1) and Hu-IFN-αA-P1, -P2 and -P3 (illustrated in FIG. 8), respectively. Thus, the nucleotide insert can be within the coding region of the gene at one end thereof or anywhere within the coding region. These variants are all considered to be within the term "modified," which can refer to the amino acid sequence or to the nucleotide sequences, as will become apparent from the description hereinafter.

The term "comprises" or "comprising" covers and includes all situations regardless where the amino acid recognition sequence (or the nucleotide sequence coding for it) is located.

By way of further background in the preferred method of the invention, phosphorylation is carried out by means of a protein kinase. Protein kinases catalyze the transfer of the gamma phosphoryl group of ATP to an acceptor protein substrate. However, as described herein the invention is not limited to kinases for which the acceptor site is a particular amino acid (like serine) but includes also those for which the site is another amino acid in the sequence, and in general includes protein kinases as a whole.

The term "protein" (or polypeptide) as used herein is intended to include glycoproteins (as well as proteins having other additions). A case in point is that of natural Hu-IFN-β which has been shown to be a glycoprotein; when produced in E. coli by recombinant DNA techniques, Hu-IFN-β is not glycosylated. Glycosylated interferons have been reported to be obtained by expressing the proteins in animal cells or in yeast (as is discussed in reference 1 at pps. 383–433 and 453–464; and in references 48–55, 84–92).

The term "biological activities" or like terms as used herein in conjunction with proteins is intended to be interpreted broadly. In the case of the interferon-like proteins, it includes all known (or to be discovered) properties including properties specific to Hu-IFN-α's or to Hu-IFN-β or common to both, such as their antiviral activity and their capability to modulate antigens of the major histocompatibility complex (MHC), in particular to induce an increase in surface expression of class I MHC antigens, including $\beta_2$-macroglobulin.

"Functional" proteins are proteins which have a biological or other activity or use.

The term "active areas" or "biologically active" areas or segments or equivalent terminology often refers to the presence of a particular conformation or folding of the protein molecule, or for instance, to specific disulfide bridges between specific amino acids in the sequence, but of course is not limited thereto.

The term "vector" as used herein means a plasmid, a phage DNA, or other DNA sequence that (1) is able to replicate in a host cell, (2) is able to transform a host cell, and (3) contains a marker suitable for identifying transformed cells.

Throughout the description of the invention and the claims, and following convention, the "singular" includes the "plural"; for instance, a phosphorylatable or phosphorylation site, means at least one such site, unless indicated otherwise.

Other terminology used herein will become apparent from the description which follows.

BRIEF DESCRIPTION OF THE PRIOR ART

Background references for the subject invention are referred to within the body and towards the end of the text.

As representative of United States patents which relate to interferon, the following may be mentioned:

U.S. Pat. No. 4,503,035 to Pestka et al relates to human leukocyte interferon as a homogeneous protein species, such as species $\alpha_1$, $\alpha_2$, and $\beta_1$, and others. For a discussion of terminology of natural and recombinant interferons see references 1 (pps. 3–23), 24, 102, and 103 (footnote p. 112 and text);

U.S. Pat. No. 4,748,233 to Sloma relates to a cloned human alpha interferon GX-1 gene which specifies the synthesis of alpha interferon GX-1;

U.S. Pat. No. 4,746,608 to Mizukami et al relates to a process for producing peptides generally such as interferon and in particular beta interferon with microorganisms containing recombinant DNA;

U.S. Pat. No. 4,738,931 to Sugano et al relates to a DNA sequence containing a human interferon-β gene and the production of human interferon-β in eukaryotes;

U.S. Pat. No. 4,738,921 to Belagaje et al relates to a recombinant DNA expression vector and a process for producing peptides generally including interferon. The recombinant DNA vector comprises a derivative of the tryptophan promoter-operator-leader sequence useful for the expression;

U.S. Pat. No. 4,737,462 to Mark et al relates to modified interferon-β wherein the cysteine residue at position 17 is substituted by serine. In connection with that patent, it is interesting to note that the Ser which is provided in replacement of the Cys 17 does not constitute part of the amino acid sequence recognizable by the cAMP-dependent kinase, as described in connection with the present invention;

U.S. Pat. No. 4,734,491 to Caruthers relates to a DNA sequence and a method for the construction of recombinant DNA sequences which encode hybrid lymphoblastoid-leukocyte human interferons which have biological or immunological activity;

U.S. Pat. No. 4,727,138 to Goeddel et al relates to recombinant DNA for encoding polypeptides specifically human immune interferon (interferon gamma);

U.S. Pat. No. 4,705,750 to Nasakazu et al relates to recombinant DNA having promoter activity and a process for the production of peptides including human immune interferon by a transformed bacillus;

U.S. Pat. No. 4,681,931 to Obermeier et al relates to a process for the isolation and purification of alpha interferons;

U.S. Pat. No. 4,659,570 to Terano relates to a stabilized physiologically active polypeptide especially gamma interferon;

U.S. Pat. No. 4,559,302 to Ingolia relates to DNA sequences which encode various functional polypeptides including human interferon;

U.S. Pat. No. 4,559,300 to Kovacevic et al relates to a method for producing functional polypeptides including human interferon in a streptomyces host cell and transformed bacillus;

U.S. Pat. No. 4,530,904 to Hershberger et al relates to a method for protecting a bacterium transformed with recombinant DNA that can produce functional polypeptides such as human interferon and non-human interferon from bacteriophage activity;

U.S. Pat. No. 4,506,013 to Hershberger et al relates to a method for stabilizing and selecting recombinant DNA host cells which produce functional polypeptides generally including human and non-human interferon, and the transformed host cells;

U.S. Pat. No. 4,436,815 to Hershberger et al relates to a similar method and product;

U.S. Pat. No. 4,420,398 to Castino relates to a purification method for human interferon;

U.S. Pat. No. 4,262,090 to Colby, Jr. et al relates to a method for producing mRNA for mammalian interferon;

U.S. Pat. No. 4,751,077 to Bell et al relates to a modified human interferon-beta in which tyrosine is replaced by cysteine. The modified interferon has improved stability;

U.S. Pat. No. 4,748,234 to Dorin et al relates to a process for recovering and removing biologically active proteins specifically human interferon-$\beta$ from a genetically engineered host microorganism cell;

U.S. Pat. No. 4,748,119 to Rich et al relates to a process of in vitro site-directed mutagenesis or DNA deletion/substitution of DNA segments which results in DNA segments capable of enhanced expression and production of polypeptides in general including interferons;

U.S. Pat. No. 4,745,057 to Beckage et al relates to a process in which transformed yeast cells express biologically-active polypeptides in general including human and non-human interferon;

U.S. Pat. No. 4,745,053 to Mitsuhashi relates to a process for inducing the production of human interferon from whole blood and for measuring blood interferon productivity level and a clinical assay for cancer; p U.S. Pat. No. 4,743,445 to Delwiche et al relates to a method for treating (hemorrhagic) thrombocythemia by using alpha-type interferons;

U.S. Pat. No. 4,741,901 to Levinson et al relates to recombinant DNA technology to produce polypeptides generally including human fibroblast and human and hybrid leukocyte interferons;

U.S. Pat. No. 4,738,928 to Weissmann et al relates to a method for identifying and isolating a recombinant DNA segment coding for a polypeptide, and cloning the said DNA segment.

It is noteworthy that the above reviewed patent literature does not address or disclose human interferons which have phosphorylated groups (or isotopes thereof).

SUMMARY AND GENERAL CONCEPTS OF THE INVENTION

In a broad sense, the invention contemplates labellable and labelled proteins, e.g. radio-labellable and radio-labelled proteins, and DNA and CDNA molecules encoding the radio-labellable proteins.

The invention encompasses recombinant DNA sequences which encode functional proteins having one or more putative phosphorylation sites; expression vectors for expressing the functional protein; transformed host, methods of expressing the modified proteins and the modified proteins.

In one embodiment, the invention provides radioactive-labelled human interferons and labelled proteins; phosphorylatable modified Hu-IFN-$\alpha$ (Hu-IFN-$\alpha$A-P) which can be phosphorylated to high radio-specific activity with retention of biological activity; other human interferons modified with various isotopes of phosphorus (e.g., $^{32}$P, $^{33}$P), or with sulfur (e.g., $^{35}$S, $^{36}$S); labelled proteins with phosphorus or analogs. In accordance with the invention, the human interferons and modified proteins may have single or multiple radioactive labels.

The invention also provides such interferons and proteins made by recombinant DNA techniques, including the Hu-IFN-$\alpha$A-P human interferons radio-labelled with phosphorus or with sulfur, and recombinant DNA-produced radio-labelled polypeptides and proteins.

The invention further provides DNA sequences encoding a functional protein which possesses one or more labelling sites and is sufficiently duplicative of human interferons for the protein sequences to possess at least one of the biological properties of interferons (like antiviral, cell growth inhibiting, and immunomodulatory properties). Further, there is provided a recombinant-DNA containing a coding sequence for a putative recognition site for a kinase; the recombinant expression vector; the host organisms transformed with the expression vector that includes the DNA sequence and an expressed modified protein. In the invention, there is used a method involving site-specific mutagenesis for constructing the appropriate expression vector, a host transformed with the vector and expressing the modified proteins, in particular the modified human interferons.

The invention provides in one of its several embodiments DNA sequences which encode one or more putative phosphorylation sites, which sequences encode functional proteins each of which possesses at least one putative phosphorylation site and each of which possesses at least one of the biological properties of Hu-IFN-$\alpha$ or -$\beta$; also expression vectors for expression of the functional modified Hu-IFN-$\alpha$ or -$\beta$ under the control of a suitable promoter such as the lambda $P_L$ promoter or others described hereinafter; also the biologically active phosphorylated Hu-IFN-$\alpha$ and -$\beta$.

Several interesting and useful applications of these modified human interferons and proteins are also disclosed by the description.

The invention also contemplates interferons or proteins other than the Hu-IFN-$\alpha$ or -$\beta$, which are modified by addition of phosphorylation sites which allow for and are labelled to higher radio-specific activities than the corresponding interferons with a single phosphorylation site. By "addition" of phosphorylation sites, there is also intended in accordance with the invention, to include interferons or proteins in which a phosphorylation site heretofore unavailable or inaccessible, has been modified to make the phosphorylation site available.

The invention further contemplates interferons, especially Hu-IFN-α, phosphorylated by appropriate kinases on amino acid residues other than on the serine residue, like on threonine and/or tyrosine residues, and the DNA sequences which code for one or more putative phosphorylation sites, which sequences code for is these interferons.

In accordance with the invention, it is sufficient that a portion of the phosphorylation recognition sequence, as opposed to the entire sequence, be added when the natural protein sequence contains the remaining (or other complementary) amino acids of said recognition sequence (e.g., Arg-Arg-Ala-Ser) (SEQ ID NO:1). In such embodiment of the invention, from 1 through 4 amino acids of the sequence (in the case of Arg-Arg-Ala-Ser-Val) (SEQ ID NO:2) can be supplied to the protein, thereby constituting the complete, necessary and Ser-containing recognition sequence. An illustration can be observed in a comparison between species Hu-IFN-αA-P1 and -P2 (in FIG. 8), wherein the natural interferon sequence contributes one Arg to the phosphorylation recognition sequence in Hu-IFN-αA-P2 when constructed in accordance with the invention.

In Hu-IFN-αA-P3, a coding sequence (and thus an additional amino acid sequence) has been supplied with the nucleotide sequence coding for the recognition sequence positioned downstream of the natural sequence coding for Hu-IFN-αA. Thus, Hu-IFN-αA-P3 is an illustration where an additional amino acid sequence is positioned between the recognition sequence and the natural amino acid sequence of Hu-IFN-αA.

This illustrates the versatility of the invention for positioning the nucleotide sequence which encodes the amino acid recognition sequence containing a putative phosphorylation site.

Thus, in accordance with the invention, there is constructed a nucleotide sequence that codes for the necessary number and specific amino acids required for creating the putative phosphorylation site.

From the above observation, the same, principles are applicable to construct any amino acid sequences other than the particular amino acid recognition sequence illustrated above.

In the situations where the phosphorylation site is other than serine (as illustrated above), the DNA sequence codes for part or all of the appropriate amino acid sequence containing the putative recognition site containing threonine, tyrosine, etc. Thus, where in any particular protein one or more amino acids (at any position of the amino acid sequence) are the same as that of an amino acid recognition sequence for a kinase, it is sufficient to add (or modify) those complementary amino acids of the amino acid recognition sequence to complete that sequence. This is accomplished by constructing a DNA sequence which codes for the desired amino acid sequence. There may indeed be situations where such addition (or modification) is a more desirable procedure as where it is important to retain the integrity of the protein molecule to be modified (for instance, to minimize risks of affecting a particular activity, e.g., biological), or for simplicity of the genetic manipulations, or because either or both termini or other positions are more accessible.

The kinase recognition sequence may be positioned at either termini or other position of the DNA coding sequence, irrespective of the specific phosphorylated amino acid.

In accordance with the invention, phosphorylation of the phosphorylatable site of the protein can be performed by any suitable phosphorylation means. Phosphorylation and dephosphorylation of proteins catalyzed by protein kinases and protein phosphatases is known to affect a vast array of proteins (21). A large number of protein kinases have been described (20, 21, 22, 38, 39, 47, 64, 100, 101, 108–112) and are available to one skilled in the art for use in the invention. Such protein kinases may be divided into two major groups: those that catalyze the phosphorylation of serine and/or threonine residues in proteins and peptides and those that catalyze the phosphorylation of tyrosine residues (see 21, 22, 38, 64, 108, for example). These two major categories can be subdivided into additional groups. For example, the serine/threonine protein kinases can be subdivided into cyclic AMP (cAMP)-dependent protein kinases, cyclic GMP (cGMP)-dependent kinases, and cyclic nucleotide-independent protein kinases. The recognition sites for many of the protein kinases have been deduced (21, 22, 38, 64, 111 present illustrative examples).

In short synthetic peptides cAMP-dependent protein kinase recognize the sequence Arg-Arg-Xxx-Ser-Xxx, where Xxx represents an amino acid (21). As noted above, the cAMP-dependent protein kinase recognizes the amino acid sequence Arg-Arg-Xxx-Ser-Xxx (21), but also can recognize some other specific sequences such as Arg-Thr-Lys-Arg-Ser-Gly-Ser-Val (111) (SEQ ID NO:3). Many other protein serine/threonine kinases have been reported (21, 100, 101, 108–112) such as glycogen synthase kinase, phosphorylase kinase, casein, kinases I and II, pyruvate dehydrogenase kinase, protein kinase C, and myosin light chain kinase.

Protein kinases which phosphorylate and exhibit specificity for tyrosine (rather than for serine, threonine, or hydroxyproline) in peptide substrates are the protein tyrosine kinases (PTK). Such PTKs are described in the literature (22, 64). The PTKs are another class of kinases available for use in the invention.

Another available class of kinases are the cyclic GMP-dependent (cGMP-dependent) protein kinases. The cGMP-dependent protein kinases exhibit substrate specificity similar to, but not identical to the specificity exhibited by cAMP-dependent protein kinases. The peptide Arg-Lys-Arg-Ser-Arg-Lys-Glu (SEQ ID NO:4) was phosphorylated at serine by the cGMP-dependent protein kinase better than by the cAMP-dependent protein kinase (21, 22, 113). It has also been shown that the cAMP-dependent protein kinase can phosphorylate hydroxyproline in the synthetic peptide Leu-Arg-Arg-Ala-Hy-Leu-Gly (114) (SEQ ID NO:5).

Casein kinases, widely distributed among eukaryotic organisms and preferentially utilizing acidic proteins such as casein as substrates, have been classified into two groups, casein kinases I and II (21). Casein kinase II phosphorylated the synthetic peptide Ser-Glu-Glu-Glu-Glu-Glu (115) (SEQ ID NO:6). Evaluation of results with synthetic peptides and natural protein substrates revealed that a relatively short sequence of amino acids surrounding the phosphate acceptor site provides the basis for the specificity of casein kinase II (118). Accordingly, the acidic residues at positions 3 and 5 to the carboxyl-terminal side of the serine seem to be the most important. Serine was preferentially phosphorylated compared to threonine. In another study (117), the peptide Arg-Arg-Arg-Glu-Glu-Glu-Thr-Glu-Glu-Glu (SEQ ID NO:7) was found to be a specific substrate for casein kinase II; however, Arg-Arg-Arg-Glu-Glu-Glu-Ser-Glu-Glu-Glu (SEQ ID NO:8) was a better substrate (118); and Arg-Arg-Arg-Asp-Asp-Asp-Ser-Asp-Asp-Asp (SEQ ID NO:9) was a better substrate than Arg-Arg-Arg-Glu-Glu-Glu-Ser-Glu-Glu-Glu (SEQ ID NO:10). Thus, aspartate is preferred over glutamate (118). Acidic residues on the COOH-terminal side of the serine (threonine) are as far as known today absolutely required; acidic residues on the amino-terminal side of the serine (threonine) enhance phosphorylation, but are not absolutely required: thus, Ala-Ala-Ala-Ala-Ala-Ala-Ser (Thr) -Glu-Glu-Glu (SEQ ID NO:11) served as a substrate for casein kinase II, but was less effective than Ala-Ala-Ala-Glu-Glu-Glu-Ser (Thr) -Glu-Glu-Glu(118) (SEQ ID NO:12) (the designation Ser(Thr) means serine or threonine). Casein kinases I and II phosphorylate many of the same substrates (21) although casein kinase I did not phosphorylate any of the decamer peptide substrates noted here (118). It was concluded from studies with a variety of synthetic peptides that the sequence Ser-Xxx-Xxx-Glu (and by inference Ser-Xxx-Xxx-Asp) may represent one class of sequences that fulfill the minimal requirements for recognition by casein kinase II although some other peptides and sequences may also suffice (see 118 for a detailed discussion).

As noted above, other kinases have been described. The mitogen-activated S6 kinase phosphorylates the synthetic peptide Arg-Arg-Leu-Ser-Ser-Leu-Arg-Ala (109) (SEQ ID NO:13) as does a protease-activated kinase from liver (21, 109). The rhodopsin kinase catalyzes the phosphorylation of the peptide Thr-Glu-Thr-Ser-Gln-Val-Ala-Pro-Ala (21) (SEQ ID NO:14). Other protein serine/threonine kinases have been described and their sites of phosphorylation elucidated (21).

The substrate specificity of tyrosine kinases have also been reported (64, pages 920–921; 110). A variety of synthetic or natural peptide substrates have been described (64, 110).

Thus, one skilled in the art has quite an adequate selection of available kinases for use in the invention, which have relatively high specificity with respect to the recognition process, but some flexibility to the specific sequence of the amino acid recognition site. Such kinases provide means for phosphorylation of putative phosphorylation sites in the desired proteins.

The selection of the position of the molecule best suited for the modification depends on the particular protein (and its configuration). Where multiple putative phosphorylation sites (and phosphorylatable sites) are to be included in the modified protein, one would consider the potential availability of either or both ends and other positions of the molecule for providing the amino acid recognition sequence. Thus, in accordance with the invention, phosphorylation recognition sequences can be introduced at any point in a naturally occurring protein sequence providing such introduced sequences do not adversely affect biological activity where such activity is desired.

Once the recognition site for a particular protein kinase is identified, the invention provides a method for making by recombinant-DNA techniques the DNA sequence which encodes the recognition site for that kinase within, fused or linked to the DNA sequence encoding the functional protein which is to contain the corresponding putative labelling site.

The invention contemplates and includes any protein which is radio-labellable by the methods of this invention and which possesses at least one of the properties of the corresponding unlabelled (or unlabellable) protein. In accordance with the invention, the non-phosphorylated (or non-phosphorylatable) protein is modified to introduce into the amino acid sequence the putative phosphorylatable site; this is performed after having modified the DNA sequence encoding the amino acid sequence of the protein with the DNA sequence (part or all) which codes for the putative phosphorylated site. In the case of interferons, the invention includes all interferons natural or "non-natural" interferons, including such structurally modified interferon species which have been reported in the literature (such as hybrid interferons, modified interferons) as discussed above, and other modified interferons which will be reported in the future.

Natural and "non-natural" (including modified) interferon species have a variety of biological activities and such activities are known to occur in different ratios; thus, the invention contemplates not only radio-labelled interferons which have any one of these properties (and in any ratio), but also biological or other properties not yet identified in the known interferon species. It is recognized that the phosphorylation may modify one or more of the properties of the protein to one degree or another (see 47, 100, 101, for example). Indeed there are situations where the properties may be enhanced or developed where they were not detectable prior to modification of the protein.

The invention also provides particularly interesting labellable and labelled proteins like phosphorylated antibodies (especially monoclonal antibodies, hybrid antibodies, chimeric antibodies or modified antibodies), hormones, and "modified" streptavidin. The modified streptavidin can be bound to individual biotinylated antibodies, each streptavidin being modified by single or multiple phosphorylated groups, which product has greatly enhanced radiation and therefore diagnostic and therapeutic potential.

The invention also provides a hybrid interferon protein Hu-IFN-αA/gamma constituted of Hu-IFN-αA to which there is fused the COOH-terminal 16 amino acid region of Hu-IFN-gamma, which contains a putative phosphorylation site, and the hybrid interferon fusion protein labelled with phosphorus. The fusion protein was synthesized with an expression vector constructed by oligonucleotide-directed mutagenesis. The invention also provides the DNA coding sequence for the fused hybrid interferon protein, expression vectors and the transformed microorganisms, e.g. *E. coli* host and other suitable hosts described below.

The foregoing is not intended to have identified all of the aspects or embodiments of the invention nor in any way to limit the invention. The invention is more fully described below.

The accompanying drawings, which are incorporated and constitute part of the specification, illustrate embodiments of the invention, and together with the description, serve to explain the principles of the invention.

BRIEF DESCRIPTION OF THE DRAWINGS

The Figures first illustrate the fused-hybrid interferon (FIGS. 1–7) and then the other modified interferons made in accordance with the invention (FIGS. 8–13).

The EcoRI fragment from pRC23/IFN-gamma was ligated into the BstEII site of pXZ-6 (pIFN-αA) by blunt-end ligation to yield pXZ-7. The EcoRI fragment of pXZ-7 was inserted into M13mp18 to yield M13mp18/IFN-αA/IFN-gamma. Oligonucleotide-directed deletion was performed on this latter construct with the oligonucleotide shown to yield a recombinant containing the proper deletion (M13mp18/IFN-αA/gamma). The EcoRI fragment from this M13 recombinant replaced the EcoRI insert of pXZ-6 to yield pXZ-8 (pIFN-αA/gamma), the expression plasmid encoding the Hu-IFN-αA/gamma fusion protein. The proper construction was confirmed by sequencing the recombinant. T4-t represents the phage T4 transcription terminator (56, 57); Ap, ampicillin; cip, calf intestinal phosphatase.

FIG. 3 shows the nucleotide sequence (SEQ ID NO:17) encoding and amino acid sequence (SEQ ID NO:18) of the hybrid Hu-IFN-αA/gamma.

Figure 4:
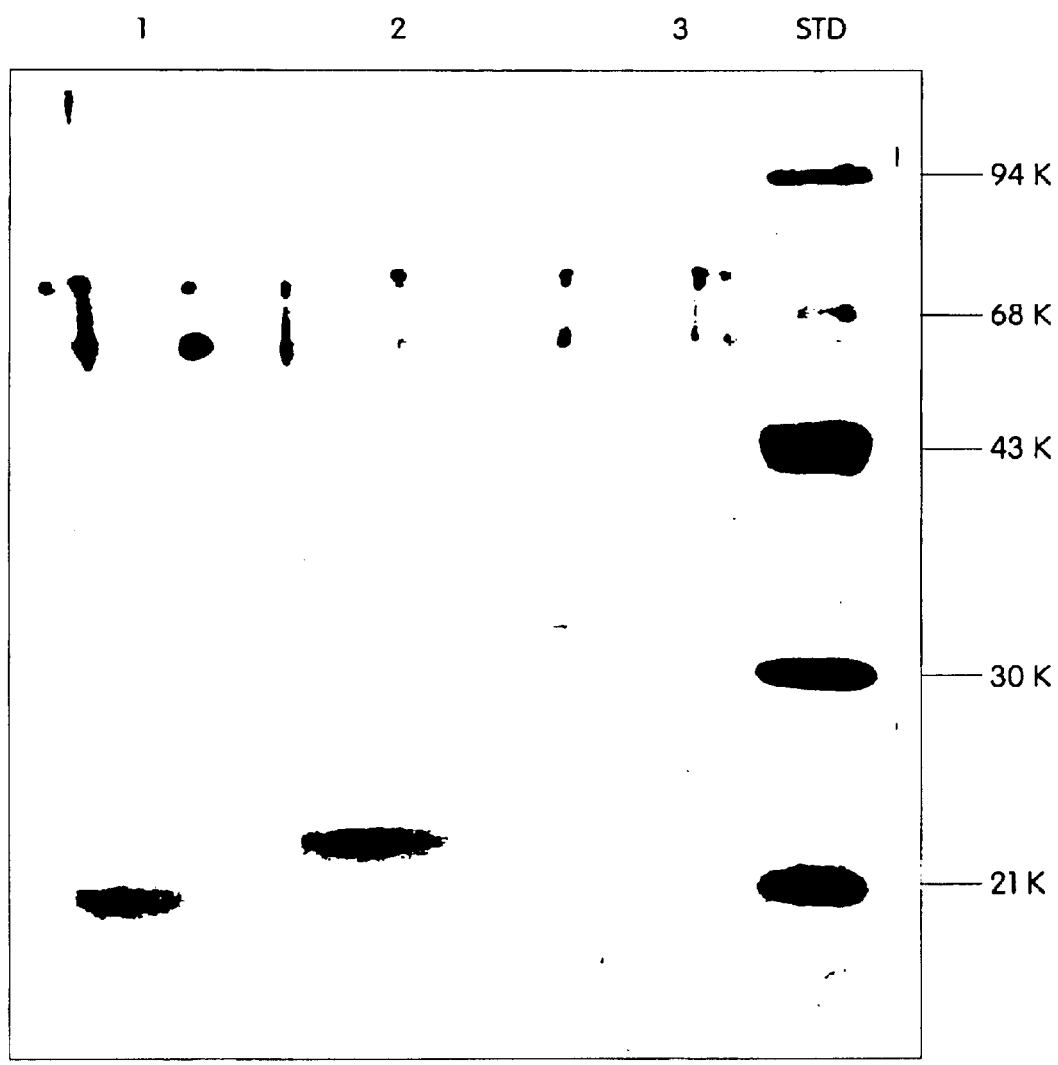

FIG. 4 shows a polyacrylamide gel electrophoresis of the purified proteins. Lane 1 represents Hu-IFN-αA; lane 2, the fused protein Hu-IFN-αA/gamma; and lane 3, Hu-IFN-gamma. The molecular weight standards (STD) are shown in the right column. The gels were developed with a silver stain.

Figure 5:
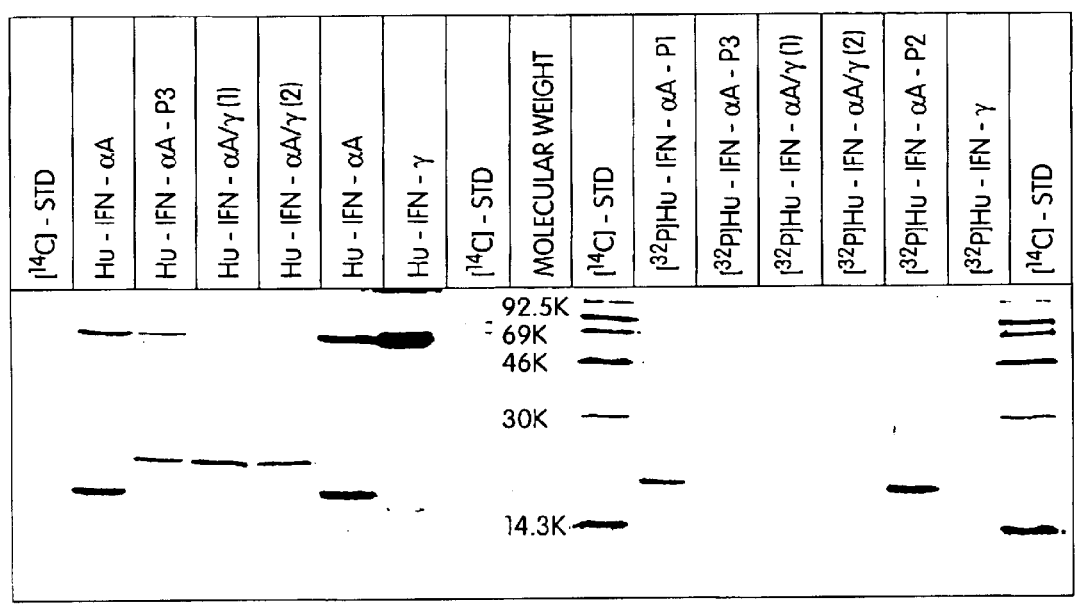

FIG. 5 shows a polyacrylamide gel electrophoresis of phosphorylated Hu-IFN-gamma and the fusion protein Hu-IFN-αA/gamma. The left panel of the Figure represents the gel stained with Coomassie blue. The right panel represents the autoradiograph of the same gel as shown on the left panel. The heavy stained bands at $MW_R$ 69,000 represent bovine serum albumin which was added to the phosphorylation reactions.

Figure 6:
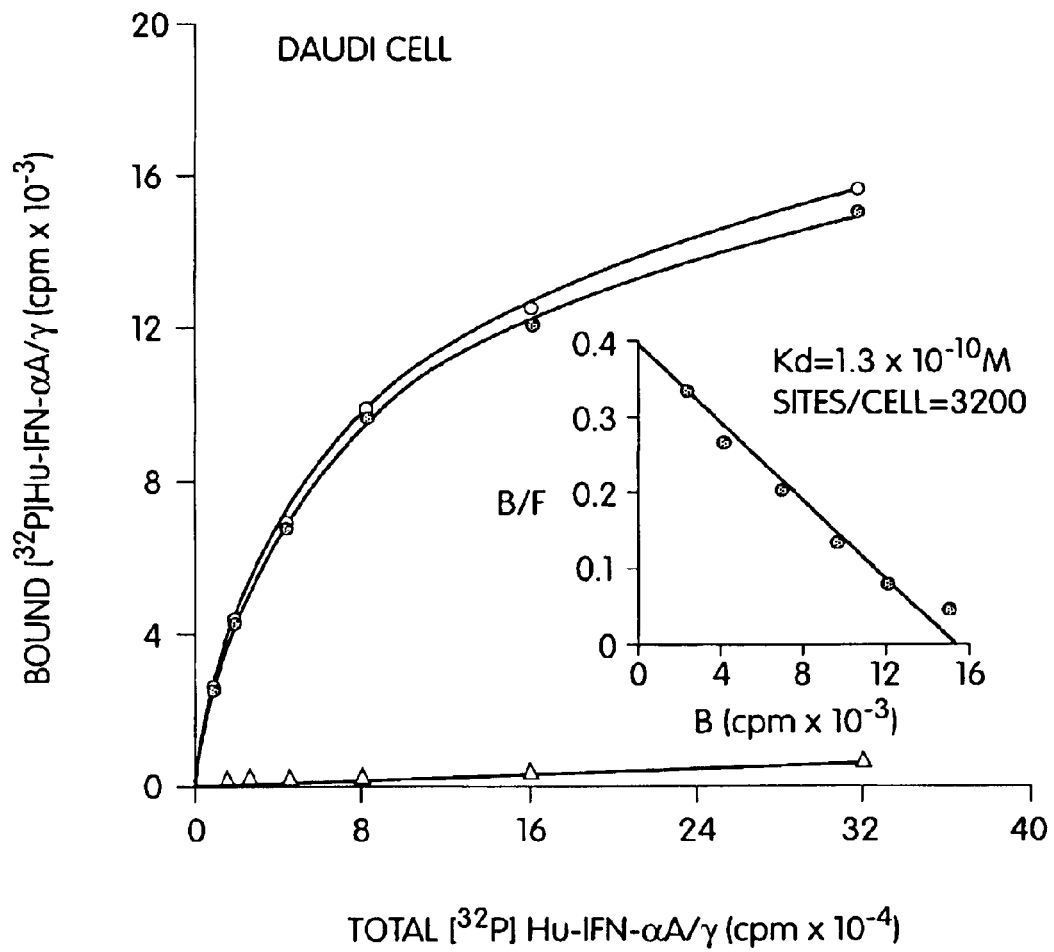

FIG. 6 shows the binding of [$^{32}$P]Hu-IFN-αA/gamma to Daudi cells. The binding of [$^{32}$P]Hu-IFN-αA/gamma to Daudi cells was performed as described under "Experimental Procedures". Specific binding (●) represents the difference between total binding (○) and non-specific binding (Δ). Non-specific binding represents the binding in the presence of excess unlabelled Hu-IFN-α/A. The specific activity of [$^{32}$P]Hu-IFN-cLA/gamma was about 141 μCi/ug.

Figure 7:
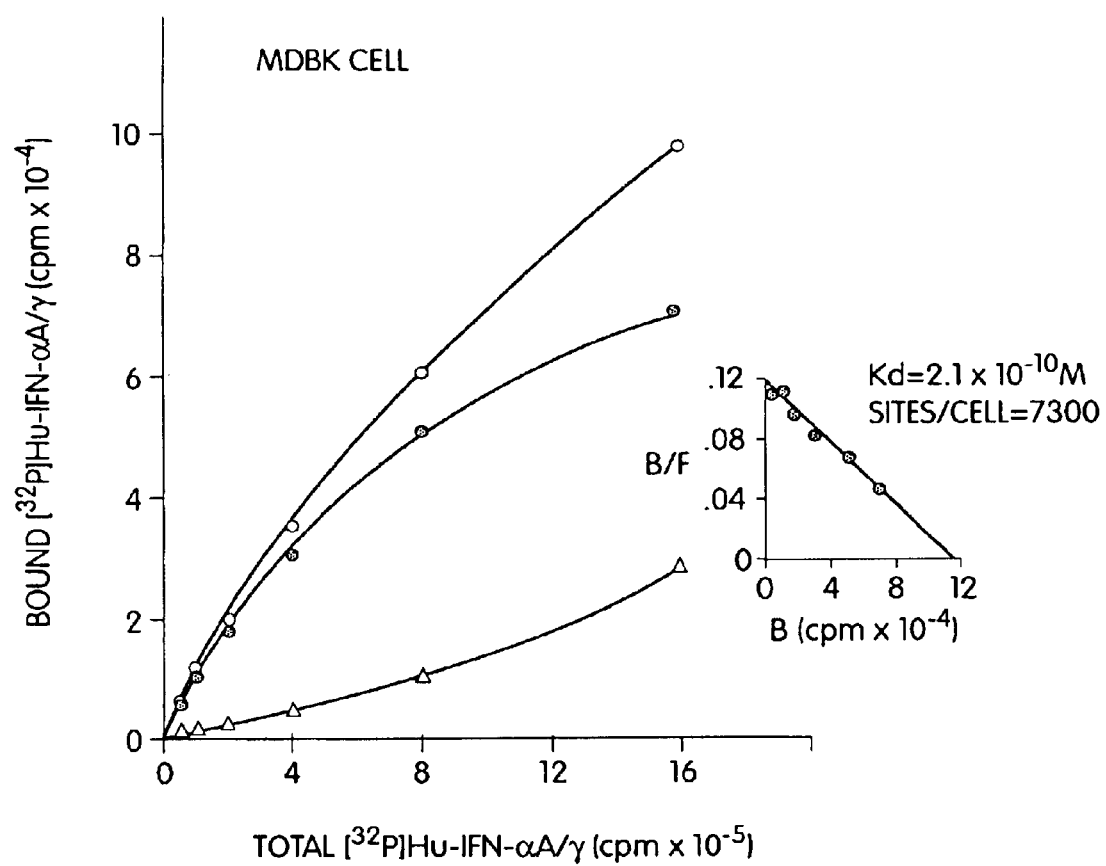

FIG. 7 shows the binding of [$^{32}$P]Hu-IFN-αA/gamma to MDBK cells. The symbols and explanations are the same as in FIG. 6.

FIG. 8 shows nucleotide and amino acid sequences of the COOH terminus of Hu-IFN-αA, Hu-IFN-αA-P1, -P2, and -P3 (SEQ ID NOS:19–26). The phosphorylation sites recognized by the cAMP-dependent protein kinase created in Hu-IFN-αA-P1, -P2, and -P3 are shown in rectangles. The sites contain the recognition sequence Arg-Arg-Ala-Ser-Leu (SEQ ID NO:27) or Arg-Arg-Ala-Ser-Val (SEQ ID NO:2) (for phosphorylation of this Ser) for the cAMP-dependent bovine heart kinase together with additional amino acids. The nucleotide sequences and amino acid sequences of the interferons are aligned for comparison.

Figure 9:
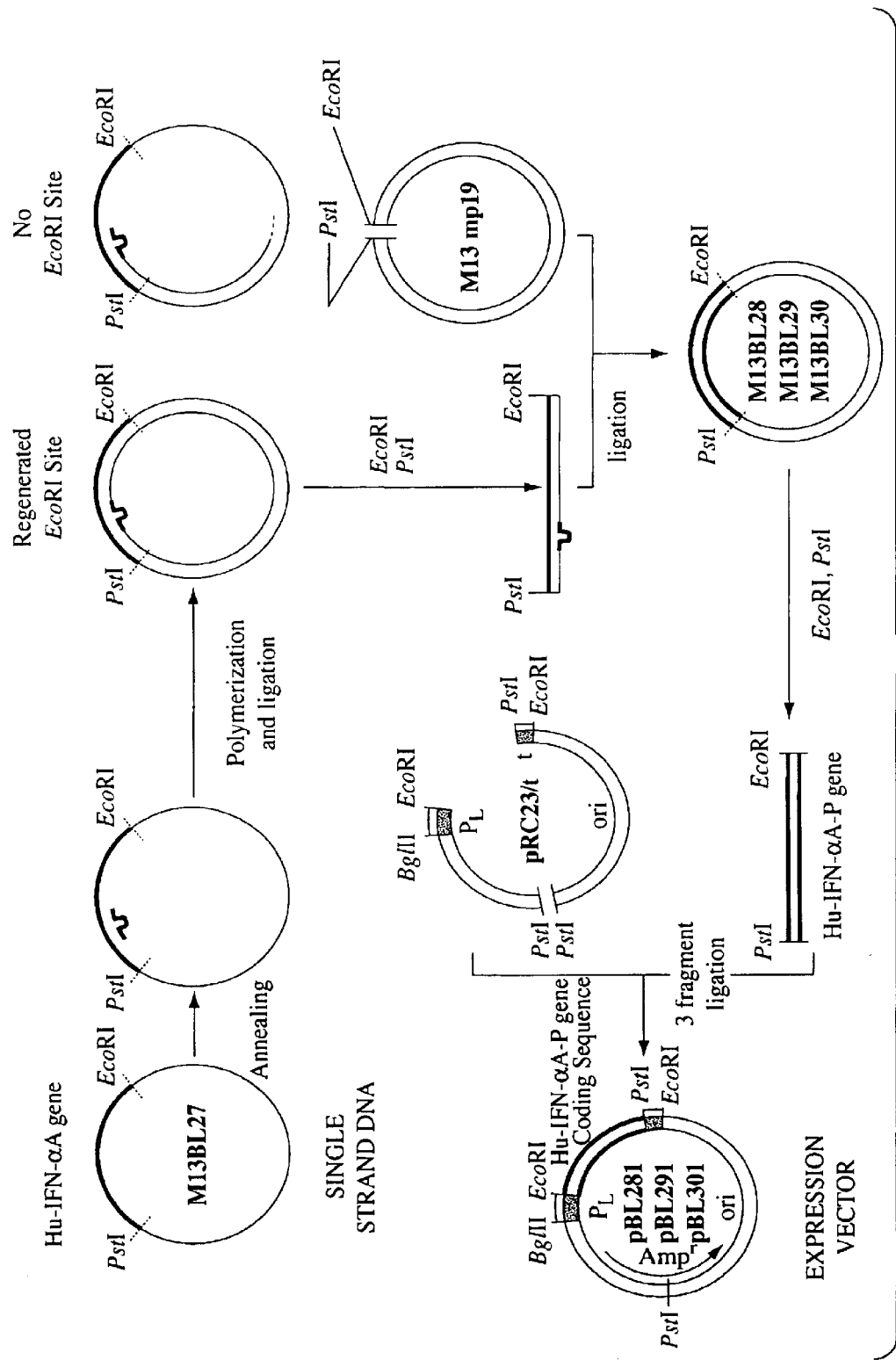

FIG. 9 shows the construction of expression plasmids for Hu-IFN-αA containing phosphorylation sites.

Figure 10:
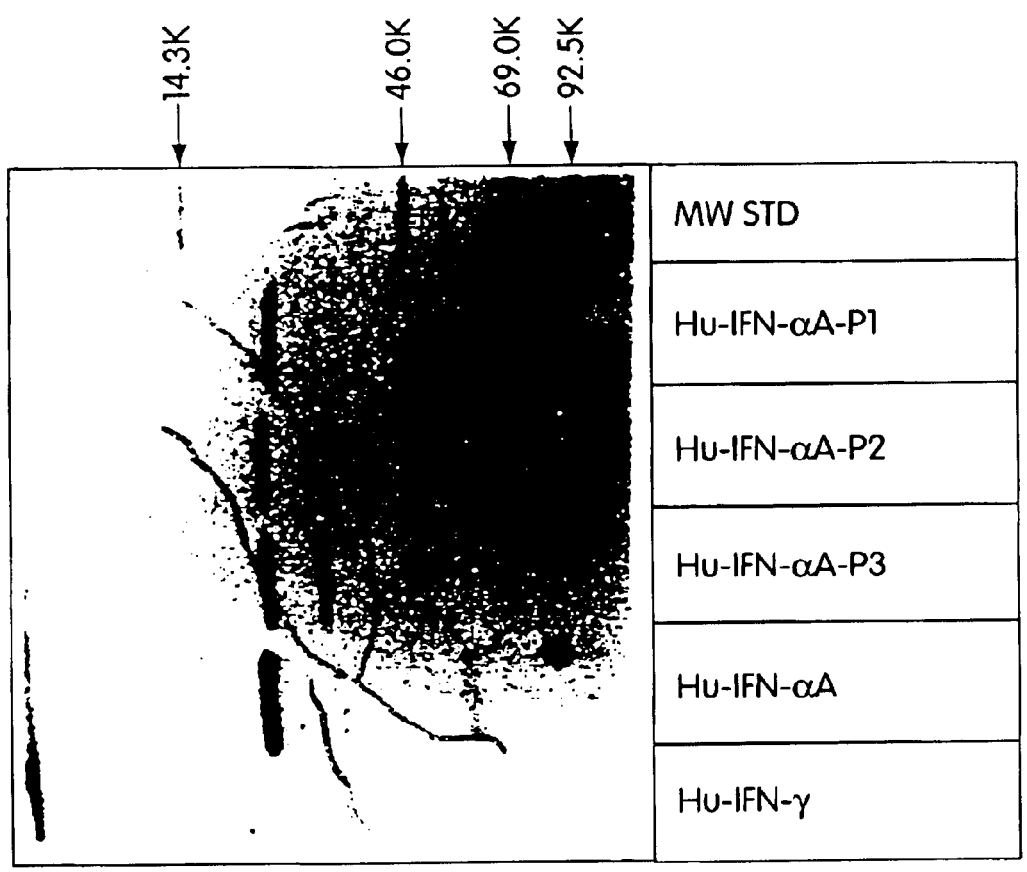

FIG. 10 shows an analysis of Hu-IFN-αA-P proteins by SDS-polyacrylamide gel electrophoresis. The gel was stained with silver. Molecular weight standards are shown on the left most lane.

Figure 11:
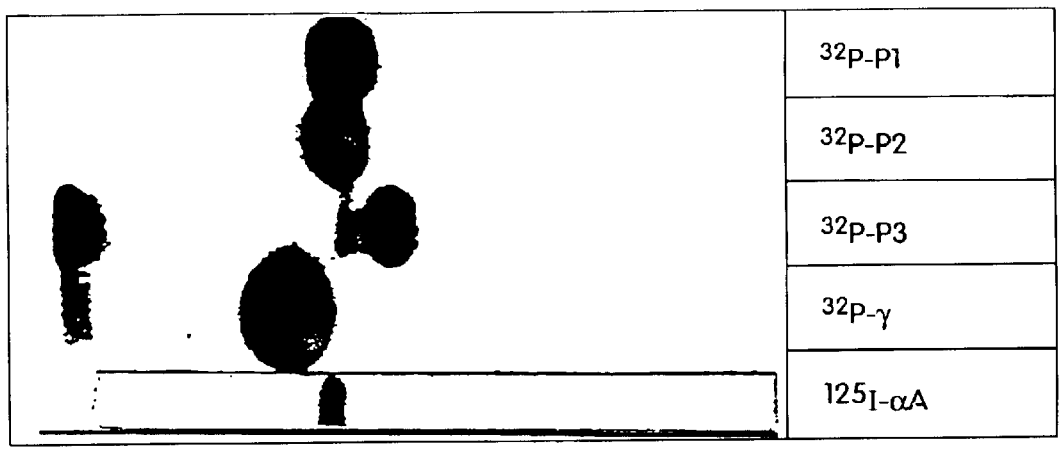
Figure 12A:
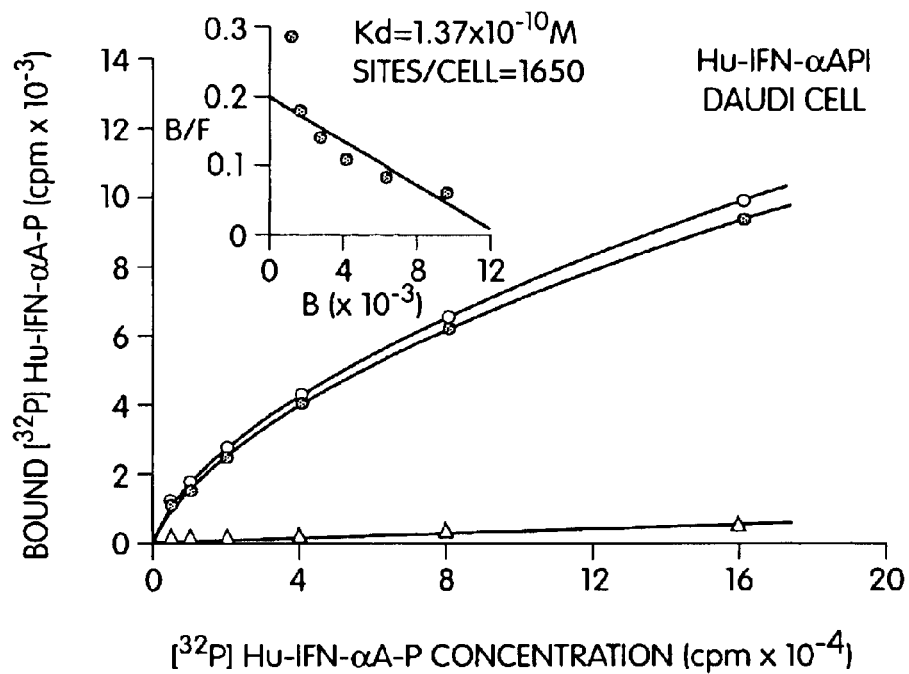
Figure 12B:
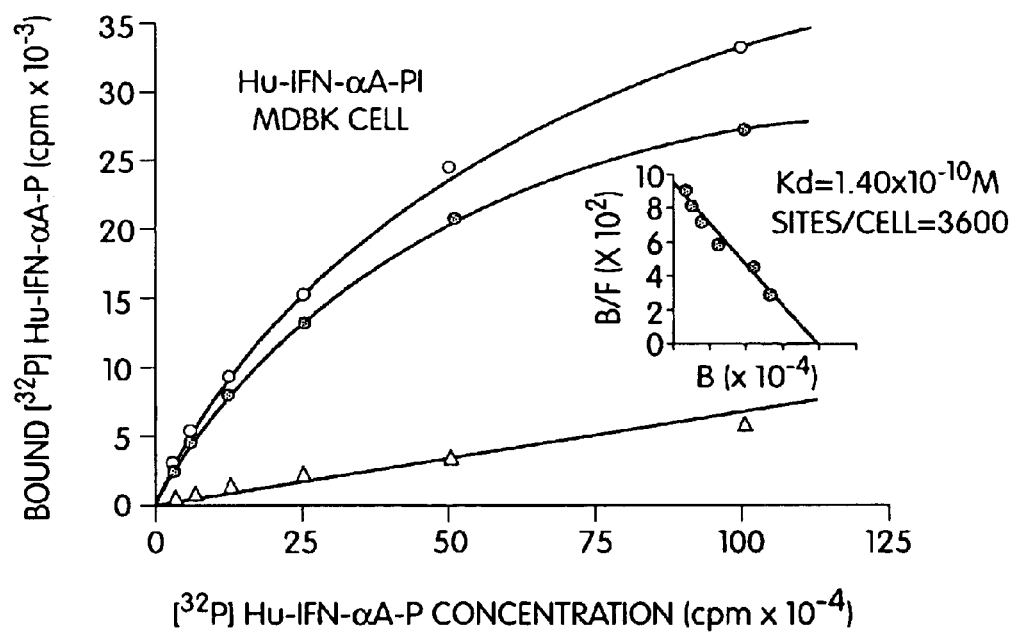
Figure 12C:
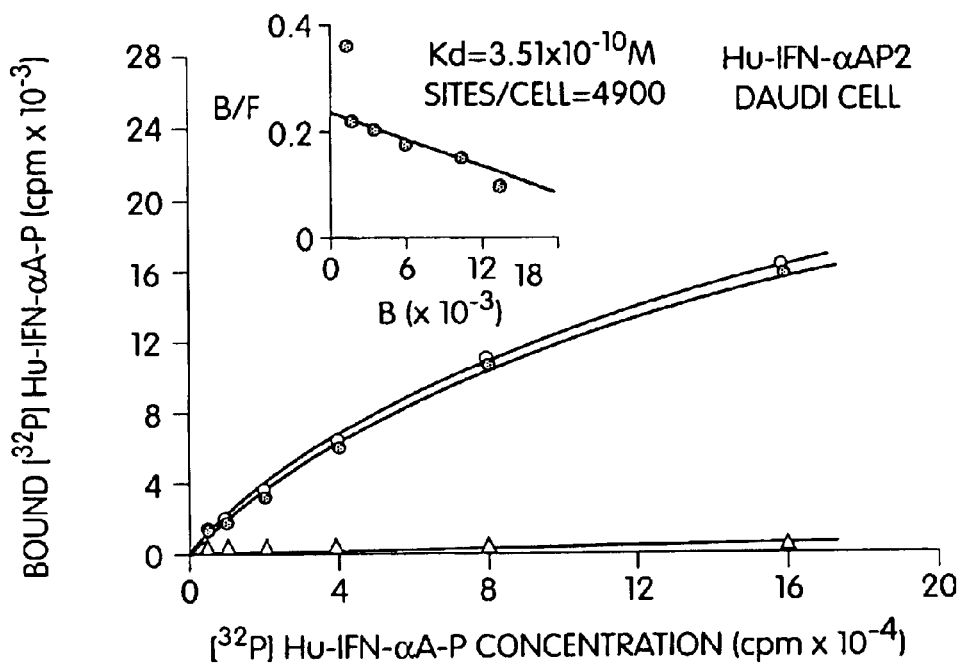
Figure 12D:
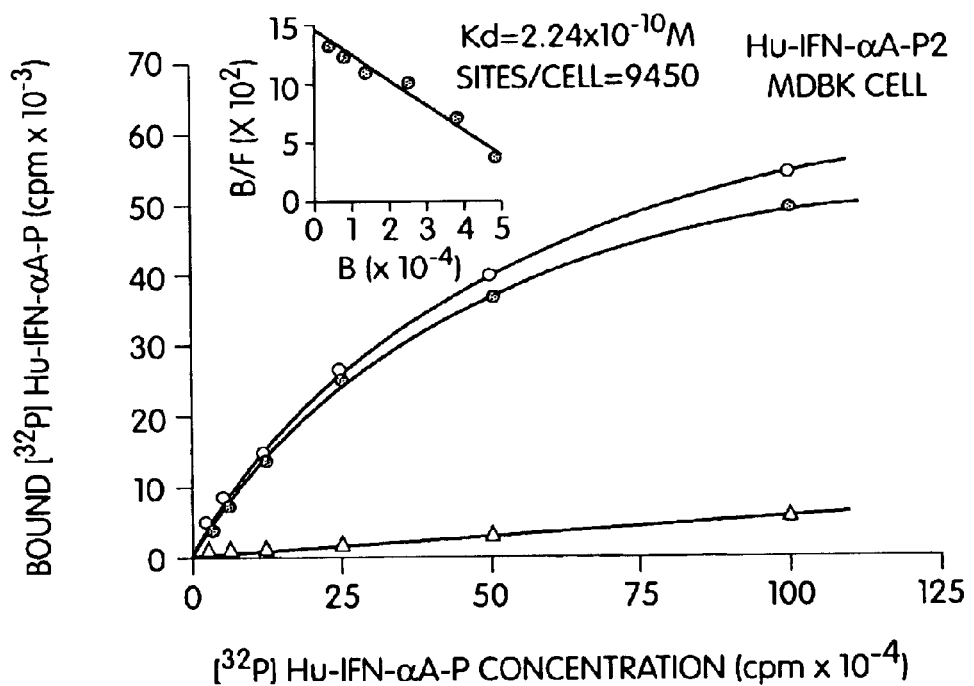

FIG. 11 shows an autoradiograph of SDS-polyacrylamide gel electrophoresis of the phosphorylated proteins. Hu-IFN-gamma serves as an internal molecular weight standard as in FIG. 10.

FIG. 12 shows the binding of [$^{32}$P]Hu-IFN-αA-P proteins to cells. The inset represents Scatchard analysis of the specific binding data. "B" represents the radioactivity of ligands bound to cells and "F" is the radioactivity of free or unbound ligands. (A) and (B): binding [$^{32}$P]Hu-IFN-αA-P1 to Daudi and MDBK cells, respectively; (C) and (D): binding of [$^{32}$P]Hu-IFN-αA-P2 to Daudi and MDBK cells, respectively.

Figure 13:
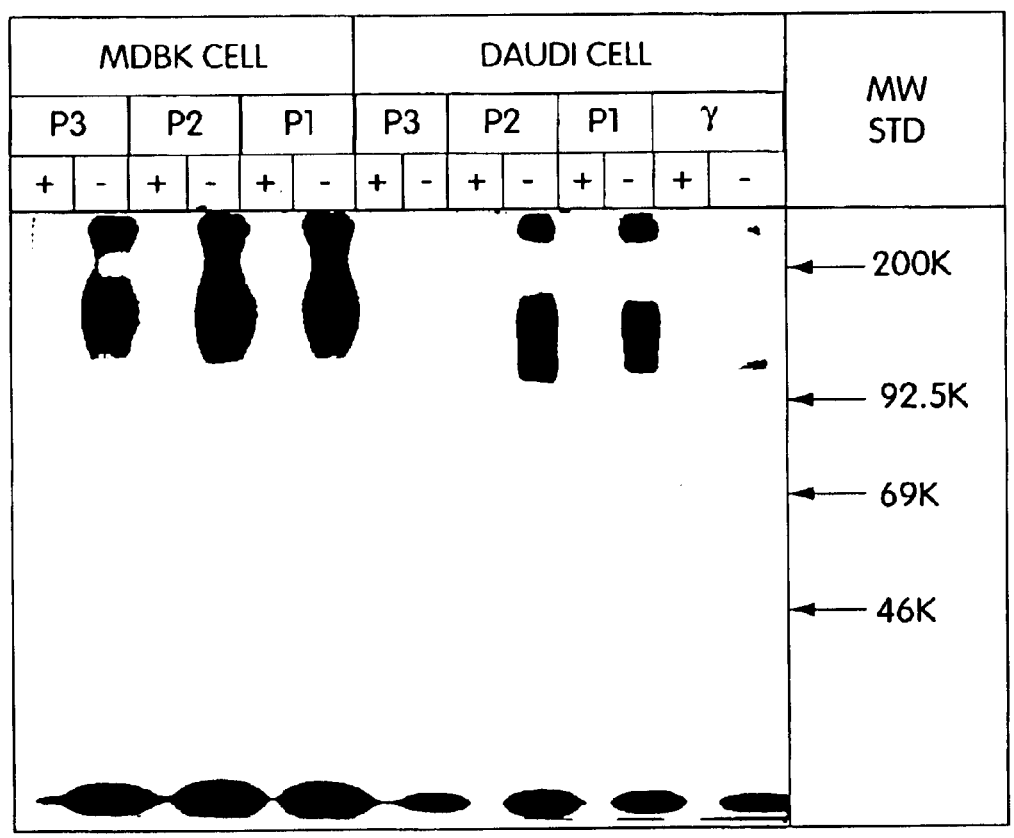

FIG. 13 shows the electrophoretic analysis of crosslinked [$^{32}$P]Hu-IFN-αA-P1, -P2 and -P3 receptor complexes.

The Figures are explained in greater detail hereinbelow.

DESCRIPTION OF SPECIFIC EMBODIMENTS

In accordance with the invention, proteins which are normally not phosphorylatable can be modified to render them phosphorylatable. In particular, it was of great interest in conjunction with this invention to determine whether and how one could achieve the phosphorylation of a particular protein, the interferon Hu-IFN-αA, which as opposed to Hu-IFN-gamma could not be phosphorylated (as discussed above). The methodology to achieve this result (especially without loss of its biological activity) has provided the potential to modify other proteins and render them phosphorylatable. Thus, in accordance with the invention, Hu-IFN-αA has been used as a model for phosphorylation of proteins in general.

Hu-IFN-αA has been modified in accordance with the invention to yield two embodiments, which will be described hereinafter. Both embodiments are applicable to proteins in general and one skilled in the art will select that most suitable under the particular circumstances.

The first embodiment is the construction of a phosphorylatable hybrid or fused protein, Hu-IFN-αA/gamma; the second embodiment is a phosphorylatable modified Hu-IFN-αA with an insert more fully described below.

The following describes illustrative, but not limiting, specific embodiments.

Hu-IFN-αA/Gamma, a Hybrid Protein of Hu-IFN-αA and the COOH-terminal 16 Amino Acids of Hu-IFN-gamma The following describes a hybrid or fused protein of Hu-IFN-αA and Hu-IFN-gamma. The fused-hybrid protein was expressed by an expression vector constructed by oligonucleotide-directed mutagenesis. The construction of the expression vector, the expression and purification of the protein, the phosphorylation of the functional hybrid protein and the binding of [$^{32}$P]Hu-IFN-αA/gamma to cells (MDBK) are described below. The hybrid protein has antiviral activity.

The fusion protein prepared in accordance with the invention comprises Hu-IFN-αA to which the COOH-terminal 16 amino acids of Hu-IFN-gamma was fused. The protein was prepared by constructing an expression vector by oligonucleotide-directed mutagenesis. The hybrid protein Hu-IFN-αA/gamma was expressed under the control of the phage lambda $P_L$ promoter. The protein was purified with a monoclonal antibody against Hu-IFN-α or the COOH-terminal amino acid sequence of Hu-IFN-gamma. The purified protein exhibited a single major band on sodium dodecyl sulfate-polyacrylamide gel electrophoresis and has antiviral activity on human and bovine cells. Unlike Hu-IFN-αA, but similar to Hu-IFN-gamma, it was found that the hybrid Hu-IFN-αA/gamma can be phosphorylated by [gamma-$^{32}$P]ATP and cAMP-dependent protein kinase. The phosphorylated molecule binds to the IFN-αL/β receptor.

The introduction of a phosphorylation site into Hu-IFN-αA by fusion of the region of Hu-IFN-gamma which contains the putative phosphorylation site provides a new reagent for studies of receptor binding, pharmacokinetics and other studies where labelled interferons are useful.

Thus, in accordance with the invention, a hybrid protein was constructed by fusing the COOH-terminal end of Hu-IFN-gamma to the COOH terminus of Hu-IFN-αA to yield a hybrid protein which contains the putative phosphorylation site. The phosphorylated protein was found to be biologically active.

The construction of a plasmid for expression of hybrid Hu-IFN-αA/gamma was carried out as follows.

Figure 2:
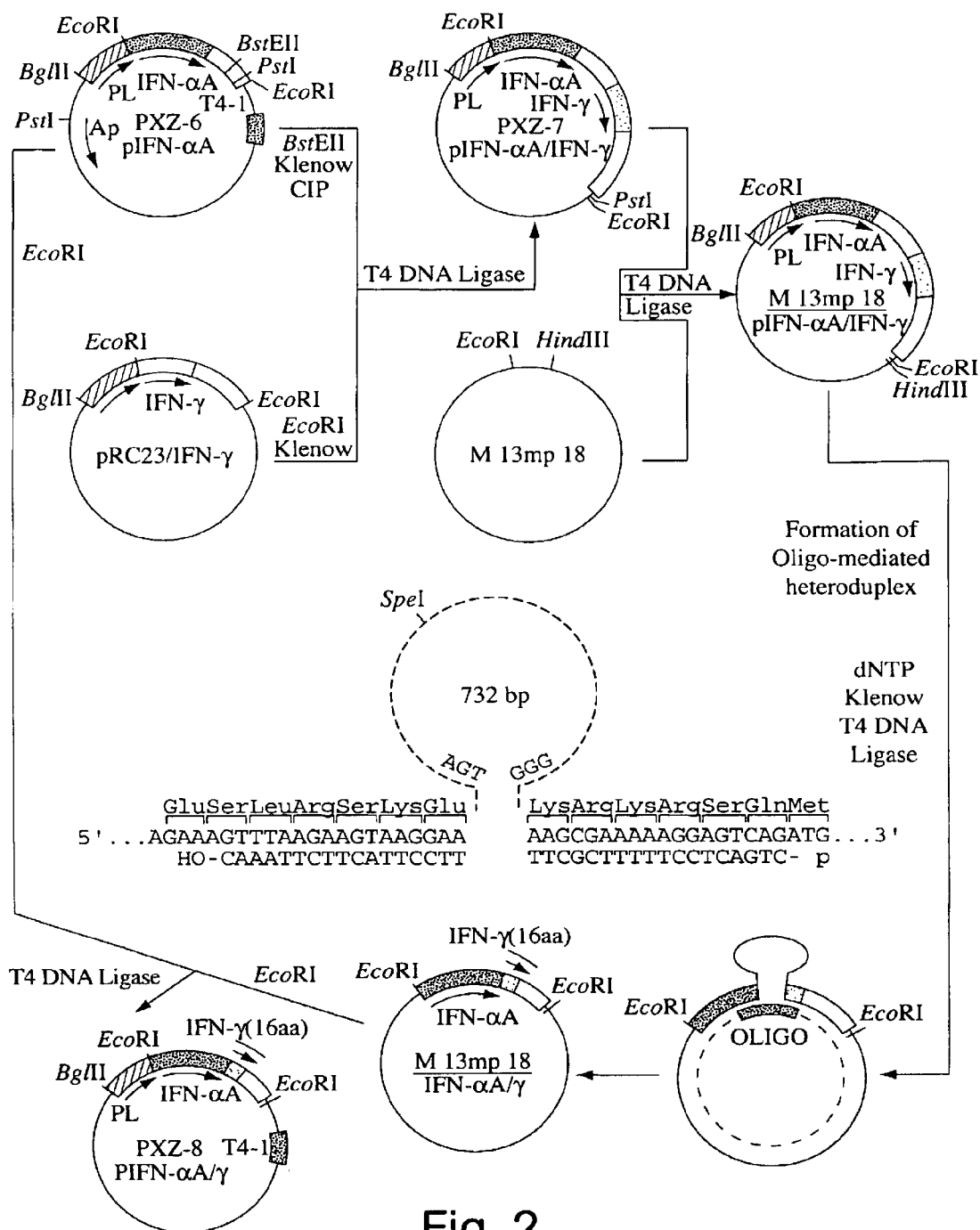
FIG. 2 shows an outline of the construction of the fusion protein from Hu-IFN-αA and Hu-IFN-gamma, the Hu-IFN-αA/gamma (SEQ ID NOS:15 and 16).

As shown in FIG. 2, the DNA sequences for Hu-IFN-αA and Hu-IFN-gamma were cloned into M13mp18. Plasmid pXZ-8 encoding a fusion protein was constructed by oligonucleotide-directed deletion as shown.

Plasmid pXZ-8 is deposited with the ATCC under Accession number 40510, and designated as pHu-IFN-αA/gamma.

Figure 1:
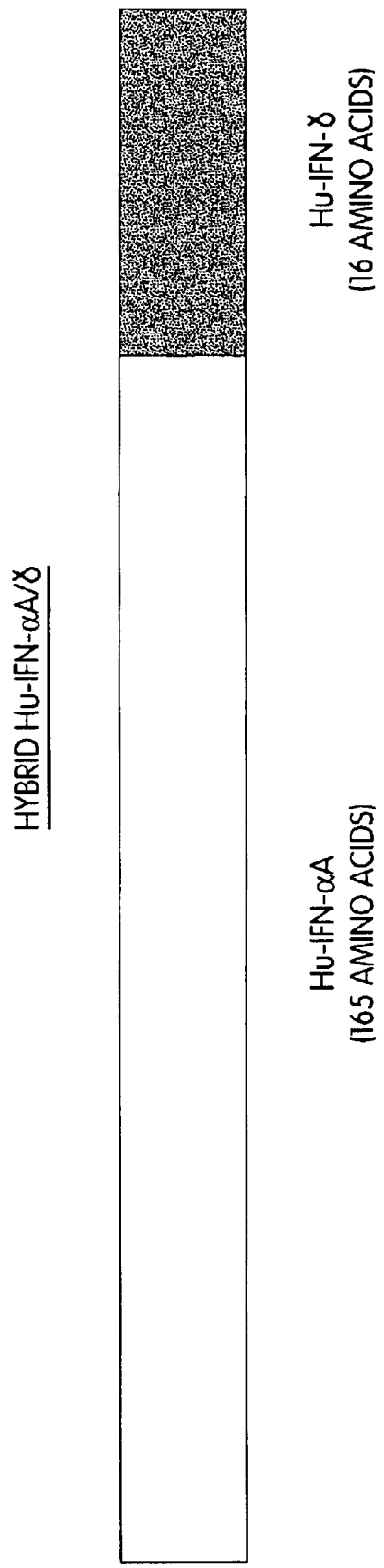
FIG. 1 is a schematic illustration of a hybrid interferon Hu-IFN-αA/gamma of Hu-IFN-αA and Hu-IFN-gamma, the Hu-IFN-gamma segment representing the 16 COOH-terminal amino acids and containing the putative phosphorylation site.

To screen for the plasmid recombinant with the proper deletion, colony hybridization was performed on 200 colonies with the oligomer as probe (58) with the observation that 53 colonies were positive. Of the 53 positive colonies, 36 were analyzed by restriction digestion with EcoRI with the result that only two colonies contained the expected restriction fragments. DNA sequencing confirmed that the 5' end of the sequence coding for the 16 COOH-terminal amino acids of Hu-IFN-gamma was fused to the 3' end of the coding sequence for Hu-IFN-αA (FIGS. 1, 2, and 3). A 732 bp fragment was deleted in the correct recombinant. The gene for hybrid Hu-IFN-αA/gamma was constructed and expressed under control of the lambda $P_L$ promoter. The sequence of hybrid Hu-IFN-αA/gamma consists of 181 amino acids (FIG. 3).

As discussed further below, other promoters in various expression vectors can also be used.

The characterization and phosphorylation of hybrid Hu-IFN-αA/gamma was performed as follows.

Hu-IFN-αA/gamma was induced when the *E. coli* RR1 (pRK248cIts857) cells or *E. coli* AR68(pRK248cIts857) cells harboring the plasmid pXZ-8 were grown at 42° C. and the hybrid protein was purified by monoclonal antibody affinity chromatography as described hereinafter. The purified protein exhibited a specific activity of $4 \times 10^8$ units/mg. On SDS-polyacrylamide gel electrophoresis in the presence of 2-mercaptoethanol, it exhibited a major single band which migrated slower than Hu-IFN-αA and almost at the same position of Hu-IFN-αA-P3, another Hu-IFN-αA derivative with 182 amino acids as shown in FIGS. 4 and 5. It was observed that Hu-IFN-αA/gamma is not as stable as Hu-IFN-αA. During experimental procedures, purification steps, and storage, degradation of the protein extracted from *E. coli* RR1 was observed; much less degradation was observed when *E. coli* AR68 was used as the host cell.

It was found that hybrid Hu-IFN-αA/gamma can be phosphorylated with [gamma-$^{32}$P]ATP and bovine heart muscle cAMP-dependent protein kinase. The specific radioactivity of [$^{32}$P]Hu-IFN-αA/gamma was about 5 $\mu$Ci/$\mu$g protein in preparations isolated from *E. coli* RR1; in preparations of Hu-IFN-αA/gamma isolated from *E. coli* AR68, the specific radioactivity was increased to about 141 $\mu$Ci/$\mu$g, presumably reflecting greater integrity of the carboxyl terminus. These values are similar to the range of values obtained for [$^{125}$I]IFN-αA (59–62). [$^{32}$P]IFN-αA/gamma migrates as a single species at the same position as unlabelled IFN-αA/gamma on SDS-polyacrylamide gel electrophoresis in the presence of 2-mercaptoethanol (FIG. 5).

The binding of [$^{32}$P]Hu-IFN-αA/gamma to cells was as follows.

Bovine MDBK cells were used for binding studies because Hu-IFN-αA exhibits high antiviral activity on this cell line and binds to it (16, 28, 63), whereas Hu-TFN-gamma does not. To determine whether Hu-IFN-αA/gamma binds specifically to bovine MDBK and human Daudi cells, cells were incubated with various concentrations of [$^{32}$P] Hu-IFN-αA/gamma in the absence and presence of unlabelled Hu-IFN-αA. Specific binding of [$^{32}$P]Hu-IFN-αA/gamma to both MDBK and Daudi cells is shown in FIGS. 5 and 7.

These results with [$^{32}$P]Hu-IFN-αA/gamma indicate that the fusion of the phosphorylation site of Hu-IFN-gamma to the COOH terminus of Hu-IFN-αA, which itself cannot be phosphorylated, did -not destroy the capability of the protein to bind. The Hu-IFN-αA/gamma protein also retained its activity.

This description of the first embodiment of the invention shows the successful construction of a hybrid DNA sequence capable of coding for an amino acid sequence containing a putative phosphorylation site, the construction of a suitable expression vehicle and of a transformed host which readily expressed the hybrid protein with an intact putative phosphorylation site, and its phosphorylation.

The second principal embodiment of the invention reached the initial objective in a somewhat different manner; yet it still resulted in a modified interferon which is phosphorylatable.

While in the first above-described embodiment, the DNA sequence coding for the entire protein which is not phosphorylatable, in this case Hu-IFN-αA, is modified by fusion at the end of its sequence to a sequence which codes for a putative phosphorylatable amino acid sequence, the second embodiment does not require the fusion to be at the end of the sequence and, in fact, does not require a fusion step.

Thus, the second embodiment shows the wider applicability of the invention to proteins in general.

In the second embodiment the resulting protein has been modified by insertion of an appropriate phosphorylatable sequence.

The second embodiment will be described hereinafter.

Hu-IFN-α Having Inserted Labellable Sites

An important concept of the invention is the incorporation of a kinase-recognizable amino acid sequence into selected proteins (or converting an amino acid sequence which is not recognizable by a protein kinase into a sequence which is so recognized), and labelling the proteins which contain the putative kinase-recognizable phosphorylation site by attaching a selected radioactive label by means of the catalytic action of the kinase.

Generally, these steps will be performed at the level of the nucleotide sequence by DNA recombinant procedures. After the amino acid consensus sequence recognizable by a protein kinase is identified, the nucleotide sequence encoding this amino acid sequence can be defined and constructed. For purposes of this disclosure, a nucleotide sequence encoding an amino acid sequence recognizable by a protein kinase will be designated a "PK nucleotide sequence". Similarly, the amino acid sequence recognizable by a protein kinase will be designated "PK amino acid sequence". A PK nucleotide sequence can be introduced into any selected nucleotide sequence, specifically a nucleotide sequence encoding the amino acids of a protein, polypeptide, or peptide. Preferably, the PK sequence is inserted into or joined to a nucleotide sequence which codes for a protein in such a manner so that the protein product is biologically, biochemically or otherwise active. The term "biologically active" is used throughout in this generic sense. Thus, the modified protein will be phosphorylatable and still be biologically active. Additionally, the phosphorylated modified protein should also be appropriately active for the use desired. In some cases, the phosphorylated protein could be inactive biologically, yet still be useful in a radioimmunoassay, for example.

It is only necessary in accordance with the invention that there be incorporated that much of the amino acid consensus sequence that will contain or be the site for the phosphorylation. Likewise at the DNA level, it is only necessary that the codons be provided which code for the amino acids which will be recognized by the kinase. Lack of absolute substrate specificity which has been reported to be a general property of protein kinases (21, 100), may provide further latitude in the selection of nucleotide sequences, or the codons coding for the recognized amino acids.

By "incorporates", "incorporation" or "insertion" or equivalent term, it is not necessary that the amino acid recognition sequence (or the nucleotide sequence coding for that amino acid sequence (or part thereof) be actually within the desired protein (or the nucleotide sequence coding therefor); it is sufficient that it be part of the modified protein, or part of the nucleotide sequence (or of part thereof) coding for the modified product.

A specific embodiment of the concept of the invention is a genetically engineered Hu-IFN-αA of the invention which, unlike the known Hu-IFN-αA (native, natural or genetically engineered), is phosphorylatable and the phosphorylated modified Hu-IFN-α. The phosphorylated Hu-IFN-αA-P has retained biological activity with high radio-specific activity (2,000–12,000 Ci/mmol). Phosphorylation was performed with the catalytic bovine heart kinase which is a cyclic AMP (cAMP)-dependent kinase. The amino acid recognition (or consensus) sequences for the cAMP-dependent protein kinase have been identified as Arg-Arg-Ala-Ser-Val (SEQ ID NO:2) and Arg-Arg-Ala-Ser-Leu (SEQ ID NO: 27) and Arg-Arg-Ala-Ser-Val-Ala (SEQ ID NO:28) amongst others (20, 21). In general cAMP-dependent protein kinases recognize the sequence Arg-Arg-Xxx-Ser-Xxx (21). The amino acid and nucleotide sequences of Hu-IFN-αA and their corresponding coding sequence have been reported (23–25).

Serine has been shown to be the target amino acid for phosphorylation for both the murine (5) and human (4, 10) IFN-gamma. It has also been shown that in Hu-IFN-gamma there are two serines capable of phosphorylation by the cAMP-dependent protein kinase, serines 132 and 142 (5, 10).

In accordance with the invention, in three specific illustrations of phosphorylated Hu-IFN-α (herein designated as Hu-IFN-αA-P1, -P2, and -P3), the carboxyl-terminal amino acids were modified to contain the phosphorylation sites, and the nucleotide sequences encoding the putative phosphorylation sites were constructed.

The modified interferons were constructed with the use of oligodeoxyribonucleotides designed to produce insertions and substitutions at the carboxyl terminus of Hu-IFN-αA by site-specific mutagenesis procedures (described in the literature and also further described below) with the appropriate DNA sequences inserted into phage M13mp19. The general methods used for synthesizing a Hu-IFN-α with a modified carboxyl terminus in $E.\ coli$ are further described in the following references (15, 26, 27).

It is not necessary that the amino acids at the carboxyl terminus be the ones that are modified; the modification can be at the amino terminal end of the sequence, and correspondingly can be towards the 5' end of the nucleotide sequence; the modification can be virtually at any position of the protein sequence (and corresponding coding region) as long as the phosphorylation site is recognizable by the kinase in the intact protein.

As illustrated above with respect to Hu-IFN-α, the introduction into nucleotide sequences of one or more putative sites encoding amino acid sequences recognizable by an enzyme like a protein kinase opens wide and important new possibilities for modifying proteins in which such sites are absent, or inaccessible, or into which it is desired to introduce such additional sites.

Amongst the protein kinases there are known cyclic nucleotide-dependent protein kinases which catalyze the transfer of the gamma-phosphate of ATP to serine and/or threonine hydroxyl groups of acceptor protein substrates, calcium-dependent protein kinases, tyrosine-specific protein kinases, cyclic nucleotide- and calcium-independent protein kinases. The invention contemplates the use of any of the protein kinases, the nucleotide sequences which code for one or more of the corresponding putative sites for phosphorylation and the modified protein containing the amino acid sequences recognizable by this selected protein kinase, and the phosphorylated protein containing the radio-label. Such label can be phosphorus, or sulfur, or other groups discussed herein. Also, it need not be a radio-label. It is sufficient that it be an "identifiable" label.

Broadly considered, the invention contemplates the phosphorylation of various proteins by protein kinases after the introduction of phosphorylatable sites. Thus, the wide applicability of the invention in providing appropriate sites for phosphorylation in proteins otherwise not phosphorylatable can be recognized.

Throughout this description of the invention, the terms "phosphorylatable" (or "phosphorylated") are used. Reference is also being made to the analogs of the phosphate donor ATP, such as the gamma thiophosphate analog. Through this description the term "phosphorylation" or like term is intended to be generic to include "thiophosphorylation" where for instance, $^{31}P$, $^{32}P$, or $^{33}P$ is replaced by $^{35}S$ or sulfur analogs.

As discussed herein, kinases have been reported to catalyze phosphorylation not only at serine but also at threonine or tyrosine (21, 22, 64). Thus, it is within the scope of the invention to construct the nucleotide sequence which codes for the putative site(s) of recognition for the kinase selected and, in a manner analogous to that described herein, construct the replicable expression vehicle, introduce it into an appropriate host which in turn will express the modified phosphorylatable protein. In appropriate cases, the modified phosphorylatable protein is exogenous and mature. The phosphorylatable proteins can then be phosphorylated. Of course likewise, analogs of phosphorylated proteins—e.g., sulfur-labelled—can be made.

The nucleotide sequence encoding the putative phosphorylation site in the case of modified Hu-IFN-α which is recognized by the cAMP-dependent protein kinase is created by the oligodeoxyribonucleotide-directed insertion on the level of DNA as shown in FIG. 9.

Construction of the Modified Interferons

The construction of expression plasmids for Hu-IFN-α containing phosphorylation sites was carried out as follows. The EcoRI-PstI fragment from pIFLrA that contained the coding sequence for Hu-IFN-αA (23, 24) was inserted into the EcoRI-PstI site of M13mp19 to form M13BL27 that was used as the template for site specific alterations as shown in FIG. 9. To construct the coding sequences for Hu-IFN-αA-P1 and P2, two oligodeoxyribonucleotides were synthesized to anneal to M13BL27 with the formation of a loop that permits the insertion of nucleotides to generate a coding sequence for a phosphorylation site at the COOH-terminal end (boxed residues, FIG. 8). The oligonucleotides used to prepare Hu-IFN-αA-P1 and -P2, respectively, were: AGT-TTA-AGA-AGT-AAG-AGA-AGG-GCA-AGT-GTT-GCA-TGA-AAA-CTG-CTT-CAA (SEQ ID NO:29); and ACA-AAC-TTG-CAA-AGA-AGT-TTA-AGA-AGG-GCA-AGT-TTA-GCA-TGA-AAA-CTG-CTT-CAA (SEQ ID NO:30). The underlined nucleotides are homologous with the coding sequence and 3' noncoding nucleotide sequence of the cDNA encoding Hu-IFN-αA; the nucleotides not underlined produce a loop for the insertion of additional residues for P1 and P2. A site-specific mutation as well as an insertion was introduced with the P2 oligonucleotide. After annealing of the oligonucleotide to single-stranded DNA from M13BL27, the second strand was synthesized and then cut with restriction, endonucleases EcoRI-PstI. The EcoRI-PstI fragment obtained was then reinserted into the EcoRI-PstI site of phage M13mp19 as shown in FIG. 9, and then E. coli were transformed with the duplex DNA. Incomplete duplexes (upper right of FIG. 9) do not yield the PstI-EcoRI duplex fragment. This excision and religation step was introduced to increase the efficiency of the site-specific mutations providing an overall yield of about 400 positive clones. RF DNA samples, prepared from individual phage M13 plaques, were screened for the presence of the inserted EcoRIPstI fragment. Positive clones (i.e., those with insertions; about 75–90% of the plaques), were sequenced by the known Sanger dideoxynucleotide procedure (68) to identify the proper mutated recombinant and to confirm the sequence. By this procedure, about 50% of the transformants sequenced contained the mutated coding sequence with the phosphorylation site. The EcoRI-PstI fragments were then excised from the respective RF DNA preparations from the phages (M13BL28, M13BL29 and M13BL30) and religated into the EcoRIPstI site of pRC23t to yield the expression vectors pBL281, pBL291 and pBL301 as shown in FIG. 9. The two EcoRI-PstI fragments originating from pRC23t were obtained by restriction endonuclease digestion of an expression plasmid for Mu-IFN-β that contained the trp terminator just downstream from the IFN-β coding sequence.

During the construction of the Hu-IFN-αA-P1 expression vector, a clone was isolated with a duplication of the -P1 oligonucleotide, a single nucleotide deletion of one A of codon 164 for Lys, and a second deletion of 11 3'-terminal residues (AA-CTG-GTT-CAA) (SEQ ID NO:31) from the downstream -P1 oligonucleotide. This series of steps generated an in-phase coding sequence for a new phosphorylation site on a slightly larger molecule designated Hu-IFN-αA-P3 (FIGS. 8 and 9).

The general recombinant DNA procedures employed herein have been described elsewhere (15, 26, 27). These methods are incorporated herein by reference. The use of vectors containing the phage lambda P. promoter for cloning of recombinants and expression of proteins has been described by a number of laboratories (12, 48, 49, 70–77). A variety of E. coli strains lysogenic for wild type and mutant phage lambda or containing plasmids encoding the phage lambda repressor (12, 15, 48, 49, 70–78) have been used for growth of plasmids and/or expression of plasmid encoded proteins. For example, the following E. coli strains among others have been used for replication of plasmids and/or for expression of proteins under control of the phage lambda $P_L$ promoter: E. coli 294 (75; ATCC #31977), AR 13 (77), AR58 (77), AR68 (75), AR120 (77, 74), C600 (49, 71; ATCC #33766), N99 (72; CC #433956), RR1 (66, 70; ATCC #31343), W3110 (77). With E. coli strains carrying a temperature-sensitive repressor (cI857), the cells can be grown at 30° C. to prepare plasmids; upon shifting the temperature to 42° C., the repressor is inactivated and the DNA sequence under control of the phage lambda $P_L$ promoter expressed (49, 66, 70–73, 75). Thus, cells can be grown to a high density at 30° C., then induced to express the protein of interest at 42° C. Alternatively, with the use of wild type phage lambda repressor (cI⁻), nalidixic acid can be used to induce expression of genes under control of the phage lambda $P_L$ promoter (77). In the work involving this invention, it has been found desirable to use the temperature sensitive repressor (cIts857) to regulate expression of the genes under control of the phage lambda $P_L$ promoter. Although it was not found necessary to use protease deficient strains to achieve high production of recombinant proteins in E. coli (49, 70, 74, 77), strains lacking proteases (79, 80, 81) might prove beneficial in some cases (75, 76).

Construction and identification of bacterial plasmids containing the nucleotide sequence for Hu-IFN-αA is described in references 23 and 24. The reports describe the isolation of recombinant plasmids carrying DNA sequences corresponding to Hu-IFN-α species. The E. coli strain K-12 derivative RR1 can be considered a useful host in the present invention.

Site-specific mutagenesis which is well-suited for the present purposes is described in the following citations (15, 26, 27 and 43 at unit 8, supplement 2), which are incorporated herein by reference. The background of the method is reviewed in reference 44. A description in the patent literature is found in U.S. Pat. No. 4,751,077, which is also incorporated herein by reference.

In accordance with the invention, the nucleotide sequence coding for the amino acid consensus sequence (which will contain the putative phosphorylation site) may be inserted anywhere into the nucleotide sequence of Hu-IFN-αA. This can be observed from the oligonucleotide sequences shown in FIG. 8. However, the insertion of the nucleotide sequence is preferably made at a site in the nucleotide sequence encoding Hu-IFN-αA so as to minimize an undesirable effect on the biological activity of the resultant recombinant protein, when such biological activity is critical.

The Expression of Hu-IFN-αA-P by Bacteria

The expression of the modified interferons in E. coli transformed with the expression plasmids encoding the Hu-IFN-αA-P proteins and the purification of Hu-IFN-αA-P proteins were carried out as follows. Each of the three above-named vectors was introduced into E. coli cells containing the plasmid pRK248cIts857. E. coli AR68 cells and E. coli RR1 cells containing the compatible plasmid pRK248cIts857 harboring each of the pBL281, pBL291 and pBL301 plasmids expressed Hu-IFN-αA-P1, -P2, and -P3, respectively, under control of the $P_L$ promoter and trp terminator at 42° C. The yields of Hu-IFN-αA-P1, -P2, and -P3 in E. coli AR68(pRC248) were higher than that in E. coli RR1(pRK248) harboring the same plasmids. The products expressed in *E. coli* AR68 at 42° C. were used to purify the Hu-IFN-αA-P1, -P2, and -P3 proteins by immunoaffinity chromatography as described further below. The data in Table 1 (below) show that greater than 50% of the antiviral activity was recovered. Hu-IFN-αA-P1, -P2, and -P3 were purified to a specific activity of $1.2 \times 10^8$, $1.1 \times 10^8$ and $1.5 \times 10^8$ units per mg protein, respectively.

Plasmid pBL281 is deposited with the ATCC under Accession number 40509, and designated as pHu-IFN-αA-P1.

TABLE 1

Purification of Hu-IFN-αA-P Proteins

| Human IFN-αA | Step | Antiviral activity Total units | Yield (%) | Protein mg | Specific Activity units/mg | Purification factor |
|---|---|---|---|---|---|---|
| αA-P1 | 1 | $1.6 \times 10^7$ | 100 | 32.6 | $4.9 \times 10^6$ | 1 |
|  | 2 | $1.8 \times 10^7$ | 113 | 18.4 | $9.9 \times 10^6$ | 2 |
|  | 3 | $1.1 \times 10^7$ | 71 | 0.09 | $1.2 \times 10^6$ | 246 |
| αA-P2 | 1 | $1.6 \times 10^7$ | 100 | 34.3 | $4.7 \times 10^6$ | 1 |
|  | 2 | $1.2 \times 10^7$ | 75 | 12.9 | $9.3 \times 10^6$ | 2 |
|  | 3 | $0.9 \times 10^7$ | 56 | 0.08 | $1.1 \times 10^6$ | 232 |
| αA-P3 | 1 | $1.6 \times 10^7$ | 100 | 33.0 | $4.8 \times 10^6$ | 1 |
|  | 2 | $1.8 \times 10^7$ | 113 | 15.0 | $1.2 \times 10^6$ | 2.5 |
|  | 3 | $2.6 \times 10^7$ | 163 | 0.18 | $1.5 \times 10^6$ | 312 |

The characterization of Hu-IFN-αA-P and its $^{32}$P-labelled product was carried out as follows. The purified Hu-IFN-αA-P1, -P2, -P3 proteins were analyzed by SDS-polyacrylamide gel electrophoresis in the presence of 2-mercaptoethanol (FIG. 10). A single band was observed on the silver stained gel with Hu-IFN-αA-P1 or -P2. Hu-IFN-αA-P2 migrated slightly faster than Hu-IFN-αA-P1 and a little slower than Hu-IFN-αA. Hu-IFN-αA-P3 yielded two bands, the slower migrating band being the intact molecule.

Hu-IFN-αA-P1, -P2 and -P3 were phosphorylated by the cAMP-dependent protein kinase with [gamma-$^{32}$P]ATP to a specific radioactivity of 2,000–12,000 Ci/mmol. Following phosphorylation, [$^{32}$P)Hu-IFN-αA-P1 and -P2 migrate on SDS-polyacrylamide gel electrophoresis in the presence of 2-mercaptoethanol as a single band with an apparent molecular weight of 19,000–20,000 (FIG. 11) corresponding to the same positions as the silver stained unlabelled band. The labelled Hu-IFN-αA-P3 migrates slower than the -P1 or -P2 products as expected. Since the faster migrating P3 band is unlabelled (cf. FIGS. 10 and 11), it is likely that the COOH-terminal extension of -P3 that contains the phosphorylation site is trimmed from the full length product to yield the faster migrating form. Unlabelled Hu-IFN-αA and ([$^{125}$I]Hu-IFN-αA were used as molecular weight standards and controls (FIGS. 10 and 11).

Antiviral Activity of the New Interferons

The effect of phosphorylation on the antiviral activity of Hu-IFN-αA-P1, -P2, and -P3 was determined in a parallel experiment. Phosphorylation, it was found, has little or no effect on the antiviral activity of the Hu-IFN-αA-P1, -P2, and -P3 measured with both bovine MDBK cells and human WISH cells.

Table 2, below shows the antiviral activity of non-phosphorylated and phosphorylated interferon alpha proteins.

TABLE 2

Effect of Phosphorylation on the Antiviral Activity of Phosphorylated Human Interferon Alpha Proteins

| Human IFN-αA | [gamma-$^{32}$P]ATP | Antiviral Activity MDBK | WISH |
|---|---|---|---|
| αA-P1 | − | $1.6 \times 10^6$ | $4.0 \times 10^6$ |
|  | + | $1.6 \times 10^6$ | $2.4 \times 10^6$ |
| αA-P2 | − | $1.6 \times 10^6$ | $8.8 \times 10^6$ |
|  | + | $0.9 \times 10^6$ | $8.8 \times 10^6$ |
| αA-P3 | − | $6.4 \times 10^6$ | $4.8 \times 10^6$ |
|  | + | $4.8 \times 10^6$ | $3.2 \times 10^6$ |

Ability to Bind to Receptors

The ability of [$^{32}$P]Hu-IFN-αA-P to bind to receptors was shown as follows. [$^{32}$P]Hu-IFN-αA-P1 and -P2 bind to bovine MDBK and human Daudi cells (FIG. 12) with the specific binding approaching saturation at higher concentrations. Scatchard analysis of the data yielded the following estimates. The bovine MDBK cells contain approximately 3,800 and 9,450 receptors per cell calculated from the binding of [$^{32}$P]Hu-IFN-αA-P1 and -P2, respectively; Daudi cells, approximately 1,650 and 4,900 receptors per cell. Dissociation constants ($K^1$) were calculated to be $1.4 \times 10^{-10}$ M for the binding of [$^{32}$P]Hu-IFN-αA-P1 to both the human and bovine cells; and $3.5 \times 10^{-10}$ M and $2.2 \times 10^{-}$ M for the binding of [$^{32}$P]Hu-IFN-αA-P2 to human and bovine cells, respectively. Similar results are obtained with [$^{32}$P]Hu-IFN-αA-P3.

All these phosphorylated [$^{32}$P]Hu-IFN-αA-P derivatives bind to the Hu-IFN-α/β receptor because their binding to Daudi cells was competitively blocked by Hu-IFN-αA and Hu-IFN-β, but not by Hu-IFN-gamma.

Crosslinking of [$^{32}$P]Hu-IFN-αA-P to the Receptors

The crosslinking of [$^{32}$P]Hu-IFN-αA-P to the receptors was carried out as follows. [$^{32}$P]Hu-IFN-αA-P1, -P2, and -P3 were each covalently crosslinked to the receptors by reaction with disuccinimidyl suberate after binding to the cells (FIG. 13). The radioactive complexes migrate as several bands with molecular weights of 100K–200K from the Daudi cells or as a broad band with an apparent molecular weight of about 150K from the KOBK cells upon analysis by SDS-polyacrylamide gel electrophoresis. The crosslinked complexes of the receptors on the cells with [$^{32}$P]Hu-IFN-αA-P1, -P2, and -P3 appear to be the same on SDS-polyacrylamide gels, but differ from the crosslinked complexes of [$^{32}$P]Hu-IFN-gamma formed with human Daudi cells. Neither the crosslinked complexes nor the free [$^{32}$P]Hu-IFN-αA-P1, -P2, and -P3 are seen if excess non-radioactive Hu-IFN-αA is included during the binding reaction (FIGS. 12 and 13).

Hu-IFN-β Containing A Phosphorylation Site

Likewise nucleotide sequences coding for a Hu-IFN-β-like protein, which sequence contains a putative phosphorylation site recognizable by the cAMP-dependent protein kinase, is prepared.

The following procedure generates a modified Hu-IFN-β containing a site recognizable by the cAMP-dependent protein kinase from bovine heart. The PstI-BglII 363 bp fragment from the cDNA encoding Hu-IFN-β is excised from the expression vector pFIFtrp69 (104). The 363 bp fragment is inserted into the PstI and XmaI sites of phage M13mp18. First the PstI end of the PstI-BglII fragment is ligated to the dsDNA of M13mp18 cut with restriction endonucleases PstI and XmaI. The BglII end of the fragment is then ligated to the M13mp18 vector with the use of a BglII-XmaI linker:

GATCTGCGCGCG ACGCGCGCGGGCC (SEQ ID NO:32)

which reconstructs BglII and XmaI sites. Since there is no BglII site in the polylinker region of M13mp18, this BglII-XmaI linker is used to preserve the BglII site and permit cutting with XmaI for preparation of one of the intermediate recombinants (see below and analogous construction in FIG. 8). The M13mp18 containing the 363 bp fragment from the 5' end of the coding region of Hu-IFN-β formed M13-A that is used as a template for site specific mutation as follows. The site specific insertion is made similarly to that described above for construction of Hu-IFN-αA-P1. To construct the coding sequence for Hu-IFN-β-P, the modified Hu-IFN-β, a oligodeoxyribonucleotide (CTT-ACA-GGT-TAC-CTC-CGA-AGG-GCA-AGT-GTT-GCA-TGA-AGA-TCT-GCG-CGC-GCC-CGG) (SEQ ID NO:33) is synthesized to anneal to M13-A with the formation of a loop that would permit the insertion of nucleotides to generate a coding sequence for a phosphorylation site at the COOH-terminal end. The underlined residues of the oligonucleotide shown above are homologous with the nucleotides of the phage M13-A that contains the cDNA fragment encoding Hu-IFN-β. A comparison of Hu-IFN-8 and Hu-IFN-β-P is shown below:

The phosphorylatable modified interferon is expressible as described (104), and can be purified following the procedure for the corresponding Hu-IFN-β (65).

The following illustrative examples are not intended to limit the invention in any manner whatsoever.

ILLUSTRATIVE EXAMPLES

Bacterial Strains, Enzymes and Chemicals. E. coli RR1 containing the plasmid pRK248cIts857 with the temperature-sensitive repressor of the phage lambda $P_L$ promoter, was obtained from Robert Crowl (12). The plasmid pPRK248cIts857 was introduced into E. coli AR68 (75) by transformation.

Restriction endonucleases and polynucleotide kinase were from New England BioLabs. The buffer conditions used were described by the manufacturer. The Klenow fragment of Escherichia coli DNA polymerase I and T4 DNA ligase were from International Biotechnologies, Inc.; calf intestinal phosphatase (c.i.p.) was from Boehringer-Mannheim Biochemicals. Ligation reactions were carried out in the presence of low melting point agarose gel (15, 66).

The catalytic subunit of cAMP-dependent protein kinase from the bovine heart muscle with a specific activity of 20,000 units/ml was obtained from Sigma. (Gamma-$^{32}$P] ATP with specific radioactivity of 5,000 Ci/mmol was obtained from Amersham; dithiothreitol (DTT), from Bethesda Research Laboratories; bovine serum albumin (BSA), from Miles Laboratories; acrylamide and N,N'-methylenebisacrylamide, from International Biotechnologies, Inc. (IBI); sodium dodecylsulfate (SDS), from Sigma; and disuccinimidyl suberate (DSS), from Pierce Chemical Co.

```
              160                 165
Hu-IFN-β      Leu-Thr-Gly-Tyr-Leu-Arg-Asn-END              (SEQ ID NO:35)
              CTT-ACA-GGT-TAC-CTC-CGA-AAC-TGA              (SEQ ID NO:34)

160                 165             170
Hu-IFN-β-P    Leu-Thr-Gly-Tyr-Leu-Arg-Ala-Ser-Val-Ala-END  (SEQ ID NO:37)
              CTT-ACA-GGT-TAC-CTC-CGA-AGG-GCA-AGT-GTT-GCA-TG (SEQ ID NO:36)
```

The underlined residues of the modified Hu-IFN-β-P from 165–170 represent the cAMP-dependent protein kinase recognition site. The nucleotides of the oligonucleotide above that are not underlined produce a loop for the insertion of residues 166–170 of Hu-IFN-β-P. After annealing of the oligonucleotide to single-stranded DNA from M13-A, the second strand is synthesized and then cut with restriction endonucleases PstI and XmaI. The resultant PstI-XmaI fragment is then reinserted into the PstI-XmaI site of phage M13mp18 as shown analogously in FIG. 8 and then E. coli are transformed with the duplex DNA. This excision and religation step is introduced to increase the efficiency of the site-specific mutations. RF DNA preparations from individual phage M13 plaques are screened for the presence of the inserted PstI-XmaI fragment. Positive clones (i.e. those with insertions) are sequenced by the Sanger dideoxynucleotide procedure (68) to identify the proper mutated recombinant and to confirm the sequence. By this procedure, several transformants sequenced contain the mutated coding sequence with the phosphorylation site (M13-B). The PstI-BglII fragment is then excised from the RF DNA from phage M13-B and religated into the PstI-BglII site of pFIFtrp69 to yield the expression vector similar to the original vector. The general recombinant DNA procedures employed have been described elsewhere (15, 26, 27, 43).

Interferon and Protein Assays. Interferon activity was determined by a cytopathic effect inhibition assay with vesicular stomatitis virus and bovine MDBK cells (13). All interferon titers are expressed in reference units/ml calibrated against the reference standard for human leukocyte interferon (G-023-901-527) obtained from the Antiviral Substances Program of the National Institute of Allergy and Infectious Diseases, National Institutes of Health, Bethesda, Md. Protein concentration was determined by the procedure of Bradford (14) with bovine serum albumin as a standard.

The following illustrates the preparation of the fused-hybrid Hu-IFN-αA/gamma.

Synthesis and Phosphorylation of Oligonucleotide

The oligodeoxyribonucleotide CTGACTC-CTTTTTCGCTTTTCCTFACTTCTTAAC (SEQ ID NO:38) which was used for oligonucleotide-directed mutagenesis and hybridization screening was synthesized and phosphorylated as described (66). After the phosphorylation reaction, the reaction mixture was diluted with 3.5 ml of 6×SSC (0.9 M NaCl, 90 mM sodium citrate) and used directly for screening by hybridization.

Oligonucleotide-directed Deletion. About 100 pmoles of phosphorylated oligomer were annealed with 1 pmole of ssDNA template in 10 μl of 30 mM Tris-HCl, pH 7.5, 10 mM MgCl, at 80° C. for 5 min. and gradually cooled to 30° C. for 30 min., then put on ice. The volume was adjusted to 20 μl of 30 mM Tris-HCl, pH 7.5, 10 mM MgCl$_2$, 0.5 mM dATP, 0.5 mM dCTP, 0.5 mM dGTP, 0.5 mM dTTP, 1 mM ATP, 10 mM dithiothreitol (DTT). The oligomer was extended with 2.5 units of the Klenow fragment of DNA polymerase I in the presence of 6 units of T4 DNA ligase at 16° C. for 24 hr. The reaction mixture was then extracted once with an equal volume of phenol and chloroform (1:1) and precipitated with 1/10 volume of 2.5 M sodium acetate and 2 volumes of 95% ethanol. After washing with 75% ethanol, DNAs were digested with SpeI for the enrichment of the mutated DNA before transformation of RR1(lambda-cIts857). For screening, the colony hybridization method was used as described (58, 67). DNA sequencing was performed by the dideoxy sequencing method (68) after the 600 bp HincII/PstI fragment from M13mp18/Hu-IFN-αA/gamma was inserted into the HincII and PstI site of M13mp19.

Preparation and Purification of Hu-IFN-αA/gamma. E. coli RR1(pRK248cIts857) cells harboring Hu-IFN-αA/gamma were grown in LB broth at 30° C. overnight. An overnight culture of 40 ml was diluted to 2,000 ml of M9 medium containing 0.4% of casamino acids, 50 μg/ml ampicillin (Ap) and 25 μg/ml tetracycline. Bacteria were grown at 30° C. until the cell density at 600 nm reached 1.0, at which time the cells were transferred to 42° C. for 2–3 hrs. The cells were collected by centrifugation at 7,000 rpm for 10 min. and stored at −20° C. until used.

For purification, all steps were carried out at 4° C. Frozen cells (10 g) were suspended in 3 volumes (40 ml) of 7 M guanidine hydrochloride in 25 mM Tris-HCl, pH 7.5. The suspension was mixed for 1 hr. and centrifuged at 17,000 rpm for 30 min. The supernatant was diluted into 10 volumes of phosphate buffered saline (PBS). Solid ammonium sulfate was added to 65% saturation with vigorous stirring. The suspension was kept at 4° C. for 2 hrs. and then centrifuged at 10,000 rpm for 20 min. The pellet was suspended in 20 ml of PBS and dialyzed extensively against PBS.

The suspension obtained was centrifuged at 10,000 rpm for 20 min., and the supernatant was mixed with 0.3 ml of monoclonal antibody to Hu-IFN-αA (LI-8) coupled to Affi-gel k10 (16, 41) for 1 hr. The mixture was then loaded into a 1-ml disposable syringe. After washing with four column volumes (0.3 ml) of 0.5 M NaCl, 25 mM Tris-HCl, pH 7.5, the column was rinsed with four column volumes of 0.15 M NaCl and then eluted with four column volumes of 0.2 N acetic acid and 0.15 M NaCl, pH 2.5. Antiviral activity was eluted in the first two fractions. It was measured by a cytopathic effect inhibition assay on bovine MDBK cells (13). The concentration of protein was determined by the procedure of Lowry (69) or Bradford (14) with bovine serum albumin as a standard. The concentrations obtained by the two procedures were in agreement. The procedure yielded 240 μg of Hu-IFN-βA/gamma with a specific activity of 4×10$^8$ units/mg.

Preparation of Hu-IFN-αA/gamma protein from E. coli AR68(pRK248cIts857) harboring the expression plasmid pXZ-8 and its purification by immunoaffinity chromatography with monoclonal antibody against Hu-IFN-α is as described below for the Hu-IFN-α-P proteins. The yield from 50 ml of bacterial culture was 388 μg of Hu-IFN-αA/gamma with a specific activity of 2.3×10$^7$ units/mg. The procedure of purification by immunoaffinity chromatography with monoclonal antibody against the COOH-terminal sequence of Hu-IFN-gamma is the same as above. Elution with acid yielded 281 μg of Hu-IFN-αA/gamma with a specific activity of 1.3×10$^7$ units/mg from 50 ml of bacterial culture.

Phosphorylation of Hu-IFN-αA/gamma. Hu-IFN-αA/gamma was phosphorylated as described for Hu-IFN-gamma (3, 6) with some minor modifications. About 1 μg of Hu-IFN-αA/gamma was incubated at 30° C. for 60 min. with 0.5 mCi of [gamma-$^{32}$P]ATP (>5,000 Ci/mmol, Amersham Corp.) and 10 units of the catalytic subunit of bovine heart cAMP-dependent protein kinase (Sigma) in 30 μl of 20 mM Tris-HCl, pH 7.4, 100 mM NaCl, 12 mM MgCl$_2$, and 3 mM DTT, then cooled on ice to stop the reaction. After addition of 0.3 ml of 5 mg/ml bovine serum albumin in 10 mM sodium pyrophosphate, pH 6.7, the reaction mixture was dialyzed extensively against 10 mM sodium pyrophosphate, pH 6.7, at 4° C. Incorporation of radioactivity into Hu-IFN-αA/gamma was measured with a liquid scintillation spectrometer after precipitation of the protein with trichloroacetic acid (82).

Binding of Hu-IFN-αA/gamma to cells. Bovine MDBK cells were used for binding studies. MDBK cells were grown to confluence in 6-well tissue culture plates in medium (Gibco F-11) supplemented with 10% fetal calf serum and 50 μg/ml gentamicin. Medium was removed, and 1 ml of fresh medium was added into each well. After 20 min., [$^{32}$P]Hu-IFN-αA/gamma was added in the absence or presence of V0.6 μg unlabelled Hu-IFN-αA (10$^8$ units/mg). Following incubation at room temperature for 1 hr., the plates were put on ice and each well was washed with three 1 ml volumes of cold PBS. Then 1 ml of 1% SDS was added to remove cells from the wells. Radioactivity was determined with a liquid scintillation counter by placing the 1 ml samples in 10 ml of a scintillation fluor (83). Binding of [$^{32}$P]Hu-IFN-αA/gamma to the human Daudi cells is described below with the Hu-IFN-αA-P proteins.

The following illustrates the construction of modified interferons by "insertion".

Construction of Modified Interferons. Because of certain limitations of the hybrid-fusion procedure and product as discussed above, an alternative construction was explored. It was then discovered that a putative phosphorylation site could be introduced into a nucleotide sequence of Hu-IFN-α.

The amino acid recognition or consensus sequences for the cAMP-dependent protein kinase have been identified as Arg-Arg-Ala-Ser-Val (SEQ ID NO:2) and Arg-Arg-Ala-Ser-Leu (SEQ ID NO:27) among others (20, 21). The amino acid sequence of Hu-IFN-αA and its corresponding coding sequence have been reported (23–25). Hu-IFN-αA as well as other interferons have been expressed in E. coli expression vectors under control of the trp and the phage lambda P. promoter (see references 1, 24 and 25 for reviews and additional citations). The terminal nucleotides corresponding to the last ten carboxyl-terminal amino acids of Hu-IFN-αA are shown in FIG. 8 as well as sequences corresponding to modified molecules, Hu-IFN-αA-P1, -P2, and -P3, which contain putative phosphorylation sites. To construct these molecules oligodeoxyribonucleotides were synthesized to introduce the insertions and substitutions shown at the carboxyl terminus of Hu-IFN-αA (FIG. 8) by site-specific mutagenesis procedures with the appropriate DNA sequences inserted into phage M13mp19 (15, 26, 27). The phosphorylation sites in Hu-IFN-αA-P 1, -P2, and -P3 (FIG. 8) recognized by the cAMP-dependent protein kinase were created by the oligodeoxyribonucleotide-directed insertion on the level of DNA as shown in FIG. 8.

The expression plasmids pBL281, pBL291 and pBL301, coding for Hu-IFN-αA-P1, -P2, and -P3, respectively, were constructed as outlined in FIG. 8. The sequences coding for the modified interferons were inserted into an expression vector under control of the phage lambda $P_L$ promoter also as illustrated in FIG. 8. *E. coli* AR68 containing the compatible plasmid pRK248cIts857 was transformed with each of the expression plasmids encoding the Hu-IFN-αA-P proteins containing the COOH-terminal sequences shown in FIG. 8. The phosphorylatable modified interferons were expressed and purified as described further below.

Expression and Preparation of Hu-IFN-αA-P. *E. coli* RR1 (pRK248cIts857) cells harboring pBL281, pBL291 or pBL301 plasmids containing the Hu-IFN-αA-P1, -P2, and -P3 coding sequences were grown at 30° C. overnight in M9CA medium (15) with the concentration of some components modified as follows: 1% casamino acids, 1% glucose, 10 mM $MgSO_2$ and 1 mM $CaCl_2$, and containing 2 μg/ml thiamine, 50 μg/ml ampicillin and 12.5 μg/ml tetracycline. For expression of Hu-IFN-αA and modified proteins, 100 ml of M9CA medium was inoculated with 3–5 ml of an overnight culture. The bacteria were grown at 30° C. until the cell density reached an optical density at 600 nm of 0.3–0.5 in 2–3 hours, at which time the culture was transferred to 42° C. for an additional two hours. The bacterial cells were collected by centrifugation and lysed in 8 M guanidine hydrochloride and 50 mM Tris-HCl, pH 7.6, at 0° C. for 10 min. The supernatant obtained after centrifugation at 14,000 rpm (SA-600 Sorvall rotor) for 30 min. was used to assay the antiviral activity or to purify the Hu-IFN-αA and modified interferons.

*E. coli* AR68(pRK248cIts857) cells harboring plasmids pBL281, pBL291, or pBL301 containing Hu-IFN-αA-P, coding sequences were grown in LB medium (15) containing 50 μg/ml ampicillin and 12.5 μg/ml tetracycline at 32° C. overnight. The overnight culture was diluted five-fold with fresh LB medium containing the same concentration of antibiotics as above and then grown at 32° C. for 2–3 hours. For expression of the Hu-IFN-αA-P proteins, harvesting of cells, and preparation of supernatants the procedures described above for use with *E. coli* RR1 cells were used.

The purification of Hu-IFN-αA-P proteins were carried out as follows. All steps for purification of Hu-IFN-αA-P species were carried out at 4° C.–8° C. Ten ml of the guanidine hydrochloride supernatant from 100 ml of the expressed culture were diluted ten-fold with cold phosphate-buffered saline (PBS) and precipitated at 65% saturation of ammonium sulfate at 4° C. overnight. The precipitate was collected by centrifugation at 10,000 rpm (Sorvall GSA rotor) for 20 min. at 5° C. The supernatant was decanted and saved. The residual pellet was dissolved again in 10 ml of cold PBS and the solution centrifuged as above. The combined supernatants of 30 ml were mixed with i mi of Affi-gel 10 to which monoclonal antibody LI-8 (against Hu-IFN-α) was linked (16, 41) and the suspension rocked at 4° C. for 1 hour. The immunoabsorbent was loaded into the barrel of a 2 ml disposable syringe and washed with 20 column volumes or more of each of the following cold solutions sequentially (16): PBS, Buffer F (0.5 m NaCl, 25 mM Tris-HCl, pH 7.5, and 0.2% Triton X-100); and 0.15 M NaCl. Then the interferon was eluted with Buffer H (0.2 M acetic acid, 0.15 M NaCl, pH 2.6) and 0.4 ml fractions collected. The eluted fractions were neutralized with 1 M Tris base to pH 7.0 and the fractions of peak antiviral activity pooled.

The phosphorylation of Hu-IFN-gamma and Hu-IFN-αA-P proteins was carried out as follows: Hu-IFN-αA-P or Hu-IFN-gamma were labelled with [gamma-$^{32}$P]ATP and the cAMP-dependent protein kinase as described for Hu-IFN-gamma with some minor modifications (3, 6).

About 0.25 to 0.65 μg of Hu-IFN-gamma or Hu-IFN-αA-P was incubated at 30° C. for 1 hour with 0.25 mCi of [gamma-$^{32}$P]ATP (5,000 Ci/mmol, Amersham) and 7.5 units of the catalytic subunit of cAMP-dependent protein kinase in 30 μl containing components as previously reported (3, 6). The reaction mixture was then cooled in an ice bath, and, after the addition of 270 μl of 5 mg/ml bovine serum albumin in 10 mM sodium pyrophosphate (NaPPi), pH 6.7, was dialyzed extensively against 10 mM NaPPi at 4° C. The radioactivity associated with [$^{32}$P]Hu-IFN-αA-P was determined in a Beckman Model-LS3801 scintillation spectrometer. The phosphorylated Hu-IFN-αA-P was stored in liquid nitrogen in small volumes.

It has been reported (6) that the Hu-IFN-gamma phosphorylated with $^{32}$P has a 100-fold higher specific radioactivity than reported for [$^{125}$I]IFN-gamma.

The phosphorylated interferons in accordance with the invention provides molecules with higher radio-specific activity than previously obtainable (1,000–12,000 Ci/mmol) with retention of biological activity. Thus, the phosphorylation site inserted into Hu-IFN-αA at the COOH terminus does not detrimentally affect the biological activity (antiviral activity) and can be effectively recognized by the cAMP-dependent protein kinase.

Further Hu-IFN-αA-P1 and -P2 are stable during purification and phosphorylation. The Hu-IFN-αA-P3, which as shown in FIG. 8 has an additional septidecylpeptide at the COOH terminus, degraded into at least two fragments.

It is evident that for some biological applications the phosphorylated modified interferons, and those labelled with phosphate analogs such as those containing S, should be stable in serum.

The binding of [$^{32}$P]Hu-IFN-αA-P1, -P2, and -P3 to bovine MDBK cells and human Daudi cells was performed. [$^{32}$P]Hu-IFN-αA-P1, -P2, and -P3 crosslinked to cells exhibited one complex of about 150K with the bovine MDBK cells and several complexes of 100–200K with the human Daudi cells.

The binding of [$^{32}$P]Hu-IFN-αA-P to cells was performed as follows: Confluent monolayers of bovine MDBK cells were trypsinized and 1 ml (1×$10^6$ cells) of the cell suspension in Dulbecco's modified Eagle's medium (Gibco) containing 10% inactivated fetal calf serum and 1% penicillin-streptomycin solution (Gibco) was added to each well of a 6-well plate. The cell monolayers reached confluence and approximately doubled on overnight incubation at 37° C. at which time they were used to measure binding of [$^{32}$P]Hu-IFN-αA-P. For beginning the binding, the medium was removed, then 1 ml of fresh medium containing [$^{32}$P]Hu-IFN-αA-P at the indicated concentration was added into each well in the absence (−) or presence (+) of excess nonradioactive Hu-IFN-αA as a competitor (>500-fold more than [$^{32}$P]Hu-IFN-GA-P added). The plates were incubated with rocking at room temperature (24° C.) for 60 min., after which they were placed on ice to cool. Each well was washed three times with 1 ml of cold PBS to remove the unbound radioactive ligand. After washing, 1.5 ml of 1% sodium dodecylsulfate in water was added to each well and, after dissolution of the cells and bound radioactivity, the entire 1.5 ml was counted in a Beckman Model LS3801 scintillation counter in 2 ml Hydrofluor scintillation fluid.

The binding of [$^{32}$P]Hu-IFN-GA-P to human Daudi cells was performed as described previously (17) with some modifications. Daudi cells were harvested by centrifugation at 1,000×g for 10 min., washed twice with the growth medium (RPMI-1640, Gibco-H18, supplemented with 12.5 mM sodium HEPES, 10% fetal calf serum and 50 µg/ml gentamicin) and resuspended in the medium to a concentration of $1 \times 10^7$ cells/ml. The binding of [$^{32}$P]Hu-IFN-αA-P at the indicated concentration to $1.25 \times 10^6$ Daudi cells in a total volume of 125 µl was allowed to proceed in the absence or presence of non-radioactive Hu-IFN-αA as a competitor at room temperature (24° C.) for 60 min., with gentle resuspension every 15 min. At the end of the 60 min. incubation period, 100 µl of the cell suspension was layered onto a 300 µl cushion of 10% sucrose in PBS in a sample cup and pelleted by centrifugation (Beckman Microfuge Type B) for 2 min. Tubes were frozen in a dry ice-ethanol bath, and then the tips of tubes containing the cell pellets were cut off and counted as above. The specific binding at a given concentration of [$^{32}$P]Hu-IFN-αA-P is defined as the difference in bound radioactivity between samples incubated in the absence (total) and presence (nonspecific) of excess non-radioactive Hu-IFN-αA.

The covalent crosslinking of [$^{32}$P]Hu-IFN-αA-P to the receptors was carried out as follows: A monolayer of bovine MDBK cells in 75-cm$^2$ tissue culture flasks was washed twice with Dulbecco's phosphate-buffered saline, trypsinized with 2 ml of trypsin-EDTA solution (1× in phosphate-buffered saline, Gibco laboratories) At 37° C. until the cells were released from the tissue culture flask. After addition of 10–20 ml of Dulbecco's modified Eagle's medium (Gibco Laboratories) containing 10% inactivated fetal calf serum and 1% penicillin-streptomycin (Gibco), cells were collected by centrifugation at 500×g for 5–10 min. and resuspended in the same medium to a concentration of about $1 \times 10^7$ cells/ml. About $5 \times 10^5$ cpm of [$^{32}$P]Hu-IFN-α-A-P (2,000–12,000 Ci/mmol) was added to 0.5 ml of cells with or without 1 µg of non-radioactive Hu-IFN-αA as a competitor. After incubation with rocking at room temperature (24° C.) for 1 hour, the cells were pelleted for 20 seconds at 14,000 rpm in an Eppendorf Microfuge, washed twice with 1 ml of cold PBS, then treated with a final concentration of 0.5 mM disuccinimidyl suberate (freshly prepared in dimethylsulfoxide) at 4° C. for 20 min. as described (7). The crosslinking of [$^{32}$P]Hu-IFN-αA-P to cell receptor proteins was analyzed by sodium dodecylsulfate (SDS)-polyacrylamide gel electrophoresis (18) on 1.5-mm thick slab gels containing 8% acrylamide as described in detail previously (6, 7). The crosslinking thus was confirmed.

$^{35}$S-labelled proteins, like Hu-IFN-αA-P1, are obtainable in a manner similar to that described above.

SDS-polyacrylamide Gel Electrophoresis. The proteins, labelled products and covalent crosslinked complexes were analyzed by electrophoresis on the SDS-polyacrylamide slab gels of 1.0 or 1.5-mm thickness by the method of Laemmli (18). After electrophoresis, the proteins were stained with silver (19) or with Coomassie brilliant blue. Gels containing radioactive samples were dried under vacuum and autoradiographed at room temperature for the labelled ligands and at −170° C. for the covalent crosslinked complexes with Kodak X-Omat film and intensifying screens.

Other Expression Vectors, Host Cells, Etc. While presently preferred procedures to express the modified interferons, to make various nucleotide sequences, and to transform specific hosts have been illustrated, it is evident that the invention is not in any way limited by these illustrations. Both eukaryotic and prokaryotic host cells may be used. Several procedures for the isolation of genes and expression of interferons in bacterial cells and heterologous cells are quite well-suited for production of modified interferons of the invention. For instance, several such methods describe in reference (1) Section VII the use of yeast vectors for production (Chapter 59) of and secretion (Chapter 60) of human interferons by yeast. Other microbial strains of *E. coli* may be used, or Bacilli, like *Bacillus subtilis, Salmonella typhimurium* (as disclosed in U.S. Pat. No. 4,727,138) with plasmids that can replicate and express heterologous gene sequences therein. Other expression vectors are illustrated in U.S. Pat. No. 4,559,300, for instance. Numerous other promoter systems (than the one illustrated herein) can be used like the trp (104, 105) and lac (104, 106) promoters for example. All such references are included hereby by reference.

Likewise, the modified interferons can be produced from vertebrate cell cultures, for instance, a COS-7 line of monkey kidney fibroblasts can be used as the host for the production of the modified interferons with appropriate expression vectors (see Chapter 63 in reference 1, for example); other cell lines are suitable and are known. An example of the use of a retroviral based vector for expression in eukaryotic cells is given in Chapter 56 of reference 1. Many other examples of eukaryotic expression vectors have been described (see for example 50, 51, 84–90).

Vectors useful in the invention to replicate in a transformed host cell have a DNA segment containing a functional origin of replication (replicon). Plasmids and phage DNA by their very nature contain replicons facilitating replication in a host cell. The vector will have a DNA segment which conveys to a transformable host cell a property useful for selection of transformed cells from nontransformed cells. Any of a wide range of properties can be used for selection purposes. One of the most commonly used properties is antibiotic resistance, e.g., tetracycline resistance or ampicillin resistance.

The foregoing two elements generally are present in readily available and recognized cloning vectors. Examples of suitable cloning vectors are bacterial plasmids, such as plasmids from *E. coli*, including pBR322, pMB89, ColEl, pCRl; wider host range plasmids, including RP4; phage DNAs, such as lambda, and the like. Most, if not all, of the above-recognized vectors already la carry the aforedescribed two elements. Of course, as is known, in certain recombinants the DNA need not contain a replicon nor an attached marker.

Thus, any suitable expression vector may be used to express the modified interferons having putative phosphorylation sites in accordance with the invention.

In accordance with known procedures, the DNA comprises the regulating segments and the coding region. Thus, it is evident that the invention is not limited to the particular means of constructing genetic recombinants disclosed as illustrations and that one of average skill in the art would without undue experimentation adapt, change or select the procedures best suited to his objective.

For techniques and additional materials (vectors, host systems, plasmids, enzymes used in molecular cloning, synthesis and cloning of cDNA, introduction of plasmid and bacteriophage lambda DNA into *E. coli*, etc.), see (15) and (43), incorporated herein by reference.

ADDITIONAL GENERAL OBSERVATIONS

As has been described above, Hu-IFN-αA and Hu-IFN-β cannot be phosphorylated (by the cAMP-dependent bovine heart kinase) whereas it has been shown that Hu-IFN-gamma and the corresponding Ra- and Mu-IFN-gamma are amenable to phosphorylation without modification of the DNA-sequence (5, 11).

Thus, in accordance with the invention, additional phosphorylation sites can be introduced into Hu-IFN-gamma to provide interferon proteins that can be labelled to higher radio-specific activities than proteins, e.g., interferons, with only a single phosphorylation site.

Thus, it is within the contemplation of the invention to increase the number of sites (phosphorylation, thiophosphorylation) in proteins which already have one (or a larger number) of such sites.

The origin of the phosphorylatable nucleotide sequence can furthermore be varied. Instead of using the PK nucleotide sequence corresponding to Hu-IFN-gamma, there may be used a PK sequence corresponding to any other interferon (such as murine interferon), or for that matter the PK nucleotide sequence is derivable from any other nucleotide sequence encoding a protein known to be phosphorylatable. In this manner highly interesting phosphorylatable proteins (and phosphorylated proteins) can be made available for practical applications.

Furthermore, it is within the scope of the invention to radio-label proteins, like Hu-IFN-αA and -β which have not been phosphorylatable heretofore with a radioactive label which has advantages over iodine labelling. Accordingly, it is within the scope of the invention to use the sulfur analogs of the radioactive ATP wherein sulfur is substituted for the phosphorus. For instance, the gamma $^{35}$S analog of ATP could be incorporated into the protein at the appropriate recognition site. Thus, the invention contemplates the use of the isotopes of sulfur and phosphorus, like $^{35}$S, $^{38}$S, $^{31}$P, $^{32}$P, and $^{33}$P. Some of these isotopes have not yet been widely used because they are less readily available or because of their respective half-life. Lists of isotopes are of course available. Any isotope which can be introduced into a compound to be labelled is contemplated by this invention.

From Table 3 shown below, it can be observed that $^{38}$S with a half-life of 2.87 hours and an energy of 1.1 Mev may well be an ideal source for irradiation of tumors and other tissues when radiation is deemed appropriate. Proteins phosphorylated with such an isotope with a short half-life of 2.9 hours would have a specific activity about one hundred times the specific activity that is obtainable with $^{32}$P. The short half-life of the isotope also has the advantage that it is eliminated from the patient within a few days. Furthermore, the ability to generate specific activities one-hundred fold that of $^{32}$P permits the use of smaller dosages of the proteins so that antigenic side-effects (that is, antibody production to these proteins) is minimized, The $^{33}$P phosphate produces a β particle with an energy approximately one-seventh that of $^{32}$P. The isotope has a half-life of 24.2 days so that a protein phosphorylated with a phosphate analog containing $^{33}$P would have approximately one-half the specific activity of the analog labelled with $^{32}$P (with a 14.2 day half-life). The $^{33}$P radiation would affect less of the area surrounding the tumor cells than the derivatives containing $^{32}$P. Thus, the use of the products of the invention can bring about important beneficial advantages.

ADDITIONAL APPLICATIONS AND USES OF MODIFIED PROTEINS

The interferons modified in accordance with the invention by the presence of one or more phosphorylated groups—or analogs thereof like sulfur—and proteins so modified, have numerous applications and uses in the biological, medical, biomedical (including therapeutic and diagnostic), and other sciences.

It is contemplated that modified proteins in accordance with the invention can have additional specific uses. A few illustrations of such uses are described below.

1. Pharmacokinetics of Proteins.

It is often useful to follow the fate of injected proteins in animals and patients. It is shown below that the phosphorus attached to some of these proteins is relatively stable in human and fetal calf serum; thus the pharmacokinetics of proteins can be conveniently studied. Thus, phosphorylated proteins are especially well-suited for such applications.

For uses of the phosphorylated proteins or analogs of the invention where the protein is expected to be in contact with human or animal serum, it is necessary that the protein derivative be stable in human or animal serum. The derivative protein should be stable in the serum of the species in which the pharmacokinetic studies (or application) are to be carried out, or in a serum equivalent, i.e., from the biological point of view, to the serum of the species on which the work is to be performed.

For instance, in the work described above, the phosphate linked to Hu-IFN-αA-P1, -P2, and -P3 is stable in fetal calf serum at 37° C. In the presence of human serum, the phosphate linked to Hu-IFN-αA-P1 and to Hu-IFN-αA-P3 was stable at 37° C., but the phosphate linked to Hu-IFN-αA-P2 was labile. After 6 and 16 hours at 37° C. approximately 62% and 74% of the phosphate was hydrolyzed from [$^{32}$PP]Hu-IFN-αA-P2. Thus, for applications where the stability of the phosphorylated derivative is critical, a serum-stable derivative will be used. Similar considerations apply to modified Hu-IFN-β. For applications where stability in serum is not essential, the serum-unstable phosphorylated—or analog—may be used.

The applications described herein are not limited to proteins phosphorylated at the serine residue; it has been described above how kinases phosphorylate other amino acids such as threonine or tyrosine (20, 21, 23). Thus, proteins modified at these amino acids are within the contemplation of the invention. Because of the configuration of such derivatized labelled proteins, it is not to be excluded that their stability in serum may be improved if the corresponding serine-phosphorylated derivative is not adequately serum-stable.

2. General Diagnostic Reagents.

Additional specific applications of the modified proteins of the invention are noteworthy. As referred to herein, virtually all proteins can be engineered to introduce single or multiple phosphorylation (or analog) sites. Such proteins can be used for a wide variety of scientific purposes: to study the fate of these proteins in animals or humans; to study their stabilities; or for use as any laboratory reagent where a radioactive protein is useful.

For example, molecular weight standards are commonly used for polyacrylamide gel electrophoresis. Proteins with phosphorylation sites would make convenient autoradiographic markers such as molecular weight markers, isolectric focusing markers or other markers. For such applications the serum stability is generally not critical, nor is the retention of the biological activity of the protein, e.g., the interferon. Thus, for certain uses or applications it is not essential that a phosphorylatable protein in accordance with the invention have biological activity.

3. Anticancer Therapeutic "Bomb".

A particularly noteworthy and interesting application made possible by the invention is what has been called here in the vernacular, a therapeutic or more specifically an antitumor "therapeutic radiation bomb". Such a biologically-active composition uses biotin coupled to a tumor-specific monoclonal antibody (Mab) (or to Fab or Fab' fragments if more appropriate), and a multiple "modified" streptavidin bound to each Mab-bound biotin, each streptavidin being modified in that it has multiple phosphorylated groups. Since streptavidin is itself a tetramer, multiple radioactive groups are thus provided. These multiple radioactive groups expose the tumor with radiation which is greatly amplified and hence more readily detectable and would produce greater tumor destruction. In the case where it is highly phosphorylatable it is much more easily detectable. Thus, each one of the biotins which is bound to each tumor-specific Mab binds tightly to the multiple streptavidin molecules which in turn contain multiple labelled phosphorus atoms, or their equivalent isotopes.

It is evident that depending on the therapeutic or diagnostic objectives, all streptavidins may -be radioactive-phosphorus labelled or partially or totally radioactive-thiophosphorus labelled, or labelled with different phosphorus or sulfur isotopes, which have different decay modes or levels of radiation energy. Such isotopes are discussed below.

Because antibody molecules are themselves multichain molecules, many sites can be introduced into the antibodies or Fab fragments directly by the procedures of this invention.

4. Hormones, Cytokines, Lymptokines, Growth Factors.

Hormones labelled with radioactive phosphorus or sulfur are another class of biological materials within the scope of this invention. For instance, phosphorylated (e.g., $^{33}P$, $^{32}P$) hormones can be bound to specific cell types differentially over other tissues. Cancerous tissues containing increased number of receptors for such hormones can be treated with appropriately phosphorylated hormones which will then specifically bind to these cells; thus therapy will be significantly improved.

Further, labelled hormones are commonly used for receptor studies to examine their binding to cell surface receptors, to soluble receptors or other reagents and materials.

Typical of the labelled hormones ($^{33}P$, $^{32}P$) contemplated by the invention are growth hormone, insulin, FSH, LH, and others. It is evident such hormones genetically constructed lend themselves to the introduction of one or more putative phosphorylatable or thiophosphorylatable groups.

As noted above for hormones, the same considerations apply to cytokines, lymphokines, growth factors (i.e., IL-1, IL-2, IL-3, TNF-α, TNF-β, the various CSF molecules, erythropoietin EGF, NGF and others) and any proteins with cell and/or tissue specificity to one degree or another.

5. Antibodies.

Streptavidin labelled by means of phosphorylation may be used directly to enhance immunoassays as a substitute for unlabelled streptavidin or enzyme-linked unlabelled streptavidin. The invention also contemplates introducing phosphorus or analog labels into genetically engineered antibodies (see references 93–99), more particularly Mabs, or in the Fab or Fab' fragment. Such Mabs are useful for diagnostic and therapeutic purposes. The phosphorylated Mabs can be made to target specific tumor-associated antigens or a variety of tumors, like breast and colon cancer cells, malignant melanoma cells, ovarian carcinoma cells, and other malignant tumors.

6. Further Therapeutic Uses.

Other uses contemplated in accordance with the invention are as follows: Monoclonal or appropriate cocktails of antibodies and/or antibody fragments (such as the Fab or Fab' fragments) are fruitful molecules in which in accordance with the invention phosphorylation or other labellable sites can be introduced. The use of $^{32}P$ in therapy has been demonstrated for polycythemia vera and other malignancies (116). Thus, it is clear that the high energy β particle is effective as an anticellular agent. The attachment of $^{32}P$ through the introduction of phosphorylation site(s) in Mabs or their appropriate fragments (Fab and Fab') would also be effective for the therapy of tumors to which these monoclonal antibodies are specific. A large number of monoclonal antibodies have been developed to tumor-associated antigens from breast, colon, ovarian, and other adenocarcinomas, malignant melanoma, and many other tumors. Thus, Mabs directed to the tumor associated antigens of these tumors are expected to be highly effective when labelled with $^{32}P$. The labelling can be increased by use of cassettes of phosphorylation sites or directly by introduction of multiple phosphorylation sites into the intact protein or the appropriate fragments through genetic engineering. By "cassette" is meant a multifunctional moiety.

When multiple labelled phosphorylation sites are introduced in accordance with the invention in Mabs, this may reduce the binding specificity and/or affinity of the modified Mabs for the specific epitope targeted. It can be seen that under such circumstances the use of a biotinylated Mab linked to the multiple phosphorylated streptavidin (as described above) has distinct advantages; the specificity of the Mab is not altered and yet the radioactivity of the diagnostic agent has been many-fold enhanced.

The invention also has implications for the preparation of therapeutic agents to which patients are likely to develop an adverse antigenic response. Thus, the monoclonal antibodies can be engineered successively in accordance with the invention with different phosphorylation sites. When introduced into patients who have become sensitive to or who are producing antibodies to the injected antibody because of the phosphorylation site, then by changing to a different phosphorylation site, the antigenic character of the protein can be modified. Thus, it may be possible to use such antibodies in multiple successive therapeutic regimens in patients who are reacting with the antibody of the previous type. For this purpose a series of antibodies with a variety of phosphorylation sites can be developed. Each series would be designed to have a different epitopic structure and be used sequentially. Alternatively a cocktail of such different antibodies can be used initially so that any one is present at a fraction of the total. This would minimize antibody formation to any one of the new sites.

7. Various Isotopes.

In accordance with the invention, as discussed above, phosphorylated derivatives should be serum-stable for certain applications. Various isotopes can be employed that are more effective than others for a specific therapeutic purpose. For example, $^{33}P$ may be substituted for $^{32}P$ in the phosphorylation reaction. It is less likely that $^{35}S$ with a half-life of about 89 days would be normally as useful as an anticellular reagent because it is a low energy β emitter. Nevertheless, conceivably there may be specific uses for $^{35}S$ labelled monoclonal antibodies in therapy and/or diagnosis.

Table 3 below shows various isotopes (and other pertinent particulars) which are especially useful for introduction into proteins in accordance with the invention.

TABLE 3

Isotopes for Labellable Groups

| Isotope | Half-Life | Type of Decay | Energy of Radiation |
|---|---|---|---|
| $^{32}P$ | 14.2 days | β– | 1.707 Mev |
| $^{33}P$ | 24.4 days | β– | 0.25 Mev |
| $^{35}S$ | 87.0 days | β– | 0.167 Mev |
| $^{38}S$ | 2.87 hours | β– | 1.1 Mev |

Decay factors and radioactivity at any given time is available in the literature. For instance, for comparison between $^{125}I$ and $^{131}I$ with, on the other hand, $^{32}P$ and $^{35}S$, reference is made to Appendices, Table A.1.7 (Supplement 2) in Current Protocols in Molecular Biology, cited (43).

Thus, the invention provides tailored-designed proteins for specific biological purposes.

An important implication of this invention is the greater safety of the labelled Mabs due to lower energy emission levels and the nature of the radio emission. Specifically, Mabs labelled with $^{32}P$ or $^{33}P$ have significantly lower energy emission levels than conventional radio-labels for protein such as $^{125}I$; moreover, the decay emission of the phosphorus and sulfur isotopes ($^{32}P$, $^{33}P$, $^{35}P$ and $^{38}S$) is beta particles, as compared to gamma rays of $^{125}I$ as are common in existing labelling protocols.

The safety feature of the beta-labelled proteins, e.g., Mabs or streptavidins (as discussed) in accordance with the invention, is very significant for diagnostic and therapeutic uses of the invention. Beta emitters penetrate the tumor but are not emitted as readily as gamma ray emitters from the patient to surrounding medical staff and non-medical attending individuals.

By selecting $^{35}S$ (which has a half-life of 87 days) and the $^{35}S$ phosphate ATP analog to $^{32}P$ one can significantly increase the effective radioactive life of the therapeutic agent.

Thus, the proteins labelled in accordance with the invention have a spectrum of meaningful advantageous properties heretofore not readily available.

The invention is not limited to the use of unstable isotopes. In the future it may be advantageous to label a protein with a stable isotope that would be suitable for detection by NMR, nuclear activation, or future developed procedures. Nor is it necessary that the label be a "radio" label providing it is an identifiable label.

8. Radioimmunoassays with Labelled Antigens.

In accordance with the invention the phosphorylated proteins can be generally used as the radio-labelled component. These radioimmunoassays can be used with polyclonal as well as with monoclonal antibodies. If the introduction of a new phosphorylation site into a protein changes the antigenic structure of the protein in the area of the phosphorylation site, or even at distant linear positions of the protein, and alters the antigenic behavior, the protein in accordance with the invention, can be modified to introduce a phosphorylation site at a different position so that the antigenic behavior will remain stable and for the protein to bind with the polyclonal or monoclonal antibody of interest.

Thus, the invention provides considerable versatility regarding the position where the label can be introduced. Generally it will be preferred to introduce the phosphorus (or other radio-label) at a site that will not disrupt the antigen-antibody binding.

9. Sandwich Radioimmunoassays.

In sandwich radioimmunoassays with monoclonal antibodies, the introduction of phosphorylation sites into an antibody in accordance with the invention is a sensitive method to follow the binding of the second antibody. Thus, the sensitivity of such sandwich radioimmunoassays can be increased substantially.

Particularly, when multiple phosphorylation sites are introduced in accordance with the invention into the protein directly or by the addition of a fusion phosphorylation cassette, the sensitivity of such assays will be increased many-fold.

Another advantage of the invention is to be noted. Because the phosphorylation reaction is gentle, unlike the iodination or other chemical modifications necessary to radio-label proteins with iodine or other reagents, monoclonal antibodies that are inactivated by the chemical or iodination procedures are not likely to be inactivated by the phosphorylation procedure. Thus, the process of the invention allows for the phosphorylation of proteins normally too sensitive for labelling with iodine. The introduction of a phosphate analog with $^{35}S$ provides a radio-labelled protein derivative with a long half-life (1.5 times longer than $^{125}I$ and 6 times longer than $^{32}P$) Thus, when Mabs are labelled with $^{35}S$, they will have a substantially longer shelf-life compared to the $^{32}P$ or $^{125}I$ radio-labelled derivatives.

As discussed above, the invention allows for the selection of the most appropriate labelling isotope, as compared to $^{125}I$, for instance.

10. Imaging.

Generally for imaging of tumors or tissues in an animal or a patient, a high energy gamma emitter is generally preferable to a high energy B emitter, which by and large would be absorbed by the tissues. However, in certain imaging studies in animals or in patients, Mabs to which $^{32}P$, $^{33}P$ or $^{35}S$ are attached through introduced phosphorylation sites in accordance with the invention may be useful.

For example, it can be seen that Mabs labelled with $^{32}P$, $^{33}P$ or $^{35}S$ could be useful in in vivo studies in which biopsy specimens are to be examined. The spread of a tumor during surgery could be followed by utilizing a radioisotope detector probe to follow the local spread of the tumor and guide the extent of the surgery. In addition, tissue specimens which are fixed or frozen can be taken to which these proteins will remain bound (that is, antibodies to the tumor-associated antigens or other ligands). Thus, autoradiographs of tissue sections can provide information about the extent of tumor spread and the extent of binding of specific monoclonal antibodies to tumor-associated antigens can be thoroughly evaluated. Furthermore, as an in vitro reagent with cells or tissue slices, such labelled antibodies would be highly sensitive reagents to detect tumor-associated antigens or other antigens by the usual types of assays employed.

11. Anti-antibodies.

There are many known uses for anti-antibodies such as anti-mouse, anti-human, anti-sheep, and anti-goat antibodies, etc. or monoclonal antibodies as single entities or as a cocktail. Such antibodies can be engineered in accordance with the invention to introduce single or multiple phosphorylation sites and, accordingly labelled with a variety of isotopes as described above. These provide general reagents where anti-antibodies are necessary, particularly in radioimmunoassays, autoradiography, or any other reactions in which anti-antibodies are useful.

12. Rapid Purification of Phosphorylated Proteins.

The invention has also applications in separating and purifying proteins. Proteins which are phosphorylated can be separated from those which are not; proteins which are more phosphorylated than others can be separated.

For instance, where proteins can be phosphorylated, it is common for only a percentage of the molecules to be phosphorylated. The total phosphorylation, of course, can be enhanced by the introduction of multiple phosphorylation sites in the protein in accordance with the invention so that few molecules escape phosphorylation. To be able to separate the phosphorylated from the non-phosphorylated proteins is especially useful for molecules with a single phosphorylation site where there may be phosphorylated and non-phosphorylated molecules in the population. In this manner, the effectiveness of any phosphorylated derivatives is increased. Separation of phosphorylated from non-phosphorylated molecules can be accomplished by developing polyclonal or monoclonal antibodies to the phosphorylation sites with and/or without derivatized phosphate groups. Such polyclonal and monoclonal antibodies are expected to have considerable value in purifying the proteins and have been described (see for example 119–124).

13. Dephosphorylation of Proteins.

Considerable emphasis has been placed herein on aspects of phosphorylation. It is a consequence of the phosphorylation (with phosphate or thiophosphate groups) that the removal of the label is also facilitated in that dephosphorylation is a milder procedure which tends to be less disruptive of the protein molecule than procedures in the prior art for removal of $^{125}$I from proteins. Thus, in cases where it is useful to remove the radioisotope, this can be achieved relatively easily and gently by an enzyme reaction. A variety of phosphatases can be used for this purpose. Most phosphatases have comparatively low specificity (for example, reference 100, pages 192–193, 203, 223–224, 736–739) although a few have very high specificity such as those acting on sugar phosphates and the enzyme that dephosphorylates glycogen synthetase b and phosphorylase b (47, 100; also reference 101 pages 372–373, for example). Furthermore, specific dephosphorylation of phosphorylated proteins can be achieved by reversal of the reaction of protein-serine and -tyrosine kinases (107). If it is necessary to determine whether in fact the phosphate addition causes a change in the activity of the protein, rather than aging, denaturation, or other manipulations, the phosphate can be removed and the activity of the protein again determined. In such a manner, a definitive understanding of the effect of phosphorylation on the activity of the protein can be assessed. This may be useful in determining the activities of various phosphorylated interferons.

The concept of "dephosphorylation" has an interesting application which is essentially the "converse" of that taught herein. Wherever a site in a protein in the native state is naturally phosphorylatable the removal of that site would be particularly desirable when it is known that the naturally phosphorylatable protein causes some undesired results. An illustration would be proteins associated with oncogenic viruses such as Rous sarcoma virus (RSV) and cellular oncogenes.

14. Phosphorylation Cassettes.

The invention also contemplates an alternative method for labelling proteins without inserting the coding sequence for the phosphorylation site (or cassette) into the nucleotide coding sequence of the protein, and yet still use the invention. This procedure would be particularly useful for large proteins like immunoglobulins for use in various assays. Such alternative method calls for a polypeptide which is phosphorylated to be chemically linked to the large protein. The linking would be by any bifunctional reagent or an activated derivative (like N-hydroxy-succinimide), as is known in the art.

This technique could use a polypeptide with multiple phosphorylation sites in tandem or "cassette" that can be introduced within or at either end of a protein. The DNA coding for the tandem phosphorylation sites would be flanked by restriction sites for easy cleaving and insertion into the DNA containing the coding sequence for the protein to be linked to the larger protein. Such a phosphorylation cassette could be expressed as a small polypeptide then phosphorylated and then chemically linked to the larger protein.

15. Phosphorylatable Human or Animal Donor Genes.

Further, it is within the contemplation of the invention to provide DNA sequences engineered into appropriate vectors or cell lines or even into animals by transgenic techniques. Thus cells or animals could produce phosphorylatable (and/or phosphorylated) proteins such as immunoglobulins after phsphorylation sites are introduced into the proteins by the methods of this invention. Phosphorylatable chimeric antibodies with a mouse variable region and human constant region could be developed (93–99). The human antibodies used as the donor molecule would be engineered to contain single or multiple phosphorylation sites. Analogously, this could be applied to proteins other than immunoglobulins.

16. Use of Phosphorylation Sites to Map Tertiary Structure of Proteins.

By introducing a small phosphorylation recognition site into a protein randomly along the entire linear protein chain, it will be possible to obtain information about the tertiary structure of proteins. The sequence encoding the phosphorylation site is inserted randomly within the DNA sequence encoding the protein of interest. The insertion must be made in such a way that the phosphorylation sequence is in phase with upstream and downstream codons so that an insertion for a phosphorylation site is made without interrupting the phase of translation. The expressed protein, therefore, contains the identical linear sequence of the original protein with an insertion of a phosphorylation site in a given position along the chain. By generating a-large series of insertions (ideally after every amino acid position of the protein chain), it is possible to determine whether the kinase recognizes the sequence in the context in which it is placed by a simple assay to determine the rate and extent of phosphorylation at that position. The rate and extent of phosphorylation depends on the accessibility of that site to the phosphokinase which reflects its position in the tertiary structure (outside, internal, buried, etc.). A complete linear map of the accessibility of the phosphorylation sites along the entire chain will provide an outline of the structural features of the protein that are inside and outside in the tertiary structural configuration. Insertions of amino acids should be designed to minimize perturbations. In some cases insertion of a phosphorylation site can occur by simply changing one or more amino acids rather than inserting several amino acids comprising the phosphorylation recognition site.

The generation of such DNA insertions to make the appropriate variety of insertional mutant proteins can be done in many ways. Insertions can be introduced along a protein chain systematically or randomly by methods comparable to saturation mutagenesis. Alternatively, rather than generating mutants from a given DNA sequence by inserting the sequence encoding the phosphorylation site into the DNA, one can generate synthetic oligonucleotides so that the entire DNA chain is synthesized de novo. Combinations of these procedures and general cloning strategies could easily provide an entire bank of new mutant proteins with phosphorylation sites distributed linearly along the chain.

This procedure provides information about the tertiary structure and folding of the protein in solution. It compliments methods such as x-ray crystallography which will provide tertiary structure information of the proteins in the crystal. Furthermore, the method will be useful to determine the tertiary structure of proteins which have resisted efforts to obtain appropriate crystals for determination of X-ray crystallographic structures.

This aspect is an illustration of a protein having numerous putative phosphorylation sites, ideally after each amino acid in the sequence of the protein; and the corresponding phosphorylated protein. Likewise, this is an illustration of a DNA sequence encoding the putative phosphorylation site (s) inserted in the DNA sequence encoding the selected protein of interest.

17. Other Applications.

There are other applications for the labelled proteins of the invention. In general virtually any protein that contains a label (radio-label, fluorescent-label, chemical-label, enzyme-label, etc.) can alternatively be labelled with phosphate by the introduction of phosphorylation site(s) in accordance with the invention. The purification of such proteins can be followed in a sensitive assay by simply measuring the ability to accept a phosphate group rather than to follow enzyme activity. Such proteins engineered in accordance with the invention, therefore, can be purified easily and themselves be used as a tracer to follow the purification of other proteins to which they are similar. For example, it is likely that a protein with a single phosphorylation site engineered with very little modification of the protein structure itself would be purified similarly to the unmodified protein.

In practice, by having a stock of phosphorylatable proteins or series of markers, the labelled derivatives can be prepared conveniently by the simple phosphorylation reaction when desired. Thus, the proteins of the invention which are phosphorylatable provide a useful inventory of the corresponding labelled proteins.

18. Pharmaceutical and Biologically Active Compositions.

The modified proteins of the invention can be formulated according to known methods to prepare pharmaceutically useful compositions. For instance, the human alpha interferon-like protein hereof is combined in admixture with a pharmaceutically acceptable carrier vehicle. Suitable vehicles and their formulation are described in Remington's *Pharmaceutical Sciences* by E. W. Martin, which is hereby incorporated by reference. Such compositions will contain an effective amount of the interferon-like protein or other proteins hereof together with a suitable amount of vehicle in order to prepare pharmaceutically acceptable compositions suitable for effective administration to the host. The host can be a mammal or not. The carrier may be liquid, solid, or other. Of course therapeutic applications for humans and veterinary applications are intended for the biologically active compositions of the invention. The biologically active composition of the invention is to be administered in a biologically or therapeutically effective amount which can be readily determined by one skilled in the art. Generally it is the smallest amount for which a desired response will be obtained to an amount which is excessive for practical or other purposes.

The biologically active compositions of the invention can also include any other biologically active substance which does not adversely affect the desired activity, particularly the activity or use of the modified protein of the invention.

It is understood that the modified proteins of the invention can be obtained by chemical and/or enzymatic synthesis rather than by recombinant DNA technology.

While reference has been made to particular preferred embodiments and to several uses and applications made possible by the invention, it will be understood that the present invention is not to be construed as limited to such, but rather to the lawful scope of the appended claims and subject matter covered by the doctrine of equivalents.

From the description provided hereinabove it will be appreciated by one skilled in the art that the invention makes a significant and meritorious contribution to the art.

REFERENCES

1. Pestka, S. (1986), *Methods Enzymol.*, 119, 1–845.
2. Pestka, S., Langer, J. A., Zoon, C. K. and Samuel, C. E. (1987), Interferons and Their Actions, *Annu. Rev. Biochem.*, 56, 727–777.
3. Kung, H.-F., and Bekesi, E. (1986), *Methods Enzymol.*, 119, 296–321.
4. Robert-Galliot, B., Commt-Chevalier, M. J., Georges, P., and Chany, C. (1985), *J. Gen. Virol.*, 66, 1439–1448.
5. Langer, J. A., Rashidbaigi, A., and Pestka, S. (1986), *J. Biol. Chem.*, 261, 9801–9804.
6. Rashidbaigi, A., Kung, H.-F., and Pestka, S. (1985), *J. Biol. Chem.*, 260, 8514–8519.
7. Rashidbaigi, A., Langer, J. A., Jung, V., Jones, C., Morse, H. G., Tischfield, J. A., Trill, J. J., Kung, H.-F., and Pestka, S. (1986), *Natl. Acad. Sci, USA*, 83, 384–388.
8. Jung, V., Rashidbaigi, A., Jones, C., Tischfield, A. J., Shows, B. T., and Pestka, S. (1987), *Proc. Natl. Acad. Sci. USA*, 84, 4151–4155.
9. Mariano, T. M., Kozak, C. A., Langer, J. A., and Pestka, S. (1987), *J. Biol. Chem.*, 262, 5812–5814.
10. Arakawa, T., Parker, C. G., and Lai, P.-H. (1986), *Biochem. Biophys. Res. Commun.*, 136, 679–684.
11. Fields, R., Mariano, T., Stein, S., and Pestka, S. (1987), *J. Interferon Res.*, (in press).
12. Crowl, R., Seamans, C., Lomedico, P., and McAndrew, S. (1985), *Gene*, 38, 31–38.
13. Familetti, P. C., Rubinstein, S., and Pestka, S. (1981), *Methods Enzymol.*, 78, 387–394.
14. Bradford, M. M. (1976), *Anal. Biochem.*, 72, 248–254.
15. Maniatis, T., Fritsch, E. F., and Sambrook, J. (1982), *Molecular Cloning, A Laboratory Manual*, New York, Cold Spring Harbor.
16. Staehelin, T., Hobbs, D. S., Kung, H.-F., Lai, C.-Y., and Pestka, S. (1981), *J. Biol. Chem.*, 256, 9750–9754.
17. Langer, J. S., Ortaldo, J. R., and Pestka, S. (1986), *J. Interferon Res.*, 6, 97–105.
18. Laemmli, U. K. (1970), *Nature (Lond)*, 227, 680–685.
19. Wray, W., Boulikas, T., Wray, V. P., and Hancock, R. (1981), *Anal. Biochem.*, 118, 197–203.
20. Kemp, B. E., Graves, D. J., Benjamini, E., and Krebs, E. G. (1977), *J. Biol. Chem.*, 252, 4888–4894.
21. Edelman, A. M., Blumenthal, D. K., and Krebs, E. G. (1987), *Annu. Rev. Biochem.*, 56, 567–613.
22. Glass, D. B., and Krebs, E. G. (1980), *Ann. Rev. Pharmacol. Toxicol.*, 20, 363–388.
23. Maeda, S., McCandliss, R., Gross, M., Sloma, A., Familletti, P. C., Tabor, J. M., Evinger, M., Levy, W. P., and Pestka, S. (1980), *Proc. Natl. Acad. Sci. USA*, 77, 7010–7013; 78, 4648 (1981).

24. Pestka, S. (1983), *Arch. Biochem. Biophys.,* 521, 1–37.
25. Pestka, S. (1986), *Methods Enzymol.,* 119, 3–14.
26. Messing, J. (1983), *Methods in Enzymology,* 101, 20–78.
27. Smith, M., and Gillam, S. (1981), in "Genetic Engineering", Vol. 3, (J. Setlow and A. Hollaender, eds.), p. 1., Plenum Press, New York.
28. Zoon, K. C., and Arnheiter, H. (1984), *Pharmacol. Ther.,* 24, 259–279.
29. Aguet, M. (1980), *Nature (Lond),* 284, 459–461.
30. Czarniecki, C. N., Fennie, C. W., Powers, D. B., and Estell, D. A. (1984), *J. Virol.,* 49, 490–496.
31. Yonehara, S. (1982), *Eur. J. Biochem.,* 125, 529–533.
32. Langer, J. A., and Pestka, S. (1986), *Methods in Enzymol.,* 19, 305–311.
33. Chang, N. T., Kung, H.-F., and Pestka, S. (1983), *Arch. Biochem. Biophys.,* 221, 585–589.
34. Branca, A. A., and Baglioni, C. (1981), *Nature (Lond),* 294, 768–770.
35. Zoon, K. C., Nedden, D. Z., and Arnheiter, H. (1981), *J. Biol. Chem.,* 257, 4695–4697.
36. Mogensen, K. E., Bandu, M. T., Vignaux, F., Aguet, M., and Gresser, I. (1981), *Int. J. Cancer,* 28, 575–582.
37. Joshi, A. R., Sarkar, F. H., and Gupta, S. L. (1982), *J. Biol. Chem.,* 257, 13884–13887.
38. Krebs, A. G., and Beavo, J. A. (1979), *Ann. Rev. Biochem.,* 48, 923.
39. Corbin, J. D., and Hardman, J. G. (1983) *Methods in Enzymology,* 99.
40. Corbin, J. D., and Johnson, R. A. (1988) *Methods in Enzymology,* 159, Section IV: General Methods Related to Protein Phosphatases, pp. 335–453.
41. Staehelin, T., Hobbs, D. S., Kung, H.-F., Lai, C.-Y., and Pestka, S. (1981), *J. Biol. Chem.,* 256, 9750.
42. Knight, E., Hunkapiller, M. W., Korant, B. D., Hardy, R. W. F., and Hood, L. E. (1980), *Science,* 207, 525.
43. Ansbel, F. M., et al., eds. (1987), *Current Protocols in Molecular Biology (Current Protocols),* Brooklyn, N.Y. and Wiley and Sons—Interscience, New York, N.Y.
44. Zoller and Smith (1982), *Nucleic Acids Res.,* 11 (20), 6487.
45. Fantes, K. H. (1986) *Methods in Enzymology,* 119, 233–241.
46. Rehberg, E., Kelder, B., Hoal, E. G., and Pestka, S. (1982), *J. Biol. Chem.,* 257, 11497–11502.
47. Lehninger, A. L. (1976), *Biochemistry,* Worth Publishers, Inc.
48. Scahill, S. J., Devos, R., Van Der Heyden, J., Fiers, W. (1983), *Proc. Natl. Acad. Sci. USA,* 80, 4654–58.
49. Remaut, E., Stanssens, P., Simons, G., Fiers, W. (1986), *Methods Enzymol.,* 119, 366–75.
50. Zinn, K., Mellon, P., Ptashne, M., Maniatis, T. (1982), *Proc. Natl. Acad. Sci. USA,* 79, 4897–901.
51. Canaani, D., Berg, P. (1982), *Proc. Natl. Acad. Sci. USA,* 79, 5166–70.
52. Mulcahy, L., Kahn, M., Kelder, B., Rehberg, E., Pestka, S., et al. (1986), *Methods Enzymol.,* 119, 383–96.
53. Innis, M. A., McCormick, F. (1986), *Methods Enzymol.,* 119, 397–403.
54. Schaber, M. D., DeChiara, T. M., Kramer, R. A. (1986), *Methods Enzymol.,* 119, 416–24.
55. Hitzeman, R. A., Chang, C. N., Matteucci, M., Perry, L., Kohr, W. J., et al. (1986), *Methods Enzymol.,* 119, 424–33.
56. Krisch, H. M. and Allet, B. (1982) *Proc. Natl. Acad. Sci. U.S.A.,* 79, 4937–4941.
57. Simons, G., Remaut, B., Allet, B., Devos, R., and Fiers, W. (1984), *Gene,* 28, 55–65.
58. Hotta, K., Collier, K. J., and Pestka, S. (1986), *Method. in Enzymol.,* 119, 481–485.
59. Sarkar, F. H. and Gupta, S. L. (1986), *Metho. in Enzymol.,* 119, 263–267.
60. Mogensen, K. E. and Uze, G. (1986), *Meth. in Enzymol.,* 119, 267–276.
61. Zur Nedden, D. L. and Zoon K. C. (1986), *Meth. in Enzymol.,* 119, 276–281.
62. Langer, J. A. and Pestka, S. (1986), *Meth. in Enzymol.,* 119, 305–311.
63. Zoon, K. C., Zur Nedden, D., and Arnheiter, H. (1986) *Method in Enzymol.,* 119, 312–315.
64. Hunter, T., Cooper, J. A. (1985), *Ann. Rev. Biochem.,* 54, 897–930.
65. Moschera, J. A., Woehle, D., Tsai, K. P., Chen, C.-H., Tarnowski, S. J. (1986), *Method in Enzymology,* 119, 177–183.
66. Zhao, X-X., Daugherty, B. L., Schwartz, B., Maeda, S., and Pestka, S. (1987), *J. Biol. Req. Homeo. Agents,* 1, 103–108.
67. Carter, P. J., Winter, G., Wilkinson, A. J., and Fersht, A. R. (1984), *Cell,* 38, 835–840.
68. Sanger, F., Nicklen, S., and Coulsen, A. R. (1977), *Proc. Natl. Acad. Sci. U.S.A.,* 74, 5463–5467.
69. Lowry, O. H., Rosebrough, N. J., Farr, A. L., and Randall, R. J. (1951), *J. Biol. Chem.,* 193, 265–275.
70. Crowl, R. (1986) *Methods in Enzymology,* 119, 376–383.
71. Bernard, H.-U., and Helinski, D. R. (1979) *Methods in Enzymology,* 68, 482–492.
72. Rosenberg, M, Ho, Y.-S., and Shatzman, A. (1983) *Methods in Enzymoloqy,* 101, 123–138.
73. Shatzman, A. R., and Rosenberg, M. (1986) *Ann. N. Y. Acad. Sci.,* 478, 233–248
74. Lyons, R. H., Ferguson, B. Q., and Rosenberg, M. (1987) *Mol. Cell. Biol.,* 7, 2451–2456.
75. Watt, R. A., Shatzman, A. R., Rosenberg, M. (1985) *Mol. Cell. Biol.,* 5, 448–456.
76. Shatzman, A. R., and Rosenberg, M. (1987) *Methods in Enzymology,* 152, 661–673.
77. Mott, J. E., Grant, R. A., Ho, Y.-S., and Platt, T. (1985) *Proc. Natl. Acad. Sci. U.S.A.,* 82, 88–92.
78. Gottesman, M. E., and Yarmolinsky, M. B. (1968) *J. Mol. Biol.,* 31, 487–505.
79. Katayama-Fujimura, Y., Gottesman, S., and Maurizi, M. R. (1987) *J. Biol. Chem.,* 262, 4477–4485.
80. Hwang, B. J., Park, W. J., Chung, C. H., and Goldberg, A. L. (1987) *Proc Natl Acad Sci USA,* 84, 5550–5554.
81. Downs, D., Waxman, L., Goldberg, A. L., and Roth, J. (1986) *J. Bacteriol.,* 165, 193–197.
82. Pestka, S. (1972), *J. Biol. Chem.,* 247, 4669–4678.
83. Bray, G. A. (1960), *Anal. Biochem.,* 1, 279–285.
84. Mulligan, R. C., Berg, P., Expression of a bacterial gene in mammalian cells. (1980) *Science,* 209, 1422–1427.
85. Morgan, J. R., Barrandon Y., Green H., Mulligan R. C. (1987) *Science,* 237, 1476–1479.
86. Cone, R. D., Weber-Benarous, A., Baorto, D., Mulligan, R. C. (1987) *Molecular & Cellular Biology,* 7, 887–897.
87. Hellerman, J. G., Cone, R. D., Potts, J. T., Rich, A., Mulligan, R. C., Kronenberg, H. M. (1984) *Proc. Natl. Acad. Sci. U.S.A.,* 81, 5340–5344.
88. Aruffo, A., Seed, B., Molecular cloning of two CD7 (T-cell leukemia antigen) cDNAs by a COS cell expression system (1987) *EMBO J* 1987, 6, 3313–3316.
89. Aruffo, A., Seed, B., Molecular cloning of a CD28 cDNA by a high-efficiency COS cell expression system. (1987) *Proc Natl Acad Sci USA,* 84, 8573–8577.
90. Stamenkovic, I., Seed, B., Analysis of two CDNA clones encoding the B lymphocyte antigen CD20 (B1 , Bp35), a type III integral membrane protein. (1988) *J Exp Med,* 167, 1975–1980.

91. Simmons, D., Seed, B., The Fc gamma receptor of natural killer cells is a phospholipid-linked membrane protein. (1988) *Nature,* 333, 568–570.
92. Mitrani-Rosenbaum, S., Maroteaux, L., Mory, Y., Revel, M., Howley, P. M. (1983) *Mol. Cell. Biol.,* 3, 233–240.
93. Morrison, S. L., Wims, L. A., Oi, V. T., Genetically engineered antibody molecules: new tools for cancer therapy. (1988) *Cancer Invest,* 6, 185–192.
94. Morrison, S. L., Wims, L., Wallick, S., Tan, L., Oi, V. T., Genetically engineered antibody molecules and their application. (1987) *Ann N Y Acad Sci,* 507, 187–198.
95. Morrison, S. L., New approaches to the production of monoclonal antibodies. (1988) *Science,* 239 (4841 Pt 2): G28, G48.
96. Sun, L. K., Curtis, P., Rakowicz-Szulczynska, E., Ghrayeb, J., and others, Chimeric antibody with human constant regions and mouse variable regions directed against carcinoma-associated antigen 17-1A. (1987) *Proc Natl Acad Sci USA,* 84, 214–218.
97. Kobrin, B. J., Milcarek, C., Morrison, S. L., Sequences near the 3' secretion-specific polyadenylation site influence levels of secretion-specific and membrane-specific IgG2b MRNA in myeloma cells. (1986) *Mol Cell Biol,* 6, 1687–1697.
98. Sun, L. K., Curtis, P., Rakowicz-Szulczynska, E., Ghrayeb, J., and others, Chimeric antibodies with 17-1A-derived variable and human constant regions. (1986) *Hybridoma,* 5, Suppl 1, S17–20.
99. Morrison, S. L., Wims, L. A., Kobrin, B., Oi, V. T., Production of novel immunoglobulin molecules by gene transfection. *Mt Sinai J Med (NY)* 1986, 53,175–180.
100. Dixon, M., Webb, E. C., *"The Enzymes"* 2nd edition, Academic Press, New York, 1966 (fifth impression), 950pp.
101. Stryer, L., *"Biochemistry"* 2nd edition, W. H. Freeman and Co., San Francisco, 1981, 949pp.
102. Rashidbaigi, A., Pestka, S. (1987) Chapter 15. "Interferons: Protein Structure" in *"The Interferon System: A Current Review to 1987"* (edited by S. Baron, F. Dianzani, G. J. Stanton and W. R. Fleischman, Jr.) University of Texas Press, Austin, 149–168.
103. Pestka, S. (1985) Chapter 8 "Sources of Interferon for Clinical Use: Preparation and Purification of Recombinant Interferons in *"Interferon 4: In vivo and Clinical Studies"* (edited by N. B. Finter and R. K. Oldham), Elsevier, New York, 107–120.
104. Goeddel, D. V., Shepard, H. M., Yelverton, E., Leung, D., Crea, R., Sloma, A., Pestka, S. (1980) *Nucleic Acids Res.,* 8, 4057–4074.
105. Morse, D. E., Mostellar, R. D., Yanofsky, C. (1970) *Cold Spring Harbor Symp. Quant. Biol.,* 34, 725-.
106. Reznikoff, W. S., Abelson, J. N. (1980) "The lac Promoter" in "The Operon" (edited by J. H. Miller and W. S. Reznikoff) *Cold Spring Harbor Laboratory,* pp 221–243.
107. Kole, H. K., Abdel-Ghany, M., and Racker, E. (1988), *Proc. Natl. Acad. Sci. U.S.A.,* 85, 5849–5853.
108. Hunter, T. (1987), *Cell,* 50, 823–829.
109. Pelech, S. L., and Krebs, E. G. (1987), *J. Biol. Chem.,* 262, 11598–11606.
110. Cooper, J. A., Esch, F. S., Taylor, S. S., and Hunter, T. (1984), *J. Biol. Chem.,* 259, 7835–7841.
111. Zetterqvist, O., and Ragnarsson, U. (1982), *FEBS Letters,* 139, 287–290.
112. Greengard, P. (1978), *Science,* 199, 146–152.
113. Glass, D. B., and Krebs, E. G. (1979), *J. Biol. Chem.,* 254, 9728–9738.
114. Feramisco, J. R., Kemp, B. E., and Krebs, E. G. (1979), *J. Biol. Chem.,* 254, 6987–6990.
115. Marin, O., Meggio, F., Marchiori, F., Borin, G., and Pinna, L. A. (1986), *Eur. J. Biochem.,* 160, 239–244.
116. Spencer, R. P., Seevers, Jr., R. H., and Friedman, A. M. (editors) (1987) Radionuclides in Therapy, CRC Press, Boca Raton, Fla., pp 201.
117. Sommercorn, J., and Krebs, E. G. (1987), *J. Biol. Chem.,* 262, 3839–3843.
118. Kuenzel, E. A., Mulligan, J. A., Sommercorn, J., and Krebs, E. G. (1987), *J. Biol. Chem.,* 262, 9136–9140.
119. Maher, P. A., Nerve growth factor induces protein-tyrosine phosphorylation. *Proc. Natl. Acad. Sci. U.S.A.,* 1988 September;85 (18):6788–91.
120. Linder, M. E., and Burr, J. C., Immunological characterization of proteins detected by phosphotyrosine antibodies in cell's transformed by Rous sarcoma virus. *J. Virol.,* 1988 August; 62 (8):2665–73.
121. Maher, P. A., and Pasquale, E. B., Tyrosine phosphorylated proteins in different tissues during chick embryo development. *J. Cell Biol.,* 1988 May;106(5):1747–55.
122. Glenney, J. R., Jr., Zokas, L., Kamps, M. P., Monoclonal antibodies to phosphotyrosine. *J. Immunol. Methods,* 1988 May 9;109(2):277–85.
123. Zimmerman, U. J., and Schlaepfer, W. W., Clustering of phosphorylated amino acid residues in neurofilament proteins as revealed by 31P NMR. *Biochemistry* 1986 Jun. 17;25(12): 3533–6.
124. Seki, J., Owada, M. K., Sakato, N., Fujuio, H., Direct identification of phosphotyrosine-containing proteins in some retrovirus-transformed cells by use of anti-phosphotyrosine antibody. *Cancer Res.,* 1986 February;46(2): 907–16.

What is claimed is:

1. An isolated nucleic acid encoding a phosphorylatable protein, which phosphorylatable protein comprises an amino acid sequence of a protein not normally phosphorylated in vivo and having a desired bioactivity, which protein has been provided with a heterologous phosphorylation recognition sequence for a kinase, wherein the phosphorylatable protein when phosphorylated on the phosphorylation recognition sequence retains the desired bioactivity.

2. The isolated nucleic acid of claim 1, wherein the protein is a glycoprotein.

3. The isolated nucleic acid of claim 1, wherein the protein is a secreted protein.

4. The isolated nucleic acid of claim 1, wherein the protein is a selected from the group consisting of hormones, cytokines, lymphokines and growth factors.

5. The isolated nucleic acid of claim 1, wherein the phosphorylation recognition sequence is a recognition sequence for a serine/threonine kinase.

6. The isolated nucleic acid of claim 1, wherein the phosphorylation recognition sequence is a recognition sequence for a tyrosine kinase.

7. The isolated nucleic acid of claim 1, comprising two or more phosphorylation recognition sequences.

8. The isolated nucleic acid of claim 1, wherein the phosphorylation recognition sequence comprises the sequence Arg-Arg-Xaa-Ser-Xaa.

9. An expression vector comprising the isolated nucleic acid of claim 1.

10. A host cell which comprises the expression vector of claim 9.

* * * * *